US005519115A

United States Patent [19]
Mapelli et al.

[11] Patent Number: 5,519,115
[45] Date of Patent: May 21, 1996

[54] REVERSE ANTIMICROBIAL PEPTIDES

[75] Inventors: Claudio Mapelli; Michael D. Swerdloff, both of Princeton; Jon I. Williams, Robbinsville; Nicholas P. Everett, Pennington City, all of N.J.

[73] Assignee: Enichem S.p.A., Italy

[21] Appl. No.: 164,151

[22] Filed: Dec. 9, 1993

Related U.S. Application Data

[63] Continuation of Ser. No. 649,784, Feb. 1, 1991, abandoned.

[51] Int. Cl.$^6$ .............. C07K 5/00; C07K 7/00; C07K 17/00
[52] U.S. Cl. .............. 530/324; 530/325; 530/326
[58] Field of Search .............. 530/324–326; 514/12–14

[56] References Cited

U.S. PATENT DOCUMENTS

| | | | |
|---|---|---|---|
| 4,880,779 | 11/1989 | Gallaher | 514/15 |
| 5,045,531 | 9/1991 | Berkowitz et al. | 514/12 |
| 5,185,147 | 2/1993 | Papsidero | 424/89 |
| 5,204,449 | 4/1993 | Puri | 530/391.7 |
| 5,208,220 | 5/1993 | Berkowitz | 514/13 |
| 5,217,956 | 6/1993 | Zasloff | 514/13 |
| 5,221,664 | 6/1993 | Berkowitz et al. | 514/6 |
| 5,254,535 | 10/1993 | Zasloff et al. | 514/12 |
| 5,254,537 | 10/1993 | Zasloff | 514/13 |

FOREIGN PATENT DOCUMENTS

| | | |
|---|---|---|
| 8806597 | 9/1988 | WIPO . |
| 9004408 | 5/1990 | WIPO . |

OTHER PUBLICATIONS

Giovannini et al, Biochem J. vol. 243 p. 113 (1987).

I. Chaiken, et al., "Sequence Simplification and Randomization and the Design of Peptide Recognition Surfaces," *Peptides: Chemistry and Biology*, Proceedings of the 10th American Peptide Symposium, Ed. G. R. Marshall, ESCOM, Leiden, Netherlands, (1988), 354–363.

Shai et al., "Anti–Sense Peptide Recognition of Sense Peptides: Direct Quantitative Characterization with the Ribonuclease S–Peptide System Using Analytical High-Performance Affinity Chromatography," *Biochemistry* (1987), 26, 669–675 1986.

M. M. Shemyakin et al., "Topochemical Approach in Studies of the Structure–Activity Relation: Enantio–enniatin B," *Nature*, Jan. 28, (1967), 412–413, 1969.

M. M. Shemyakin et al., "Topochemical Investigations on Peptide Systems," *Angew–Chem. Internat. Edit.*, 8, (1969), 492–499.

Miklos Bodanszky, Miguel Angel Ondetti, John T. Sheehan and Saul Lande, "Synthetic Peptides Related to Bradykinin", The Squibb Institute for Medical Research, New Jersey (no date).

Murray Goodman and Michael Chorev, Department of Chemistry, University of California, San Diego, La Jolla, California 92093, Received May 24, 1978, "On the Concept of Linear Modified Retro–Peptide Structures" Accounts of Chemical Research, vol. 12, No. 1, Jan., 1979 Chromatography.

*Primary Examiner*—Howard E. Schain
*Assistant Examiner*—Sheela J. Huff
*Attorney, Agent, or Firm*—Lerner, David, Littenberg, Krumholz & Mentlik

[57] ABSTRACT

The present invention relates to several types of antimicrobial peptides including reverse antimicrobial peptides, antimicrobial oligopeptides and other antimicrobial compositions, such as cecropin P1. The present invention also relates to the use of these antimicrobial peptides to provide organisms, and, in particular, plants, with protection from microbial pathogens. Finally, the present invention relates to a screening method which may be useful for determining the phytotoxity of an antimicrobial peptide.

22 Claims, 1 Drawing Sheet

FIGURE 1

| SEQ. ID NO. | PEPTIDES |
|---|---|
| 1 | GIGKFLHSAGKFGKAFVGEIMKS |
| 2 | GIGKFLHSAKKFGKAFVGEIMNS |
| 3 | GIGKXXXXAXXXXKAFVXXIXXX |
| 4 | XXXX |
| 5 | XXXXX |
| 6 | SWLSKTAKKLENSAKKRISEGIAIAIQGGPR |
| 7 | GMASKAGAIAGKIAKVALKAL |
| 8 | KWKLFKKIEKVGQNIRDGIIKAGPAVAVVGQATQIAK-NH$_2$ |
| 9 | SKMIEGVFAKGFKGASHLFKGIG |
| 10 | SNMIEGVFAKGFKKASHLFKGIG |
| 11 | XXXIXXVFAKXXXXAXXXXKGIG |
| 12 | XXMIEXVFAKXFKXAXXLFKGIG |
| 13 | RPGGQIAIAIGESIRKKASNELKKATKSLWS |
| 14 | KAIQTAQGVVAVAPGAKIIGDRINQGVKEIKKFLKWK |
| 15 | LAKLAVKAIKGAIAGAKSAMG |
| 16 | RNSLPKVAYATA |
| 17 | RQIIVFMRKKNFVTKILKKQR |
| 18 | AKSRWY |
| 19 | IGEDVYTPGISGDSLR |
| 20 | GIGKFLREAGKFGKAFVGEIMKP |
| 21 | MGRIARGSKMSSLIVSLLVVLVSLNLASETTA |
| 22 | MGKNGSLCCFSLLLLLLLAGLASGHQVL |
| 23 | GGGGSGGGGSGGGGS |

OLIGONUCLEOTIDES

24    CATGGGTATC GGTAAGTTCC TGCGCGAGGC
TGGCAAGTTC GGCAAGGCCT TCGTGGGCGA
GATCATGAAG CCTTAAGTCG ACCTGCA

25    GGTCGACTTA AGGCTTCATG ATCTCGCCCA
CGAAGGCCTT GCCGAACTTG CCAGCCTCGC
GCAGGAACTT ACCGATACC

26    CATGGGTATC GGTAAGTTCC TGCGCGAGGC
TGGCAAGTTC GGCAAGGCCT TCGTGGGCGA
GATCATGAAG CCTGGTATCG GTAAGTTCCT
GCGCGAGGCT GGCAAGTTCG GCAAGGCCTT
CGTGGGCGAG ATCATGAAGC CTTAAGTCGA
CCTGCA

27    GGTCGACTTA AGGCTTCATG ATCTCGCCCA
CGAAGGCCTT GCCGAACTTG CCAGCCTCGC
GCAGGAACTT ACCGATACCA GGCTTCATGA
TCTCGCCCAC GAAGGCCTTG CCGAACTTGC
CAGCCTCGCG CAGGAACTTA CCGATACC

SEQUENCE LISTING ( 1 ) GENERAL INFORMATION:

( i i i ) NUMBER OF SEQUENCES: 27

( 2 ) INFORMATION FOR SEQ ID NO:1:

( i ) SEQUENCE CHARACTERISTICS:
        ( A ) LENGTH: 23 amino acids
        ( B ) TYPE: amino acid
        ( D ) TOPOLOGY: linear ( i i ) MOLECULE TYPE: peptide ( x i ) SEQUENCE DESCRIPTION: SEQ ID NO:1:

```
Gly Ile Gly Lys Phe Leu His Ser Ala Gly Lys Phe Gly Lys Ala Phe
 1               5                  10                  15
Val Gly Glu Ile Met Lys Ser
                20
```

( 2 ) INFORMATION FOR SEQ ID NO:2:

( i ) SEQUENCE CHARACTERISTICS:
        ( A ) LENGTH: 23 amino acids
        ( B ) TYPE: amino acid
        ( D ) TOPOLOGY: linear ( i i ) MOLECULE TYPE: peptide ( x i ) SEQUENCE DESCRIPTION: SEQ ID NO:2:

```
Gly Ile Gly Lys Phe Leu His Ser Ala Lys Lys Phe Gly Lys Ala Phe
 1               5                  10                  15
Val Gly Glu Ile Met Asn Ser
                20
```

( 2 ) INFORMATION FOR SEQ ID NO:3:

( i ) SEQUENCE CHARACTERISTICS:
        ( A ) LENGTH: 23 amino acids
        ( B ) TYPE: amino acid
        ( D ) TOPOLOGY: linear ( i i ) MOLECULE TYPE: peptide ( x i ) SEQUENCE DESCRIPTION: SEQ ID NO:3:

```
Gly Ile Gly Lys Xaa Xaa Xaa Xaa Ala Xaa Xaa Xaa Xaa Lys Ala Phe
 1               5                  10                  15
Val Xaa Xaa Ile Xaa Xaa Xaa
                20
```

( 2 ) INFORMATION FOR SEQ ID NO:4:

( i ) SEQUENCE CHARACTERISTICS:
        ( A ) LENGTH: 4 amino acids
        ( B ) TYPE: amino acid
        ( D ) TOPOLOGY: linear ( i i ) MOLECULE TYPE: peptide ( x i ) SEQUENCE DESCRIPTION: SEQ ID NO:4:

```
Xaa Xaa Xaa Xaa
 1
```

( 2 ) INFORMATION FOR SEQ ID NO:5:

( i ) SEQUENCE CHARACTERISTICS:
        ( A ) LENGTH: 5 amino acids
        ( B ) TYPE: amino acid
        ( D ) TOPOLOGY: linear ( i i ) MOLECULE TYPE: peptide ( x i ) SEQUENCE DESCRIPTION: SEQ ID NO:5:

```
Xaa  Xaa  Xaa  Xaa  Xaa
1                      5
```

( 2 ) INFORMATION FOR SEQ ID NO:6:

( i ) SEQUENCE CHARACTERISTICS:
        ( A ) LENGTH: 31 amino acids
        ( B ) TYPE: amino acid
        ( D ) TOPOLOGY: linear ( i i ) MOLECULE TYPE: peptide ( x i ) SEQUENCE DESCRIPTION: SEQ ID NO:6:

```
Ser  Trp  Leu  Ser  Lys  Thr  Ala  Lys  Lys  Leu  Glu  Asn  Ser  Ala  Lys  Lys
1                   5                        10                            15

Arg  Ile  Ser  Glu  Gly  Ile  Ala  Ile  Ala  Ile  Gln  Gly  Gly  Pro  Arg
                    20                       25                       30
```

( 2 ) INFORMATION FOR SEQ ID NO:7:

( i ) SEQUENCE CHARACTERISTICS:
        ( A ) LENGTH: 21 amino acids
        ( B ) TYPE: amino acid
        ( D ) TOPOLOGY: linear ( i i ) MOLECULE TYPE: peptide ( x i ) SEQUENCE DESCRIPTION: SEQ ID NO:7:

```
Gly  Met  Ala  Ser  Lys  Ala  Gly  Ala  Ile  Ala  Gly  Lys  Ile  Ala  Lys  Val
1                   5                        10                            15

Ala  Leu  Lys  Ala  Leu
                    20
```

( 2 ) INFORMATION FOR SEQ ID NO:8:

( i ) SEQUENCE CHARACTERISTICS:
        ( A ) LENGTH: 37 amino acids
        ( B ) TYPE: amino acid
        ( D ) TOPOLOGY: linear ( i i ) MOLECULE TYPE: peptide ( i x ) FEATURE:
        ( A ) NAME/KEY: Modified-site
        ( B ) LOCATION: 37
        ( D ) OTHER INFORMATION: /note="THE C-TERMINAL AMINO ACID
             IS IN THE FORM OF AN AMIDE"

( x i ) SEQUENCE DESCRIPTION: SEQ ID NO:8:

```
Lys  Trp  Lys  Leu  Phe  Lys  Lys  Ile  Glu  Lys  Val  Gly  Gln  Asn  Ile  Arg
1                   5                        10                            15

Asp  Gly  Ile  Ile  Lys  Ala  Gly  Pro  Ala  Val  Ala  Val  Val  Gly  Gln  Ala
               20                       25                       30

Thr  Gln  Ile  Ala  Lys
               35
```

( 2 ) INFORMATION FOR SEQ ID NO:9:

( i ) SEQUENCE CHARACTERISTICS:
 ( A ) LENGTH: 23 amino acids
 ( B ) TYPE: amino acid
 ( D ) TOPOLOGY: linear ( i i ) MOLECULE TYPE: peptide ( x i ) SEQUENCE DESCRIPTION: SEQ ID NO:9:

Ser Lys Met Ile Glu Gly Val Phe Ala Lys Gly Phe Lys Gly Ala Ser
1               5                   10                  15

His Leu Phe Lys Gly Ile Gly
            20

( 2 ) INFORMATION FOR SEQ ID NO:10:

( i ) SEQUENCE CHARACTERISTICS:
  ( A ) LENGTH: 23 amino acids
  ( B ) TYPE: amino acid
  ( D ) TOPOLOGY: linear ( i i ) MOLECULE TYPE: peptide ( x i ) SEQUENCE DESCRIPTION: SEQ ID NO:10:

Ser Asn Met Ile Glu Gly Val Phe Ala Lys Gly Phe Lys Lys Ala Ser
1               5                   10                  15

His Leu Phe Lys Gly Ile Gly
            20

( 2 ) INFORMATION FOR SEQ ID NO:11:

( i ) SEQUENCE CHARACTERISTICS:
  ( A ) LENGTH: 23 amino acids
  ( B ) TYPE: amino acid
  ( D ) TOPOLOGY: linear ( i i ) MOLECULE TYPE: peptide ( x i ) SEQUENCE DESCRIPTION: SEQ ID NO:11:

Xaa Xaa Xaa Ile Xaa Xaa Val Phe Ala Lys Xaa Xaa Xaa Xaa Ala Xaa
1               5                   10                  15

Xaa Xaa Xaa Lys Gly Ile Gly
            20

( 2 ) INFORMATION FOR SEQ ID NO:12:

( i ) SEQUENCE CHARACTERISTICS:
  ( A ) LENGTH: 23 amino acids
  ( B ) TYPE: amino acid
  ( D ) TOPOLOGY: linear ( i i ) MOLECULE TYPE: peptide ( x i ) SEQUENCE DESCRIPTION: SEQ ID NO:12:

Xaa Xaa Met Ile Glu Xaa Val Phe Ala Lys Xaa Phe Lys Xaa Ala Xaa
1               5                   10                  15

Xaa Leu Phe Lys Gly Ile Gly
            20

( 2 ) INFORMATION FOR SEQ ID NO:13:

( i ) SEQUENCE CHARACTERISTICS:
  ( A ) LENGTH: 31 amino acids
  ( B ) TYPE: amino acid
  ( D ) TOPOLOGY: linear ( i i ) MOLECULE TYPE: peptide ( x i ) SEQUENCE DESCRIPTION: SEQ ID NO:13:

Arg Pro Gly Gly Gln Ile Ala Ile Ala Ile Gly Glu Ser Ile Arg Lys
1               5                   10                  15

Lys Ala Ser Asn Glu Leu Lys Lys Ala Thr Lys Ser Leu Trp Ser
                20              25                  30

( 2 ) INFORMATION FOR SEQ ID NO:14:

( i ) SEQUENCE CHARACTERISTICS:
( A ) LENGTH: 37 amino acids
( B ) TYPE: amino acid
( D ) TOPOLOGY: linear ( i i ) MOLECULE TYPE: peptide ( x i ) SEQUENCE DESCRIPTION: SEQ ID NO:14:

Lys Ala Ile Gln Thr Ala Gln Gly Val Val Ala Val Ala Pro Gly Ala
1               5                   10                  15

Lys Ile Ile Gly Asp Arg Ile Asn Gln Gly Val Lys Glu Ile Lys Lys
                20              25                  30

Phe Leu Lys Trp Lys
                35

( 2 ) INFORMATION FOR SEQ ID NO:15:

( i ) SEQUENCE CHARACTERISTICS:
( A ) LENGTH: 21 amino acids
( B ) TYPE: amino acid
( D ) TOPOLOGY: linear ( i i ) MOLECULE TYPE: peptide ( x i ) SEQUENCE DESCRIPTION: SEQ ID NO:15:

Leu Ala Lys Leu Ala Val Lys Ala Ile Lys Gly Ala Ile Ala Gly Ala
1               5                   10                  15

Lys Ser Ala Met Gly
                20

( 2 ) INFORMATION FOR SEQ ID NO:16:

( i ) SEQUENCE CHARACTERISTICS:
( A ) LENGTH: 12 amino acids
( B ) TYPE: amino acid
( D ) TOPOLOGY: linear ( i i ) MOLECULE TYPE: peptide ( x i ) SEQUENCE DESCRIPTION: SEQ ID NO:16:

Arg Asn Ser Leu Pro Lys Val Ala Tyr Ala Thr Ala
1               5                   10

( 2 ) INFORMATION FOR SEQ ID NO:17:

( i ) SEQUENCE CHARACTERISTICS:
( A ) LENGTH: 21 amino acids
( B ) TYPE: amino acid
( D ) TOPOLOGY: linear ( i i ) MOLECULE TYPE: peptide ( x i ) SEQUENCE DESCRIPTION: SEQ ID NO:17:

Arg Gln Ile Ile Val Phe Met Arg Lys Lys Asn Phe Val Thr Lys Ile
1               5                   10                  15

Leu Lys Lys Gln Arg
                20

( 2 ) INFORMATION FOR SEQ ID NO:18:

( i ) SEQUENCE CHARACTERISTICS:
  ( A ) LENGTH: 6 amino acids
  ( B ) TYPE: amino acid
  ( D ) TOPOLOGY: linear ( i i ) MOLECULE TYPE: peptide ( x i ) SEQUENCE DESCRIPTION: SEQ ID NO:18:

```
Ala  Lys  Ser  Arg  Trp  Tyr
 1                    5
```

( 2 ) INFORMATION FOR SEQ ID NO:19:

( i ) SEQUENCE CHARACTERISTICS:
  ( A ) LENGTH: 16 amino acids
  ( B ) TYPE: amino acid
  ( D ) TOPOLOGY: linear ( i i ) MOLECULE TYPE: peptide ( x i ) SEQUENCE DESCRIPTION: SEQ ID NO:19:

```
Ile  Gly  Glu  Asp  Val  Tyr  Thr  Pro  Gly  Ile  Ser  Gly  Asp  Ser  Leu  Arg
 1                    5                        10                       15
```

( 2 ) INFORMATION FOR SEQ ID NO:20:

( i ) SEQUENCE CHARACTERISTICS:
  ( A ) LENGTH: 23 amino acids
  ( B ) TYPE: amino acid
  ( D ) TOPOLOGY: linear ( i i ) MOLECULE TYPE: peptide ( x i ) SEQUENCE DESCRIPTION: SEQ ID NO:20:

```
Gly  Ile  Gly  Lys  Phe  Leu  Arg  Glu  Ala  Gly  Lys  Phe  Gly  Lys  Ala  Phe
 1                    5                        10                       15

Val  Gly  Glu  Ile  Met  Lys  Pro
                 20
```

( 2 ) INFORMATION FOR SEQ ID NO:21:

( i ) SEQUENCE CHARACTERISTICS:
  ( A ) LENGTH: 32 amino acids
  ( B ) TYPE: amino acid
  ( D ) TOPOLOGY: linear ( i i ) MOLECULE TYPE: peptide ( x i ) SEQUENCE DESCRIPTION: SEQ ID NO:21:

```
Met  Gly  Arg  Ile  Ala  Arg  Gly  Ser  Lys  Met  Ser  Ser  Leu  Ile  Val  Ser
 1                    5                        10                       15

Leu  Leu  Val  Val  Leu  Val  Ser  Leu  Asn  Leu  Ala  Ser  Glu  Thr  Thr  Ala
                 20                       25                       30
```

( 2 ) INFORMATION FOR SEQ ID NO:22:

( i ) SEQUENCE CHARACTERISTICS:
  ( A ) LENGTH: 28 amino acids
  ( B ) TYPE: amino acid
  ( D ) TOPOLOGY: linear ( i i ) MOLECULE TYPE: peptide ( x i ) SEQUENCE DESCRIPTION: SEQ ID NO:22:

```
Met  Gly  Lys  Asn  Gly  Ser  Leu  Cys  Cys  Phe  Ser  Leu  Leu  Leu  Leu  Leu
 1                    5                        10                       15
```

```
      Leu  Leu  Ala  Gly  Leu  Ala  Ser  Gly  His  Gln  Val  Leu
                      20                        25
```

( 2 ) INFORMATION FOR SEQ ID NO:23:

( i ) SEQUENCE CHARACTERISTICS:
        ( A ) LENGTH: 15 amino acids
        ( B ) TYPE: amino acid
        ( D ) TOPOLOGY: linear ( i i ) MOLECULE TYPE: peptide ( x i ) SEQUENCE DESCRIPTION: SEQ ID NO:23:

```
      Gly  Gly  Gly  Gly  Ser  Gly  Gly  Gly  Gly  Ser  Gly  Gly  Gly  Gly  Ser
      1              5                        10                       15
```

( 2 ) INFORMATION FOR SEQ ID NO:24:

( i ) SEQUENCE CHARACTERISTICS:
        ( A ) LENGTH: 87 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:24:

```
CATGGGTATC  GGTAAGTTCC  TGCGCGAGGC  TGGCAAGTTC  GGCAAGGCCT  TCGTGGGCGA        60
GATCATGAAG  CCTTAAGTCG  ACCTGCA                                              87
```

( 2 ) INFORMATION FOR SEQ ID NO:25:

( i ) SEQUENCE CHARACTERISTICS:
        ( A ) LENGTH: 79 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:25:

```
GGTCGACTTA  AGGCTTCATG  ATCTCGCCCA  CGAAGGCCTT  GCCGAACTTG  CCAGCCTCGC        60
GCAGGAACTT  ACCGATACC                                                        79
```

( 2 ) INFORMATION FOR SEQ ID NO:26:

( i ) SEQUENCE CHARACTERISTICS:
        ( A ) LENGTH: 156 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:26:

```
CATGGGTATC  GGTAAGTTCC  TGCGCGAGGC  TGGCAAGTTC  GGCAAGGCCT  TCGTGGGCGA        60
GATCATGAAG  CCTGGTATCG  GTAAGTTCCT  GCGCGAGGCT  GGCAAGTTCG  GCAAGGCCTT       120
CGTGGGCGAG  ATCATGAAGC  CTTAAGTCGA  CCTGCA                                   156
```

( 2 ) INFORMATION FOR SEQ ID NO:27:

( i ) SEQUENCE CHARACTERISTICS:
        ( A ) LENGTH: 148 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:27:

```
GGTCGACTTA  AGGCTTCATG  ATCTCGCCCA  AGAAGGCCTT  GCCGAACTTG  CCAGCCTCGC    60
GCAGGAACTT  ACCGATACCA  GGCTTCATGA  TCTCGCCCAC  GAAGGCCTTG  CCGAACTTGC   120
CAGCCTCGCG  CAGGAACTTA  CCGATACC                                        148
```

REVERSE ANTIMICROBIAL PEPTIDES

This is a continuation of application Ser. No. 07/649,784 filed Feb. 1, 1991, now abandoned.

FIELD OF THE INVENTION

The invention relates to certain antimicrobial compositions including reverse antimicrobial peptides active against pathogens, antimicrobial oligopeptides, and mixtures including a mixture of antimicrobial peptides and the use of these compositions to provide protection from pathogens and, particularly, from plant pathogens.

BACKGROUND OF THE INVENTION

A large segment of the scientific community is involved in discovering more about the structure and function of the human immunological response and pathogen defense systems including those conditions such as, for example, acquired immune deficiency syndrome and associated diseases brought about by infections with opportunistic pathogens which may effect or compromise those systems. As part of this investigation, a number of inquiries have been made into the biochemistry of the immune or defense systems of other creatures, both as models upon which to base theory, and as a source of potentially transplantable factors.

One such group of immune or defense factors are the antimicrobial peptides first reported in 1987 by two groups of researchers, one headed by Dudley Williams and one headed by Michael Zasloff. These groups successfully characterized and reported a number of peptides which are secreted by the glands contained within the skin of the African Clawed Frog, *Xenopus laevis* which appear to have antimicrobial activity. See, Giovannini, et al., "Biosynthesis and Degradation of Peptides Derived from *Xenopus laevis* Prohormones" *Biochem. J.* 243, (1987), 113–120; and Zasloff, "Magainins, a Class of Anti-Microbial Peptides from Xenopus Skin: Isolation, characterization of two active forms and partial cDNA sequence of a precursor", *Proc. Natl. Acad. Sci.* (USA) 84, (1987), 5449–5453, and Terry et al., "The cDNA Sequence Coding for Prepro-PGS (Prepro-Magainins) and Aspects of the Processing of This Prepro-Polypeptide," *J. Biol. Chemistry*, 263, (1988), 5745–5751. Their research was prompted, at least in part, by the observation that this species of frog has remarkable recuperative power and the ability to remain free from infection during wound-healing with little or no post operative care. These peptides are collectively referred to as magainins.

The published works regarding magainins and other classes of antibiotic or antimicrobial peptides (for example, cecropins, defensins, sarcotoxins, melittins, and the like) of which the inventors are aware have generally centered on human pharmaceutical-related health technologies. Exceptions, however, include two patent applications filed by Jaynes et al., (WO 89/04371 and WO 88/00976) which generally relate to plants which have been genetically enhanced for disease resistance. Jaynes et al. have speculated without supporting data that genetically transformed plants may be produced which contain an expressible heterologeous gene for an antimicrobial peptide. In this way, it is hoped that the plant has enhanced resistance to disease. According to Jaynes et al., however, peptides such as melittins, bombinins, and magainins having less than about 30 residues are not preferred for use in crop protection applications.

Others have published information relating to the existence of antimicrobial peptides in plants or, in fact, the use of antimicrobial peptides to protect plants from plant pathogens. See, EPO 0,299,828; P. Casteels et al., "Apidaecins: Antibacterial Peptides From Honeybees," *The EMBO J.* 8, (1989), 2387–2391; F. Ebrahim-Nesbat et al., "Cultivar-Related Differences in the Distribution of Cell-Wall-Bound Thionins in Compatible and Incompatible Interactions Between Barley and Powdery Mildew," *Planta* 179, (1989), 203–210. Most of this work centered upon the identification and use, either in plants or animals, of basically full-length natural antimicrobial peptides.

In addition to this research, a number of variations on naturally occurring peptides have been investigated. Specifically, a number of magainin based derivatives having varying degrees of activity have been produced and investigated. See Juretic, et al., "Magainin 2 Amide and Analogues, Antimicrobial Activity, Membrane Depolarization and Susceptibility of Proteolysis," *Febs Lett.* 249, (1989), 219–223; Chen, et al, "Synthetic Magainin Analogues With Improved Antimicrobial Activity," *Febs Lett.* 236, (1988), 462–466; Chen et al, U.S. patent application Ser. No. 280,363, filed Dec. 6, 1988; Cuervo, et al., "Synthesis and Antimicrobial Activity of Magainin Alanine Substitution Analogs," Proceedings of the Eleventh American Peptide Symposium; Peptides: Chemistry, Structure and Biology (J. E. Rivier, et al.), (1990), pp. 124–126, published by ESCOM-Leiden, Neth.; Cuervo, et al., "The Magainins: Sequence Factors Relevant to Increased Antimicrobial Activity and Decreased Hemolytic Activity," Peptide Research 1, (1988), 81–86; World Patent Application No. WO 88/06597; and Japanese Patent Application No. JP-1/299,299. These include the complete single residue omission analogue series of Magainin 1 and 2, select N-terminal omissions of Magainin 2, as well as the complete alanine (Ala) replacement analog series of Magainin 2, and Magainin 2 derivatives which may be useful as an antibiotic and/or an anti-cancer drug and which are substituted at the 5th and 12th positions.

Another such investigation was conducted by Bascomb et al. which is reported in U.S. patent application Ser. No. 566,152 filed on Aug. 10, 1990, the complete text of which is hereby incorporated by reference. Bascomb et al. identified specific positions on natural magainins that are important for activity, proteolytic sensitivity to at least one plant protease, and/or phytotoxicity. Bascomb et al. also developed strategic amino acid substitutions and/or deletions relating thereto.

The aforementioned efforts are far from complete. They have not, as yet, provided a complete picture of even the simplest model for relating antibiotic peptide structure to function. Therefore, there still remains a need for further investigation into antimicrobial peptides and their uses. Furthermore, in light of the promising information provided by those including Bascomb et al. who have modified natural peptide structures, further investigation into the effects of various modified forms of naturally occurring peptides may provide both useful models for further investigation and, indeed, useful peptides for combatting plant and animal microbial pathogens.

The present invention is directed to several discoveries. First, the present inventors have identified certain new peptides and their functional derivatives including reverse antimicrobial peptides which are active against at least one microbial pathogen and, preferably, at least one plant pathogen. They have also discovered the usefulness of the non-amide form of a previously identified compound (PGL$^a$), known herein as PGL$^c$. The inventors have also discovered oligopeptides having antimicrobial activity, and that these peptides and oligopeptides, as well as peptides such as, for example, cecropin P1 (herein termed P1 since it is of porcine origin, not insect origin), are useful in providing protection against plant pathogens, either alone or when included within mixtures. These peptides or their functional derivative peptides may additionally possess decreased phytotoxicity and/or decreased sensitivity to proteolytic degradation. Thus, these compounds and certain mixtures thereof are useful for providing protection against at least one plant pathogen and, may indeed have broader application into animals and foodstuffs.

OBJECTS AND SUMMARY OF THE INVENTION

One of the objects of the present invention is to provide compounds which are antimicrobial and which can provide protection against at least one pathogen.

Another object of the present invention is the provision of antimicrobial peptides which are particularly active against at least one plant pathogen.

Still another object of the present invention is the provision of antimicrobial peptides active against at least one plant pathogen which may additionally have a reduced sensitivity to proteolysis and/or reduced phytotoxicity.

Yet another object of the present invention is to provide such antimicrobial peptides which may be naturally expressed as products of living cells.

In accordance with these objects, one aspect of the present invention provides a new class of compositions known as reverse antimicrobial peptides having activity against at least one microbial pathogen, and in particular, against at least one microbial plant pathogen. Such compounds may be designated "RAMPPs" and "RAMPPPs" respectively. This new class of compositions includes the peptide having the structure of (SEQ ID NO. 9) which is the exact reverse of the previously identified natural Magainin 1 peptide (SEQ ID NO. 1). Another member of this class of compositions is the peptide having the structure of (SEQ ID NO. 10) which is the identical but reverse sequence of the natural peptide designated Magainin 2 (SEQ ID NO. 2).

Reverse structural compositions have been disclosed in I. Chaiken, et al., "Sequence Simplification and Randomization and the Design of Peptide Recognition Surfaces," Peptides:*Chemistry and Biology*, Proceedings of the 10th American Peptide Symposium, Ed. G. R. Marshall, ESCOM, Leiden, Netherlands, (1988), 354–363. These peptides were used to mimic recognition surfaces. See also Shai et al., "Anti-Sense Peptide Recognition of Sense Peptides: Direct Quantitative Characteriztion with the Ribonuclease S-Peptide System Using Analytical High-Performance Affinity Chromatography," *Biochemistry* (1987), 26, 669–675. Additionally, the reverse structure of D-amino acid-containing enniatin, an antimicrobial cyclic peptide, was reported in M. M. Shemyakin et al., "Topochemical Approach in Studies of the Structure-Activity Relation: Enantio-enniatin B," Nature, Jan. 28, (1967), 412–413, and M. M. Shemyakin et al., "Topochemical Investigations on Peptide Systems," *Angew-Chem. Internat Edit.*, 8, (1969), 492–499.

When Magainins 1 and 2 were first investigated by Bascomb, et al., it was discovered that these peptides could provide protection against at least one plant pathogenic fungus and could provide some level of protection against plant pathogenic bacteria. However, these compounds were found to have some undesirable properties which raised serious questions with regard to their incorporation into and use with plants, animals, foodstuffs and the like. Specifically, it was discovered that these peptides are subject to extensive proteolytic degradation by enzymes contained within plant tissue or isolated from animal sources. Additionally, Magainin 2 has a relatively high level of phytotoxicity. Thus, the incorporation of such natural peptides into plants could cause the death of the host cells. At best, these peptides would provide little or no protection at all as the plant cells would digest them.

In one attempt to remedy the deficiencies of these naturally occurring peptides, Bascomb, et al., supra undertook an extensive investigation into the structure and function of Magainins 1 and 2 and compounds which they derived therefrom. Bascomb, et al. identified modifications which reduced the phytotoxicity and/or the rate of proteolytic degradation of modified Magainin peptides, while at the same time maintaining an acceptable level of protection against at least one plant pathogen. Bascomb, et al. also discussed a number of modifications which rendered these peptides more useful for various applications including providing protection against plant pathogens.

It has now been found that acceptable activity and, therefore, acceptable levels of protection against at least one microbial pathogen and, in particular, at least one microbial plant pathogen may also be obtained by reversing the sequence of the amino acids contained within naturally occurring antimicrobial peptides while maintaining the directionality of the peptide bonds. Furthermore, the present inventors have discovered that RAMPPS and, more particularly, RAMPPPS may additionally possess relatively low phytotoxicity and/or low susceptibility to proteolytic degradation. Thus these peptides represent a new and important class of peptides which may be suitable for use with and/or for incorporation into plants or animals to provide them with protection against plant pathogens.

Another reverse peptide which shows promise has the amino acid structure of (SEQ ID NO. 14) which is the reverse of Cecropin A having the amino acid structure of (SEQ ID NO. 8) and being in the C-terminal amide form. Cecropins and derivatives thereof have been identified as active compositions of insect origin and one which are potentially useful against both plant and animal pathogens. See, J. M. Jaynes, et al., "In Vitro Cytocidal Effect of Lytic Peptides on Several Transformed Mammalian Cell Lines," *Peptide Res.* 2, 1989, 157–160; J. M. Jaynes, et al., "*In Vitro Cytocidal Effect of Novel Lytic Peptides on Plasmodium falciparum and Trypanosoma cruzi*", FASEB J. 2, 1988, 2778–83; J. M. Jaynes et al., "Increasing Bacterial Resistance in Plants Utilizing Antibacterial Genes from Insects", *Bioassays* 6, (1987), 263–270; J. M. Jaynes et al., "Method for Introduction of Disease and Pest Resistance into Plants and Novel Genes Incorporated into Plants Which Code Therefor," WO 88/00976, 11 Feb. 1988, U.S. application Ser. No. 889,225, 25 Jul. 1986; J. M. Jaynes et al., "Plants Genetically Enhanced for Disease Resistance," WO 89/04371, 18 May 1989, U.S. application Ser. No. 115,941, 2 Nov. 1987. However, the present inventors have discovered that, for example, Cecropin A (SEQ ID NO. 8) (in the C-terminal amide form) is very phytotoxic. The reversal of its amino acid sequence (SEQ ID NO. 14) should, therefore, provide the same advantages as has been discovered when the structure of Magainin-based peptides are reversed. The reverse antimicrobial peptides of P1 having the structure of (SEQ ID NO. 13) and PGL$^c$ having the structure of (SEQ ID NO. 15) and equivalent peptides are also contemplated as are the functional derivatives of all of these reverse peptides.

The present invention includes the use of these peptides to provide protection against at least one microbial pathogen, as well as reverse peptides which include a signal peptide attached to their N-terminus that which allows these reverse antimicrobial peptides to be targeted and transported to the extracellular space between, for example, plant cells in culture or plant tissue.

In accordance with the above-stated objectives, another aspect of the present invention is the provision of a new group of chemical compounds having the structure of (SEQ ID NO. 7) and their nonamide functional derivatives. The present inventors have found that the non-amide containing form of naturally occurring PGL$^a$ (the non-amide form being known herein as PGL$^c$) has activity against at least one microbial pathogen and preferably against at least one microbial plant pathogen. See Williams et al., "Raman Spectroscopy of Synthetic Antimicrobial Frog Peptides Magainin 2a and PGL$^a$," *Biochemistry*, 29, (1990), 4490–4496.

In accordance with still another aspect of the present invention, the present inventors have also developed a new class of substituted peptides containing a solitary Cys substituted within their structure other than by substituting for or appending to the N- or C-terminus thereof. These peptides have activity against at least one microbial pathogen and, preferably against at least one microbial plant pathogen and are ideally suited for use in specific disulfide linked oligopeptides provided herein.

Another of the objects of the present invention is the provision of compounds which are antimicrobial and which can provide protection against at least one pathogen.

Another object of the present invention is the provision of antimicrobial peptides which are particularly active against at least one plant pathogen.

Still another object of the present invention is the provision of antimicrobial peptides active against at least one plant pathogen which may additionally have a reduced sensitivity to proteolysis.

Another object of the present invention is to provide compositions which may be easily excreted to subcellular compartments and, more particularly, the extracellular space between cells in cultured cells or in plant tissue.

Yet another object of the present invention is the provision of peptides which will remain active in the extracellular space between cells for relatively long periods of time.

Still another object of the present invention is the provision of a peptide which can be used as a precursor for the delivery of a plurality of differing antimicrobial peptides.

Yet another object of the present invention is the provision of peptides which may be easily expressed by normal cellular mechanisms.

In accordance with these and other objects, one aspect of the present invention is the provision of a new class of compounds which are antimicrobial oligopeptides. These new peptides may additionally have low susceptibility to proteolytic degradation.

In the broadest sense, an oligopeptide in accordance with the present invention is a functional protein containing at least two peptide subunits as the at least one first peptide monomer and the at least one second peptide monomer. These two peptide monomers, or any additional peptide monomers which make up the individual oligopeptide, are interconnected either directly through a peptide bond or indirectly through a disulfide bond or one or more bridges. See L. Regan and W. DeGrado, "Characterization of a Helical Protein Designed From First Principles," *Science*, 241, (1988), 976–978 and Cheng et al., infra (describing dimers and multimers of non-antimicrobial peptides). Additionally, oligopeptides in accordance with the present invention may be joined by a plurality of bridges and a disulfide linkage, either by using one or more bridges to separate at least one peptide monomer from the Cys involved in the disulfide linkage, or by allowing a disulfide linkage to form which traverses at least one of the peptide bonds joining the peptide units to the bridge.

In accordance with the present invention, each of the individual peptide monomers from which the oligopeptides are constructed are generally themselves antimicrobial peptides which are active against microbial pathogens and which, in a more preferred embodiment, are active against at least one microbial plant pathogen. However, each of the peptide monmers need not exhibit such activity alone so long as at least two of the peptide subunits, other than any bridge, have activity against at least one microbial pathogen and, preferably, against at least one microbial plant pathogen. The resulting oligopeptide is itself active against at least one microbial pathogen and again, more preferably, at least one microbial plant pathogen. Thus, for a "dimer" (i.e., two peptide subunits only), both the at least one first and the at least one second peptide monomers used and the resulting oligopeptide are active against at least one pathogen. A "trimer" in accordance with the present invention need not include only peptide subunits which are active against at least one pathogen. For example, one of the terminal peptide monomers or the monomer in the middle of a trimeric oligopeptide in accordance with the present invention may exhibit no antimicrobial activity so long as the two remaining monomers are active against at least one pathogen and the resulting trimer is also active against at least one pathogen.

The oligopeptides in accordance with the present invention may take a surprising number of forms. However, for simplicity, the oligopeptides of the present invention may be best conceptualized as dimers; oligopeptides composed of two peptide units with or without an intervening bridge. The simplest of these is a so-called "head-to-tail" oligopeptide comprising at least one first peptide monomer and at least one second peptide monomer. Each peptide monomer has an N-terminus (amino terminus) and a C-terminus (carboxyl terminus), both of which are capable of forming peptide bonds. In the head-to-tail configuration, the C-terminal amino acid of the at least one first peptide monomer is directly bound to the N-terminus of the at least one second peptide monomer, by a peptide bond, without any intervening bridging group. Examples of this type of "head-to-tail" peptide are oligopeptides having the structure: (SEQ ID NO. 2)-(SEQ ID NO. 2); (SEQ ID NO. 2)-(SEQ ID NO. 3) wherein Xaa$^5$ is Phe, Xaa$^6$ is Leu, Xaa$^7$ is His, Xaa$^8$ is Glu, Xaa$^{10}$ is Gly, Xaa$^{11}$ is Lys, Xaa$^{12}$ is Phe, Xaa$^{13}$ is Gly, Xaa$^{18}$ is Gly, Xaa$^{19}$ is Glu, Xaa$^{21}$ is Met, Xaa$^{22}$ is Lys and Xaa$^{23}$ is Pro; (SEQ ID NO. 10)-(SEQ ID NO. 2); (SEQ ID NO. 1)-(SEQ ID NO. 14); (SEQ ID NO. 13)-(SEQ ID NO. 9); (SEQ ID NO. 10)-(SEQ ID NO. 10); and (SEQ ID NO. 6)-(SEQ ID NO. 9). In all of the foregoing examples the dash represents a direct peptide bond between the C-terminal amino acid of the peptide monomer on the left of the dash and the N-terminal amino acid of the peptide monomer on the right of the dash. As will be readily apparent from the examples provided above, the oligopeptides of the present invention may be constructed from identical peptide monomers each of which are active against plant pathogens, peptide monomers whose base structures are similar but which are substituted relative to each other, RAMPPPS, and/or peptide monomers whose structure and origin are dramatically different.

Another type of oligopeptide in accordance with the present invention is the so-called "bridged" oligopeptide. In one embodiment these oligopeptides comprise at least one first and at least one second peptide monomer as previously described. However, in addition, at least one bridge is provided which comprises at least one amino acid. The bridge has an N-terminus and a C-terminus. When joined, the bridged oligopeptides of the present invention have the C-terminus of the at least one first peptide monomer peptide bound directly to the N-terminus of the bridge and the C-terminus of the bridge is then directly peptide bound to the N-terminus of the at least one second peptide monomer. Examples of such oligopeptides include: (SEQ ID NO. 2)-(SEQ ID NO. 5)-(SEQ ID NO. 2); (SEQ ID NO. 2)-(SEQ ID NO. 5)-(SEQ ID NO. 3) wherein $Xaa^5$ is Phe, $Xaa^6$ is Leu, $Xaa^7$ is His, $Xaa^8$ is Glu, $Xaa^{10}$ is Gly, $Xaa^{11}$ is Lys, $Xaa^{12}$ is Phe, $Xaa^{13}$ is Gly, $Xaa^{18}$ is Gly, $Xaa^{19}$ is Glu, $Xaa^{21}$ is Met, $Xaa^{22}$ is Lys and $Xaa^{23}$ is Pro; (SEQ ID NO. 10)-(SEQ ID NO. 5)-(SEQ ID NO. 2); (SEQ ID NO. 9)-(SEQ ID NO. 5)-(SEQ ID NO. 14); and (SEQ ID NO. 1)-(SEQ ID NO. 5)-(SEQ ID NO. 14). In all of the above examples, a preferred five-membered bridge (SEQ ID NO. 5) is used in which all five of the amino acids contained within the bridge are Gly. Other bridges such as, for example, omega loops or other structures of preferably 100 amino acids or less in length, and more preferably 20 amino acids or less in length are also useful.

In accordance with another aspect of this invention, the bridge may constitute as few as one amino acid. In such cases, exemplary oligopeptides have the structures: (SEQ ID NO. 2)-Ala-(SEQ ID NO. 2); (SEQ ID NO. 2)-Gly-(SEQ ID NO. 20); (SEQ ID NO. 10)-Ala-(SEQ ID NO. 2); (SEQ ID NO. 9)-Gly-(SEQ ID NO. 14); (SEQ ID NO. 9)-Gly-(SEQ ID NO. 9); and (SEQ ID NO. 1)-Ala-(SEQ ID NO. 14).

It is not necessary, however, that the oligopeptides of the present invention be joined by peptide bonds. In fact, they may be joined by a disulfide linkage. Thus, in accordance with another aspect of the present invention, an oligopeptide includes at least one first peptide monomer and at least one second peptide monomer, each of which include an N-terminus and a C-terminus. The at least one first peptide monomer and the at least one second peptide monomer are then joined by a disulfide bond.

The resulting oligopeptide may be in a "head-to-tail" configuration whereby the C-terminus of the at least one first peptide is a Cys and is joined to the Cys at the N-terminus of the at least one second peptide by a disulfide bond. These oligopeptides may also be joined in a "head-to-head" or "tail-to-tail" configuration as described herein. Alternatively, the oligopeptides in accordance with this aspect may be joined such that at least one of the peptide monomers is not bound at its terminus to the oligopeptide. Rather, the oligopeptide in accordance with this aspect of the present invention uses at least one peptide monomer which is substituted, other than at its termini, with a Cys. This Cys then forms a disulfide bond with either the Cys substituted or appended to the N or C terminus of a second peptide monomer, the N or C terminus of a bridge which has been substituted or appended with a Cys, or with the Cys substituted at other than the termini of a second peptide monomer.

The at least one first and one second peptide monomers useful in accordance with a "head-to-tail" embodiment of the present invention may have an additional Cys peptide bound to one of their termini, e.g., (SEQ ID NO. 1)-Cys, or have a Cys substituted at one termini, e.g., (SEQ ID NO. 3) wherein $Xaa^5$ is Phe, $Xaa^6$ is Leu, $Xaa^7$ is Arg, $Xaa^8$ is Ser, $Xaa^{10}$ is Gly, $Xaa^{11}$ is Lys, $Xaa^{12}$ is Phe, $Xaa^{13}$ is Gly, $Xaa^{18}$ is Gly $Xaa^{19}$ is Glu, $Xaa^{21}$ is Met, $Xaa^{22}$ is Lys and $Xaa^{23}$ is Cys. If these two peptide monomers were attached via a disulfide linkage between the Cys amino acids at the C-terminus of each, the resulting structure could be illustrated as (SEQ ID NO. 1)-Cys-S-S-(SEQ ID NO. 3)*, wherein -S-S- indicates the oxidized disulfide linkage between two Cys and "*" indicates that this peptide is inverted such that its C-terminus faces the C-terminus of the other peptide and, in this instance, wherein the same peptide as indicated by "*" is a multiple residue substitution of Magainin 1 having a Cys at the C-terminus. This is an example of a "tail-to-tail" configuration. A "head-to-head" configuration can be obtained by substituting or appending a Cys at the N-terminus of two peptide monomers and subsequently attaching the monomers by a disulfide linkage. An example of a peptide monomer having a Cys appended to the N-terminus is a peptide having the structure of Cys-(SEQ ID NO. 20) wherein the His in position 7 of Magainim 1 (SEQ ID NO. 1)is replaced with an Arg, the Ser in position 8 is substituted with a Glu, and the Ser at position 23 is substituted with a Pro, (SEQ ID NO. 20) and where a Cys is peptide bound to the Gly in position 1.

A "head-to-tail" oligopeptide in accordance with this aspect of the present invention could be obtained by forming a disulfide bond between a peptide monomer of the structure (SEQ ID NO.1)-Cys and a second peptide monomer which is a single residue N terminal additional derivative of (SEQ ID NO.20) where in the N-terminal addition is Cys. The resulting structure would be (SEQ ID NO.1)-Cys-S-S-Cys-(SEQ ID NO.20).

The present inventors have additionally found that disulfide-linked oligopeptides in accordance with the present invention may also be made using at least one peptide monomer which is, for example, an AMPPP substituted other than at its terminus with one amino acid Cys. The simplest form of the resulting oligopeptide can be illustrated by an oligopeptide having the structure (SEQ ID NO. 2)-Cys-S-S-(SEQ ID NO. 1) wherein, for example, the His normally found at position $Xaa^7$ in the peptide (SEQ ID NO. 1) is replaced with the amino acid Cys. The disulfide link is then formed between the Cys's on both peptide monomers.

Any of the foregoing may be combined as desired and the resulting oligopeptide may stretch for a considerable number of repeating units. For example, oligopeptides in accordance with the present invention could have the structure (SEQ ID NO. 1) peptide bound at its C-terminal Ser directly to the N-terminus of a second peptide having the structure of (SEQ ID NO. 2) which is itself peptide bound at its C-terminal Ser to a bridge having a single amino acid (Ala), the Ala being attached to the N-terminus of a third peptide having the structure of (SEQ ID NO. 6), and the C-terminus of this third peptide is directly bound to the N-terminus of a fourth peptide having a structure of (SEQ ID NO. 12) wherein $Xaa^1$=Ser, $Xaa^2$=Lys, $Xaa^6$=Gly, $Xaa^{11}$=Ala, $Xaa^{14}$=Gly, $Xaa^{16}$=Glu, and $Xaa^{17}$=Arg. The resulting exemplary peptide may be represented as: (SEQ ID NO. 1)-(SEQ ID NO. 2 )-Ala-(SEQ ID NO. 6)-(SEQ ID NO. 12). Another exemplary oligopeptide in accordance with the present invention has the structure: (SEQ ID NO. 6)-(SEQ ID NO. 1)-Gly-(SEQ ID NO. 2)-(SEQ ID NO. 2)-(SEQ ID NO. 15)-(SEQ ID NO. 14)-Cys-S-S-(SEQ ID NO. 3)**,*, wherein the peptide monomer designated with "*" is inverted such that its C-terminus is to the left in order in this structure, ("tail-to-tail" configuration), wherein Xaa$^{23}$ of (SEQ ID NO. 3)** is substituted with a Cys, wherein (SEQ ID NO. 3) has Xaa$^5$=Phe, Xaa$^6$=Leu, Xaa$^7$=His, Xaa$^8$=Glu, Xaa$^{10}$=His, Xaa$^{11}$=Lys, Xaa$^{12}$=Phe, Xaa$^{13}$=Gly, Xaa$^{18}$=Gly, Xaa$^{19}$= Glu, Xaa$^{21}$=Met, Xaa$^{22}$=Lys, and Xaa$^{23}$=Ser, and wherein "-S-S-" represents a disulfide bond. Other exemplary oligopeptides include: (SEQ ID NO. 20)-Cys-S-S-Cys-(SEQ ID NO. 10)-(SEQ ID NO. 5)-(SEQ ID NO. 1)-(SEQ ID NO. 1)-(SEQ ID NO. 2) wherein Xaa$^1$ through Xaa$^5$ of (SEQ ID NO. 5) are Gly; (SEQ ID NO. 6)-(SEQ ID NO. 7)-(SEQ ID NO. 4)-(SEQ ID NO. 20)-Cys-S-S-Cys-(SEQ ID NO. 20)*-(SEQ ID NO. 4)*-(SEQ ID NO. 7)*-(SEQ ID NO. 6)* wherein Xaa$^1$-Xaa$^4$ of (SEQ ID NO. 4) and (SEQ ID NO. 4)* are Gly; and Met (SEQ ID NO. 10)-Cys-S-S-(SEQ ID NO. 2) wherein the His in position 7 of (SEQ ID NO. 2) is substituted with an Arg.

In another embodiment in accordance with this aspect of the present invention, various forms of bridges may be combined with a disulfide linkage to produce a composite bridging molecule. The resulting oligopeptides are essentially the same as the disulfide linked oligopeptides described herein, however, they further include a bridge which separates one or more of the peptide subunits from the disulfide bond. One example of such a structure is the oligopeptide having the structure of (SEQ ID NO. 1)-(SEQ ID NO. 5)-Cys-S-S-Cys-(SEQ ID NO. 2) wherein Xaa$^1$-Xaa$^5$ of (SEQ ID NO. 5) are Gly. If the resulting oligopeptide is "head-to-tail", then the residue of (SEQ ID NO. 2) attached to the Cys is Gly. If the resulting oligopeptide is "tail-to-tail" then the residue attached to the Cys is Ser and the peptide structure to the right of the disulfide linkage would be designated as (SEQ ID NO. 2)*. In this oligopeptide, a bridge of five Gly residues provides additional space to allow for further flexibility and intermonomer interaction while at the same time providing for the ability to attach various monomers via a disulfide linkage. In a more preferred aspect of this invention, the composite bridge would have the structure (SEQ ID NO. 5)-Cys-S-S-Cys-Ala- wherei Xaa$^1$-Xaa$^5$ of (SEQ ID NO. 5) are Gly. This structure uses a composite bridge which includes two bridges separated by a disulfide linkage.

In another embodiment, the combination of a bridge and a disulfide linkage can be used to provide for unique oligopeptides. In accordance with this aspect of the present invention, a bridged oligopeptide as described herein contains either two peptide monomers, or one peptide monomer and a bridge, which are substituted with a single Cys or the bridge contains two Cys. A disulfide linkage may then be formed between the Cys amino acids such that the disulfide linkage also traverses one of the peptide bonds which join the Cys-containing monomer to the bridge or which is wholly in the bridge.

One such resulting oligopeptide may have the exemplary structure (SEQ ID NO. 1)-(SEQ ID NO. 4)-(SEQ ID NO. 2) wherein the amino acid Met normally found at position 21 of the peptide having a structure of (SEQ ID NO. 1) is substituted with a Cys and in (SEQ ID NO. 4) Xaa$^1$ is Gly, Xaa$^2$ is Cys, Xaa$^3$ is Gly, and Xaa$^4$ is Gly and wherein a disulfide linkage is formed between the two Cys amino acids. Similarly, a resulting exemplary oligopeptide may have a structure of (SEQ ID NO. 1)-(SEQ ID NO. 4)-(SEQ ID NO. 2) wherein the amino acid Met normally found at position 21 of the peptide having a structure of (SEQ ID NO. 1) is substituted with a Cys, and in (SEQ ID NO. 4) Xaa$^1$-Xaa$^4$ are Gly and wherein the amino acid Ile normally found at position 2 of the peptide having a structure of (SEQ ID NO. 2) is substituted with a Cys and wherein a disulfide bond is formed between the two Cys amino acids. Still another exemplary oligopeptide may have the structure of (SEQ ID NO. 1)-(SEQ ID NO. 15)-(SEQ ID NO. 2) wherein for (SEQ ID NO. 4) Xaa$^1$ is Cys, Xaa$^2$ is Gly, Xaa$^3$ is Pro and Xaa$^4$ is Cys and wherein a disulfide linkage is formed between the two Cys contained within the bridge. See Mutter, "The Construction of New Proteins and Enzymes—A Prospect for the Future?" *Argew. Chem. Int. Ed. Engl.*, 24, (1985), 639–653.

In accordance with another aspect of the present invention there are provided oligopeptides which have appended a signal peptide to their N-terminus which may thereby facilitate the transport of the oligopeptides discussed and described herein from the ribosomal sites of oligopeptide production to the extracellular space between cells such that the resulting oligopeptides may be more effective in providing protection against invasion by at least one microbial pathogen.

The present invention also includes techniques for the use of the oligopeptides provided herein to protect organisms, and preferably plants, from detrimental effects of the attack, colonization or infestation of pathogenic microorganisms.

Another object of the present invention is the provision of compounds with enhanced activity against pathogens including plant pathogens.

It is also an object of the present invention to provide for a composition which exhibits a broader range of potential microbial protection than could be provided by any single member of its components.

In accordance with this aspect of the present invention there are provided novel compounds which involve mixtures of two or more discrete antimicrobial peptides. One such antimicrobial composition includes at least one first antimicrobial peptide which is relatively active against one group of pathogens and relatively inactive against another group of pathogens and at least one second antimicrobial peptide which is relatively active against the group of pathogens which the at least one first antimicrobial peptide is relatively inactive against and relatively inactive against the group of pathogens which the at least one first antimicrobial peptide is relatively active against.

Applicants have discovered that, in modifying Magainins 1 and 2 in accordance with the aforementioned Bascomb, et al. application, to provide for specific antimicrobial activity, resistance to proteolytic degradation and/or reduction of the phytotoxicity of a peptide, certain sacrifices in the activity of peptides structurally related to magainins sometimes results. Thus, for example, a resulting peptide may have reduced phytotoxicity or enhanced resistance to proteolytic degradation, or both, and still may be active against a particular pathogen or particular class of pathogens. Often, however, these improved peptides lose substantial activity against other pathogens. For example, the present inventors have found that by amending Magainin 2 having the structure of (SEQ ID NO. 2) by substituting the Ser at position 8 with a Glu, the resulting peptide has a substantial reduction in phytotoxicity and a substantial reduction in the extent of proteolysis. The minimum complete inhibitory concentration necessary to inhibit the growth of plant pathogenic fungi such as P3 Fusarium is only elevated from 20–25 ug/mL to 40 ug/mL. However, the minimum complete inhibitory concentration of the composition necessary to provide protection against plant pathogenic bacteria such as *Erwinia carotovora carotovora* rises from about 40 to 50 ug/mL to greater than 150 ug/mL. Obviously, this composition has great promise because of its reduced phytotoxicity and proteolytic sensitivity. However, its use is somewhat compromised by its inactivity against a significant class of other plant pathogens (i.e., bacterial pathogens).

The inventors have discovered that other peptides exhibit a corresponding but complementary behavior with regard to plant pathogens. For example, the inventors have discovered P1 (SEQ ID NO. 6), unlike the above-mentioned Magainin 2 derivatives, is very active against *Erwinia cartovora carotovora* but relatively inactive against P3 Fusarium. Mixtures of two or more of such complementary peptides can provide a broad spectrum of protection which cannot be realized by lo the use of one antimicrobial peptide alone. Additionally, these peptides do not threaten the viability of plant cell hosts and do not suffer from an unnecessarily short life span in the presence of at least one plant protease. These compounds can be provided as a mixture having broad spectrum activity against plant pathogenic fungi and bacteria, while at the same time having reduced phytotoxicity and increased overall resistance to proteolysis. These mixtures could be provided by producing, collecting and intermixing two or more antimicrobial peptides and/or by engineering a synthetic gene or genes to co-express these peptides in transformed host cells. Additionally, these peptides may be linked to form an oligopeptide as described herein and could be subsequently cleaved by proteolytic enzymes contained within, for example, a plant. This would result in the in situ formation of a mixture of the two complementary antimicrobial peptides.

Another object of the present invention is to provide a method of conveniently screening antimicrobial peptides to determine their relative toxicity.

In accordance with one aspect of the present invention, there is provided a method for screening antimicrobial peptides to determine their relative toxicity which includes the steps of intermixing at least one antimicrobial peptide and a solution containing cultured whole cells, and determining the change in oxygen consumption by the cultured whole cells. The rate of suppression of oxygen consumed by the cultured whole cells is indicative of the relative toxicity of the peptide against both the cultured cells and cells in general.

In one preferred embodiment in accordance with this method of screening, cultured whole plant cells are used. In another preferred aspect of this invention, the plant cells are protoplasts.

BRIEF DESCRIPTION OF THE DRAWING

Preferred embodiments of the present invention are described in greater detail with reference to the accompanying drawing wherein:

FIG. 1 is a table containing preferred peptides, peptide monomers, and bridges, as well as oligonucleotides, all of which are repeated in conventional single letter format.

DETAILED DESCRIPTION OF THE PREFERRED EMBODIMENT PEPTIDES

The various peptides used in accordance with the present invention are antimicrobial peptides which are active against at least one microbial pathogen. However, preferred peptides in accordance with the present invention may be represented by the term "AMPPP" which is an acronym for Antimicrobial Peptide Active Against Plant Pathogen which, as defined herein, is a protein or peptide having at least antifungal and/or antibacterial activity against a plant pathogen.

Those antimicrobial peptides and, in particular, AMPPP compositions which are preferred for the purposes of the present invention are those which meet at least some of a multiplicity of criteria. A primary criterion for peptides and oligopeptides in accordance with the present invention is activity against one or more pathogens and, in particular, plant pathogens. That is, these peptides are preferably effective in retarding the growth of and/or limiting the survival of plant pathogens. The term "plant pathogens" encompasses those organisms that can cause damage and/or disease to plants, and includes fungi, procaryotes (bacteria and mycoplasma), viruses and viroids, nematodes, protozoa, and the like.

For example, there are more than 8,000 species of fungi that can cause plant disease. See, *Plant Pathology*, Third ed., George N. Agrios, Academic Press, Inc., 1988; *A Literature Guide for Identification of Plant Pathogenic Bacteria*, A. Y. Rossman et al., American Pathological Society, St. Paul, Minn., 1988; *The Laboratory Guide for Identification of Plant Pathogenic Bacteria*, N. W. Schad, Ed., American Phytopathological Society, St. Paul, Minn., 1980. In recognition of the extensive array of such pathogens, the most useful AMPPPs within the context of one aspect of the present invention are those which have a broad spectrum of activity, inhibiting or retarding the growth or survival of numerous plant pathogens, or which are very effective against specific groups of pathogens, especially groups which cause diseases in many crops. For example, Erwinia species are responsible for a variety of soft rot and wilt diseases that cost farmers hundreds of millions of dollars annually. One or more AMPPPs which could control the survival or proliferation of Erwinia species would therefore be desirable. More desirable, however, are AMPPPs which would also provide some measure of activity against species of fungi and/or against other classes of pathogens which may combine to attack a specific host. Examples of such a condition are stalk rots in maize that are caused by different combinations of several species of fungi and bacteria (e.g. Fusarium spp, Gibberella spp, Diplodia spp, Macrophomina spp, Pythium spp, Cephalosporium spp, Erwinia spp, Pseudomonas spp). Other examples include conditions where damaged tissues are invaded by saprophytic organisms as in postharvest diseases of plant products.

A number of symbiotic or benign microorganisms, which are mainly bacterial species, are found associated with plants. Useful AMPPPs would be those which do not have an effect on the survival of these microorganisms while exhibiting effective control of one or more distinct plant pathogens. Therefore, in some situations, a degree of specificity is beneficial. For example, when protection of a root system is desirable, it would be beneficial to leave intact organisms such as Rhizobium spp, which fix atmospheric nitrogen, or root colonizing organisms such as Pseudomonas spp, that serve to protect the roots from certain pathogens. Since many of these beneficial or benign organisms are bacteria, there is a specific utility for AMPPPs that have diminished activity against bacteria.

While the term may have broader application to one or more entire families of antimicrobial peptides, antimicrobial peptides active against at least one pathogen and the term AMPP encompass: Magainin 1; Magainin 2; reverse magainins; P1 and reverse P1; $PGL^c$ and reverse $PGL^c$; Cecropins including Cecropins A, B, and D and their reverse peptides, see H. G. Boman et al., "On the Primary Structures of Lysozymers, Cecropins, and Attacins from *Hyalophora cecropia,*" *Developmental and Comparative Immunology*, 9, (1985), 551–558; Sarcotoxins and their reverse peptides; Bombinins and their reverse peptides, see A. Csordas and H. Michl, "Isolierung und Strukturaufklarung eines Hamolytisch wirkenden Polypeptides aus dem Abwehrsekret europaischer Unken," *Monat fur Chemie,* 101, (1970), 182–189; XPF and its reverse peptide; Thionins and their reverse peptides; Defensins and their reverse peptides, see H. Vogel et al., "The Structure of Melittin in Membranes," *Biophys. J.,* 50, (1986), 573–582; Melittins and their reverse peptides, see H. Vogel et al., "The Structure of Melittin in Membranes," *Biophys. J.,* 50, (1986), 573–582; and other equivalent peptides and functional derivatives thereof.

The term "functional derivative" as used herein includes single residue omission derivatives, multiple residue omission derivatives, single residue substitution derivatives, multiple residue substitution derivatives, single residue terminal addition derivatives, and C-terminal amides of the peptides.

The term "single residue omission derivative" shall be understood to mean a particular peptide having a structure which is otherwise identical to or related to a specifically enumerated peptide but having one of its residues omitted. For example, [Des Met 21] MAG 1 is a peptide whose structure is identical to that of Magainin 1 represented by (SEQ ID NO. 1). However, the Met which is normally found in the 21st position relative to the N-terminal Gly has been deleted. ("Des" indicates a deletion, "Met" indicates the amino acid deleted, "21" indicates the position that the deleted Met would occupy on the naturally occurring peptide, and "MAG 1" indicates the peptide so modified (Magainin 1)). The resulting 22 amino acid peptide is a single residue omission derivative as defined herein. Similarly, the term "multiple residue omission derivative" contemplates a peptide where more than one amino acid has been deleted from the otherwise identical or related sequence. For example, [Des(Lys 22, Ser 23)] MAG 1 is a peptide whose structure is identical to Magainin 1 represented herein by (SEQ ID NO. 1). However, the C-terminal Ser in position 23 and the next adjacent amino acid Lys in position 22 are both omitted. The resulting 21 amino acid peptide is a multiple residue omission derivative in accordance with the present invention and is more specifically a double residue omission derivative.

The term "single residue substitution derivative" in accordance with the present invention includes peptides which are identical to the structure of an otherwise identical or related compound with the exception that a single residue has been changed. For example [Glu 8] MAG 2 is a peptide which is identical to Magainin 2 which is represented herein by (SEQ ID NO. 2). However, the Ser which is normally found in position 8 of Magainin 2 has been replaced or substituted with Glu. The resulting 23 amino acid peptide is a single residue substitution derivative in accordance with the present invention. The term "single residue substitution derivative" in accordance with the present invention also encompasses a group of peptides which are internally substituted (i.e., not at the terminus or appended thereto) with a single Cys amino acid. Examples of such a compound are [Cys 22] Mag 2, [Cys 8] Mag 1, [Cys 8] Mag 2, and the like.

Similarly, a "multiple residue substitution derivative" in accordance with the present invention contemplates a peptide which is identical to an enumerated or a related peptide with the exception that a number of substitutions have been made. For example [Ala 13, 18] MAG 1 is a peptide which is identical to Magainin 1 represented herein by (SEQ ID NO. 1). However, the Gly which are normally found in positions 13 and 18 of Magainin 1 have been replaced with Ala. Similarly, [Arg 7, Glu 8, Pro 23] MAG 1 (SEQ ID NO. 20) is a peptide which is identical to Magainin 1 except that the His in position 7 has been replaced or substituted with Arg, the Ser at position 8 has been replaced with Glu and the Ser in position 23 has been substituted with Pro. The resulting peptides are multiple residue substitution derivatives. Another peptide of this type is [Arg 7, Cys 8] MAG 1. These derivatives are not exclusive modifications. Thus it is possible that a peptide is both a substitution and an omission derivative. For example [Des Gly 1, Met 2] MAG 2 is a peptide which is identical in structure to Magainin 2 having (SEQ ID NO. 2). However, the N-terminal Gly has been deleted and the Ile normally found in position 2 relative to the N-terminal Gly has been replaced or substituted with the amino acid Met. The resulting peptide is both a single residue omission derivative and a single residue substitution derivative in accordance with the present invention.

While not wishing to be limited to any particular omission or substitution, some of the more preferable substitutions for peptides which are structurally similar to the magainins are represented herein by the peptide having the structure of (SEQ ID NO. 3). "Xaa" as used in this sequence indicates a variable such that any of a select group of amino acids can be positioned therein. Furthermore, "Xaa$^n$" is used to represent not only the variable, but also to describe the relative position of that variable or the amino acids which that variable represents (i.e., "n" represents the position, or the amino acid in the nth position). Thus, Xaa$^6$ represents the variable in the 6th position of the AMPPP having the structure of (SEQ ID NO. 3). The "n"th position is relative to the N-terminal end of the peptide which, for these peptides, is usually Glycine (Gly). When the aforementioned peptide further includes a single residue N-terminal addition, such as methionine (Met) or N-formylated Met "(f)Met," Cys His or Ser, attached through a peptide bond to the N-terminal amono acid (usually Gly) of the peptide having the structure of (SEQ ID NO. 3) the variable Xaa$^6$ retains its nomenclature and its position relative to the N-terminal Glycine. This is despite the fact that, in an absolute sense, the 6th position is now the 7th residue in the resulting peptide. Similarly, if the N-terminal Gly were omitted, such that the variable Xaa$^6$ was the 5th residue in the resultant peptide, the variable will nonetheless remain designated Xaa$^6$, (i.e., for IleGlyLysPheXaa . . . , Xaa is still Xaa$^6$). When placed in such terms, Magainin 1 could alternatively be represented as a peptide having the structure of (SEQ ID NO. 3) wherein Xaa$^5$ is Phe, Xaa$^6$ is Leu, Xaa$^7$ is His, Xaa$^8$ is Ser, Xaa$^{10}$ is Gly, Xaa$^{11}$ is Lys, Xaa$^{12}$ is Phe, Xaa$^{13}$ and Xaa$^{18}$ are Gly, Xaa$^{19}$ is Glu, Xaa$^{21}$ is Met, Xaa$^{22}$ is Lys, and Xaa$^{23}$ is Ser. Magainin 2 is structurally similar to Magainin 1 except that Xaa$^{10}$ is Lys and Xaa$^{22}$ is Asn.

With reference to FIG. 1, some of the preferred peptides in accordance with the present invention are depicted in single letter format. "X" as used in that format is a variable and is identical to "Xaa" as described above. Thus, the fifth letter in line 3, (GIGKX . . . ) of FIG. 1 equates to Xaa$^5$ and may be substituted with the same amino acids as Xaa$^5$. The "NH$_2$" of the C-terminus of line 8 represents the C-terminal amide form of the peptide recited thereby.

One of the advantages of such modifications could be the production of antimicrobial peptides, and, in particular, AMPPPs which exhibit or show improved activity against pathogens.

Another basis for selecting preferred peptide compositions in accordance with the present invention and indeed for selecting specific modifications, is resistance to digestion or degradation by one or more proteases and, in particular, one or more plant protease or plant pathogen proteases. Plants contain enzymes which are used to degrade proteins within a cell, within a subcellular organelle, within a compartment, or within the extracellular space between cells. These enzymes, also known as proteases, degrade proteins and peptides by breaking specific bonds linking amino acid sequences and producing inactive or less active fragments. Plant pathogens also produce and, in many instances, secrete proteases that could degrade and potentially inactivate antimicrobial peptides or proteins. In the context of the present invention, this natural phenomenon can be disastrous because it can deactivate the AMPPPs which may otherwise protect a plant by retarding plant pathogens. This problem presents itself for both topically applied AMPPPs which are exposed to proteases contained within the extracellular spaces and expressed AMPPPs which are exposed to intracellular or extracellular proteases.

Post-translational cleavage of the $Xaa^{10}$–$Xaa^{11}$ position in natural magainins is caused naturally by proteases native to the exudates of the skin of Xenopus laevis, indicating that this site is available to proteases for digestion. See *M. G. Giovannini* et al., supra.

At least some amino acid substitutions and/or deletions at sites adjacent to peptide bonds which can be characterized as sensitive to one or more plant proteases should reduce or eliminate proteolysis. This may be due, at least in part, to inhibition of the action of the respective plant protease or proteases through induction of a poor "fit" between the protease enzyme and the AMPPP substrate cleavage site.

It has been unexpectedly found that plant proteolytic degradation due to treatment of AMPPPs with plant extracellular fluid containing plant proteases occurs by cleavage of the bonds between His and Ser at positions 7 and 8, respectively, of Magainin 1 and Magainin 2, and Met and Asn or Met and Lys at positions 21 and 22 of Magainin 2 and Magainin 1 respectively. In recognition of these phenomena, specific substitutions have been discovered at one or more of these positions which are effective in greatly reducing adverse proteolytic degradation by plant proteases. The peptides so modified are therefore likely candidates for expression in transgenic plants as well as being useful for conventional application for crop protection. Substitutions at the foregoing positions which may be effective in reducing, if not eliminating adverse proteolytic degradation by plants and/or plant pathogen proteases, include Phe, Ala, Glu, Asp, Lys, Ser, or Arg at $Xaa^7$, Thr, Asp, Ala, His, or Glu at $Xaa^8$, Arg, Lys, His, Gln, Trp, Tyr, Thr, Val, Ala, Leu, Ile, Glu, Asp, or Phe at $Xaa^{21}$, Arg, His, Glu, Trp, Tyr, Thr, Ala, Cys, Lys, Gly, Asp, Asn, Pro, or Met at $Xaa^{22}$ and Pro, Leu, Cys, Val, Ile, or Trp at $Xaa^{23}$. The more preferred substitutions in accordance with this aspect of the present invention are Arg or Lys substitutions at $Xaa^7$ Glu substitutions at $Xaa^8$, and/or Pro at $Xaa^{23}$.

Any or all of the preferred amino acid substitutions at positions 7, 8, 21 or 22 and/or 23 in AMPPPs may be combined with other substitutions, deletions, and/or extensions in accordance with the present invention to provide a peptide which is not only resistant to proteolysis, but also one with increased activity against one or more plant pathogens, with selected activity against specific plant pathogens, and/or with low phytotoxicity.

The term "single residue terminal addition derivative" as used herein contemplates a peptide such as, for example, Magainin 1 having the structure of (SEQ ID NO. 1) to which has been added, by a peptide bond, a single additional residue at the C or N-terminus. Examples of such single residue terminal addition derivative are [Met] MAG 1 wherein the amino acid Met is peptide bound to the N-terminus of a Magainin 1 molecule, [(f)Met] MAG 1 wherein a formylated Met is peptide bound to the N-terminus of Magainin 1 and [Cys 24] MAG 1 wherein a Cys is peptide bound to the C-terminal Ser of Magainin 1. The term also encompasses other terminal additions such as the use of His or Ser attached to the N or C-terminus.

As suggested above, yet another basis for selecting preferred compositions to be used in the context of the present invention is relatively low cell toxicity or, in plants, phytotoxicity. Antimicrobial peptides in accordance with the present invention should exhibit relatively low toxicity to their host cells, or to tissue to which these peptides are applied. AMPPPs should preferably exhibit relatively minimal toxic behavior against plant cells or plant tissue. More particularly, modifications designed to increase antimicrobial activity or to increase resistance to protease degradation should not substantially increase phytotoxicity. Toxic behavior can be manifested by the death, reduced growth, reduced photofixation of atmospheric carbon, reduced assimilation of nutrients such as nitrogen or phosphorus, or reduced crop yield. Therefore, it is important to provide peptides which are functionally compatible with their host.

Some relative index of phytotoxicity is therefore preferred in comparing one AMPPP to another or to natural magainins or other natural antibiotic peptides or other natural or synthetic antibiotic compounds of actual or prospective commercial value. Such an index could be the possible effect of an AMPPP on inhibiting normal plant cell organelle function. Preferred indices are the inhibition of oxygen evolution or carbon fixation by isolated plant chloroplasts or oxygen respiration by isolated plant mitochondria, or oxygen consumption by living cells or tissues. These effects could be monitored by a variety of techniques and instruments available in the art such as a Warburg apparatus or, preferably, an oxygen electrode. See, "The Use of the Oxygen Electrode and Fluorescence Probes In Simple Measurements of Photosynthesis," D. Walker, 1987, Hansatech Ltd., Kings Lynn, Norfolk, England.

REVERSE PEPTIDES

The term "RAMPPs" is an acronym for Reverse Antimicrobial Peptide active against at least one Pathogen. "RAMPPPs" are a subset of RAMPPs and refer to Reverse Antimicrobial Peptides which are active against at least one Plant Pathogen. As previously discussed, it has been unexpectedly found that by reversing the sequence of certain antimicrobial peptides, RAMPPPs can be produced having significant benefits. Specifically RAMPPs and, in particular, RAMPPPs, appear to have antimicrobial activity against pathogens, and in particular at least one plant pathogen. Furthermore, by reversing the sequence of specific peptides, antimicrobial peptides may be obtained which do not suffer from some of the disadvantages of their normal, "forward" sequence counterparts.

In the context of RAMPPPs, for example, peptides may be obtained which do not suffer as extensively from proteolytic degradation by at least one plant protease and/or are not as phytotoxic as their "forward" sequence AMPPP counterpart. These peptides are therefore likely candidates for use in providing protection to plants from plant pathogenic fungi and/or bacteria.

In accordance with the present invention, RAMPPs can be produced which have the identical but reversed sequence of peptides including reverse Magainin 1 (SEQ ID NO. 9), reverse Magainin 2 (SEQ ID NO. 10), reverse P1 (SEQ ID NO. 13), reverse Cecropin A (SEQ ID NO. 14), as well as reverse PGL$^c$ (SEQ ID NO. 7), and reverse forms of other Cecropins, Sarcotoxins, Bombinins, XPF, Thionins, Defensins, Melittins, and like antimicrobial peptides.

RAMPPs in accordance with the present invention are not limited to reversing the peptide sequence of unsubstituted, naturally occurring antimicrobial peptides. Certain substitutions, modifications and/or omissions may be made where appropriate. For example, the reverse peptides having (SEQ ID NO. 11) are identical to but the exact reverse sequence of the peptides having the structure of (SEQ ID NO. 3); thus they are reverse peptides of compounds related to Magainins 1 and 2 structurally. These peptides include variables in positions $Xaa^1$–$Xaa^3$, $Xaa^5$, $Xaa^6$, $Xaa^{11}$–$Xaa^{14}$ and $Xaa^{16}$–$Xaa^{19}$ wherein $Xaa^1$, $Xaa^2$, $Xaa^3$, $Xaa^5$, $Xaa^6$, $Xaa^{11}$, $Xaa^{12}$, $Xaa^{13}$, $Xa^{14}$, $Xaa^{16}$, $Xaa^{17}$, $Xaa^{18}$, and $Xaa^{19}$ may be the same or different and are selected from the group consisting of Ala, Arg, Cys, Asn, Asp, Gln, Glu, Gly, His, Ile, Leu, Lys, Met, Phe, Pro, Ser, Thr, Trp, Tyr, and Val. Preferably, the peptides of (SEQ ID NO. 11) are RAMPPs structurally related to natural Magainin 1 and Magainin 2 wherein $Xaa^1$ and $Xaa^3$ may be the same or different and are amino acids selected from the group consisting of Arg, Asp, Cys, His, Glu, Lys, Gln, Tyr, Thr, Trp, Met, Ser, Ala, Phe, Val, Ile, Leu, and Pro, $Xaa^2$ is an amino acid selected from the group consisting of Arg, Asp, Cys, His, Glu, Lys, Gln, Tyr, Met, Asn, Ala, Pro, and Thr, $Xaa^5$ is an amino acid selected from the group consisting of Ala, Gln, Glu, His, Met and Trp, $Xaa^6$ is an amino acid selected from the group consisting of Trp, Tyr, Asp, Glu, Lys, Arg, Gln, His, Met, Ala, and Gly, $Xaa^{11}$ is an amino acid selected from the group consisting of Leu, Ile, Trp, Phe, Val, Ala and Gly, $Xaa^{12}$ is an amino acid selected from the group consisting of Phe, Ile, Trp, Leu, and Val, $Xaa^{13}$ is an amino acid selected from the group consisting of Met, Trp, Tyr, Gln, Lys, His, Pro, Ser and Arg, $Xaa^{14}$ is an amino acid selected from the group consisting of Gly, Leu, Ile, Val, Ala, Phe, Met, Thr, Ser, Trp, Tyr, Gln, Lys, Asn, Glu, His, Asp, and Arg, $Xaa^{16}$ is an amino acid selected from the group consisting of Ala, Met, Thr, Ser, Trp, Tyr, Gln, Lys, Asn, Glu, His, Asp and Arg, $Xaa^{17}$ is an amino acid selected from the group consisting of Phe, Ala, Met, Ser, Thr, Trp, Tyr, Gln, Lys, Asn, Glu, His, Asp and Arg, $Xaa^{18}$ is an amino acid selected from the group consisting of Asn, Ile, and Leu, and $Xaa^{19}$ is an amino acid selected from the group consisting of Phe, Ile, Leu, Trp and Val.

Other substituted RAMPPs in accordance with the present invention include the RAMPPs having the structure of (SEQ ID NO. 12) wherein $Xaa^1$ is an amino acid selected from the group consisting of Ser and Pro, $Xaa^2$ is an amino acid selected from the group consisting of Lys and Asn, $Xaa^6$ is an amino acid selected from the group consisting of Gly and Ala, $Xaa^{11}$ is an amino acid selected from the group consisting of Gly and Ala, $Xaa^{14}$ is an amino acid selected from the group consisting of Gly and Lys, $Xaa^{16}$ is an amino acid selected from the group consisting of Ser, Ala, Glu and Thr, and $Xaa^{17}$ is an amino acid selected from the group consisting of His, Lys, Arg and Phe. RAMPPs which have been substituted with a Cys at one of these positions, including other than at one of their termini, are also provided hereby.

RAMPPs, including the reverse antimicrobial peptides active against plant pathogens (RAMPPPs) of the present invention, may be made in accordance with the procedures discussed herein relating to the chemical and/or genetic synthesis of peptides generally. These peptides may also be incorporated within an oligopeptide in accordance with the present invention. Furthermore, it may be possible and, indeed advantageous to reverse the structure of an oligopeptide in accordance with the present invention, in its entirety. By doing so, it may be possible to realize benefits which are similar to those realized by reverse peptides. Furthermore, these reverse peptides may be used as described herein for protecting organisms, and particularly plants, against pathogens by topical application, injection, introduction into the root system of a plant, by incorporating a gene which will express these compounds within an organism and initiating their expression, and/or by like methods of delivery.

PEPTIDE MONOMERS

The peptides previously described, as well as others described herein, may be used in the construction of oligopeptides in accordance with the present invention. These oligopeptides are formed from a plurality of peptide subunits which can be conceptualized as peptide monomers used to construct a peptide polymer or co-polymer. As used herein the terms "peptide monomer" and "monomer" therefore refers to a peptide which is particularly useful for constructing an oligopeptide in accordance with the present invention.

One group of monomers in accordance with the present invention which are useful for constructing oligopeptides are the previously described RAMPPs and RAMPPPs such as reverse Magainin 1 (SEQ ID NO. 9), reverse Magainin 2 (SEQ ID NO. 10), reverse magainin compounds having a structure (SEQ ID NO. 12), reverse Cecropin A (SEQ ID NO. 14), reverse PGL$^c$ (SEQ ID NO. 15) and reverse P1 (SEQ ID NO. 13).

Other peptide monomers useful in accordance with the present invention are Magainin 1 having a structure of (SEQ ID NO. 1), Magainin 2 having a structure of (SEQ ID NO. 2), P1 having a structure of (SEQ ID NO. 6), PGL$^c$ having a structure of (SEQ ID NO. 7), Cecropins such as Cecropin A having a structure of (SEQ ID NO. 8), Sarcotoxins, Bombinins, XPF, Thionins, Defensins, Melittins, and like antimicrobial peptides.

The term "monomer" or "peptide monomer" may also be used to encompass peptides, which are not themselves antimicrobial but which enhance the antimicrobial activity of the resulting oligopeptide or provide some other benefit thereto. For example, these peptides may provide a particularly preferred conformation, alignment, resistance to a particular enzyme or other similar advantage.

In addition, the single residue omission derivatives, multiple residue omission derivatives, single residue substitution derivatives, multiple residue substitution derivatives, single residue terminal addition derivatives and, where appropriate, C-terminal amides of the peptides just described may also be used as monomers so long as the resulting peptide amide is used at the C-terminus of the resulting oligopeptide.

Particularly preferred single residue terminal addition derivatives useful as peptide monomers in accordance with the present invention are those including the addition of a Cys which is peptide bound to either the C or the N-terminus of a peptide in accordance with the present invention or peptide monomers including the addition of a Met or (f)Met which may be peptide bound to the N-terminus of any of the aforedescribed peptides. Other substitutions in accordance with this aspect of the present invention include Ser or His appended to either the N or C-terminus of these peptides.

Also of particular interest in accordance with the present invention are peptide monomers which are multiple substitution derivatives of a peptide having the structure (SEQ ID NO. 3) wherein $Xaa^5$, $Xaa^6$, $Xaa^7$, $Xaa^8$, $Xaa^{10}$, $Xaa^{11}$, $Xaa^{12}$, $Xaa^{13}$, $Xaa^{18}$, $Xaa^{19}$, $Xaa^{21}$, $Xaa^{22}$ and $Xaa^{23}$ are amino acids which may be the same or different and are selected from the group consisting of Ala, Arg, Cys, Asn, Asp, Gln, Glu, Gly, His, Ile, Leu, Lys, Met, Phe, Pro, Ser, Thr, Trp, Tyr and Val. Preferably, these variables are selected from amino acids of the group consisting of Ala, Arg, Asn, Asp, Gln, Glu, Gly, His, Ile, Leu, Lys, Met, Phe, Ser, Thr, Trp, Tyr and Val. More preferably, peptide monomers in accordance with the present invention include peptides having the structure of (SEQ ID NO. 3) wherein $Xaa^5$ is an amino acid selected from the group consisting of Phe, Ile, Leu, Trp, and Val, $Xaa^6$ is an amino acid selected from the group consisting of Asn, Ile, and Leu, $Xaa^7$ is an amino acid selected from the group consisting of Phe, Ala, Met, Ser, Thr, Trp, Tyr, Gln, Lys, Asn, Glu, His, Asp, and Arg, $Xaa^8$ is an amino acid selected from the group consisting of Ala, Met, Thr, Ser, Trp, Tyr, Gln, Lys, Asn, Glu, His, Asp, and Arg, $Xaa^{10}$ is an amino acid selected from the group consisting of Gly, Leu, Ile, Val, Ala, Phe, Met, Thr, Ser, Trp, Tyr, Gln, Lys, Asn, Glu, His, Asp, and Arg, $Xaa^{11}$ is an amino acid selected from the group consisting of Met, Trp, Tyr, Gln, Lys, His, Pro, Ser, and Arg, $Xaa^{12}$ is an amino acid selected from the group consisting of Phe, Ile, Leu, Trp, Val, $Xaa^{13}$ is an amino acid selected from the group consisting of Leu, Ile, Trp, Phe, Val, Ala, and Gly, $Xaa^{18}$ is an amino acid selected from the group consisting of Thr, Trp, Tyr, Asp, Glu, Lys, Arg, Gln, His, Met, Ala, and Gly, $Xaa^{19}$ is an amino acid selected from the group consisting of Ala, Gln, Glu, His, Met, and Trp, $Xaa^{21}$ and $Xaa^{23}$ may be the same or different and are selected from the group consisting of Arg, Asp, Cys, His, Glu, Lys, Gln, Tyr, Thr, Trp, Met, Ser, Ala, Phe, Val, Ile, Leu, and Pro, and $Xaa^{22}$ is an amino acid selected from the group consisting of Arg, Asp, Cys, His, Glu, Lys, Gln, Tyr, Met, Asn, Ala, Pro, and Thr are used.

Other peptide monomers which may be useful in accordance with the present invention are those which are themselves resistant to degradation by at least one plant protease. One such monomer is P1. The present inventors have discovered that P1 is an AMPPP. That is to say, the present inventors have discovered that P1 is a compound which has activity against at least one microbial plant pathogen. Specifically, the present inventors have found that P1 is highly active against plant pathogenic bacteria such as *Erwinia carotovora carotovora*. The present inventors have also found that P1 possesses significant resistance to degradation by naturally occurring plant protease and possesses acceptable levels of phytotoxicity. Although P1 has been reported as a cecropin, other classifications are appropriate because of its origin (pig intestine instead of insects) and its differing structure. For simplicity, the present inventors have chosen to refer to this compound merely by the designation P1. See Lee et al. "Antibacterial Peptides from Pig Intestines: Isolation of a Mammalian Cecropin", *Proc. Natl. Acad. Sci.* (USA), 86, (1989)9159–9162.

Other peptide monomers which are resistant to plant proteases include the RAMPPs and RAMPPPs in accordance with the present invention as well as the peptides having the structure of (SEQ ID NO. 3) wherein at least one of the groups selected from $Xaa^7$, $Xaa^8$, $Xaa^{21}$, $Xaa^{22}$ and $Xaa^{23}$ are substituted. Preferably, $Xaa^7$ is an amino acid selected from the group consisting of Phe, Ala, His, Lys, Glu, Asp, Ser and Arg, $Xaa^8$ is an amino acid selected from the group consisting of Thr, Asp, Ser, Ala, His and Glu, $Xaa^{21}$ is an amino acid selected from the group consisting of Arg, Lys, His, Gln, Trp, Tyr, Thr, Ala, Leu, Ile, Val, Phe, Glu, Asp and Met, $Xaa^{22}$ is an amino acid selected from the group consisting of Arg, Lys, Asn, His, Gln, Trp, Tyr, Ser, Thr, Pro, Cys, Ala, Gly, Glu, Asp, and Met, and $Xaa^{23}$ is an amino acid selected from the group consisting of Pro, Ser, Leu, Cys, Val, Ile, and Trp.

Particularly preferred single and double residue omission derivatives which are useful as peptide monomers in accordance with the present invention are the single and double residue omission derivatives of a peptide monomer having the structure of (SEQ ID NO. 3) wherein $Xaa^5$, $Xaa^6$, $Xaa^7$, $Xaa^8$, $Xaa^{10}$, $Xaa^{11}$, $Xaa^{12}$, $Xaa^{13}$, $Xaa^{18}$, $Xaa^{19}$, $Xaa^{21}$, $Xaa^{22}$ and $Xaa^{23}$ may be the same or different and are selected from the group of amino acids consisting of Ala, Arg, Asn, Asp, Cys, Gln, Crlu, Gly, His, Ile, Leu, Lys, Met, Phe, Pro, Ser, Thr, Trp, Tyr, and Val.

In accordance with another aspect of the present invention, the terms "monomer" and "peptide monomer" include antimicrobial peptides which are active against at least one pathogen, and in particular, against at least one plant pathogen, which are substituted, other than at the N or C-terminus, with a single Cys. This is not to say that these peptides may not also be substituted in other positions with other amino acids, or also include deletions, but merely that the resulting antimicrobial peptide contains a single non-terminal Cys. Examples of such peptides are those having the structure of (SEQ ID NO. 1) wherein the His normally found at position 7 is substituted with Cys, or the peptide having the structure of (SEQ ID NO. 2) wherein the His at position 7 is substituted with Arg and the Ser normally found at position 8 is substituted with Cys. Monomers in accordance with this aspect of the present invention are also not limited to magainin related compounds and may include Cys substitutions in antimicrobial peptides such as P1, Cecropin A, $PGL^c$, and the like and/or the previously discussed RAMP-PPS. Thus for example, a monomer in accordance with this aspect of the present invention could include a peptide having the structure of (SEQ ID NO. 10) wherein the Met normally found at the third position thereof is substituted with Cys. This peptide could also include an N or C terminal addition to the extent that the addition is not Cys.

POST-SYNTHESIS MODIFICATIONS

There are various post-synthesis modifications of the peptides and peptide monomers described and defined herein which could improve their effectiveness against one or more pathogens and, in particular, plant pathogens. One such post-synthesis modification is amidation of the carboxyl termini of the various peptides including AMPPs, AMPPPs, RAMPPs, RAMPPPs and oligopeptides of the present invention. See, for example, Cuervo, et al., "The Magainins: Sequence Factors Relative to Increased Antimicrobial Activity and Decreased Hemolytic Activity," Peptide Res. 1, (1988), 81–86. Amidation of these peptides will generally improve their antimicrobial activity.

Other post-synthesis modifications of the peptides, peptide monomers and oligopeptides of the present invention may prove beneficial with respect to antimicrobial activity, resistance to proteolytic degradation, and/or phytotoxicity. These modifications may include post-translational modifications of peptides and/or peptide monomers prepared by biological expression from a DNA sequence. Such post-translational modifications include, but are not limited to, acetylation, phosphorylation, glycosylation, farnesylation, amidation, tyrosine sulfonation, oxidations by chemical or enzymatic means such as by oxidation of methionine residues, proline or tyrosine hydroxylation and/or proline isomerization.

OLIGOPEPTIDES

An oligopeptide in accordance with the present invention is a protein containing two or more peptide subunits or peptide monomers and, optionally, one or more bridges and/or a disulfide linkage. More specifically, the oligopeptides in accordance with the present invention include at least two peptide subunits or peptide monomers which are interconnected either directly through the use of a peptide bond or through the use of a bridging molecule and/or disulfide linkage.

The exact nature and mode of action of oligopeptides in accordance with the present invention is not completely understood. However, and without limitation, these compounds may promote the formation of active aggregates of peptide monomers. They may also produce structures which are either less sensitive to proteolytic degradation or lower in phytotoxicity, or both. Irrespective of the theory or mechanism or mechanisms behind their operation, the inventors have found that oligopeptides in accordance with the present invention are as active or more active than corresponding monomers on pathogenic microbes and, in particular, against microbial plant pathogens.

The structurally simplest oligopeptides in accordance with the present invention are the so-called "head-to-tail" dimeric oligopeptides. These dimers involve the direct peptide bonding of a first peptide monomer having an N and a C-terminus and a second peptide monomer also having an N and a C-terminus, such that the C-terminal residue of the first peptide monomer is bound to the amino acid in the N-terminal position of the second peptide monomer by a peptide bond.

These head-to-tail dimers are active against at least one pathogen and, more preferably, against at least one plant pathogen. In this regard, head-to-tail dimers are identical to the other oligopeptides described herein. Additionally, each of the two peptide subunits which make up the head-to-tail dimers in accordance with the present invention are also antimicrobial in and of themselves. Thus, the peptide monomers selected for use in head-to-tail dimeric oligopeptides may not include peptide monomers which lack antimicrobial activity.

Preferred head-to-tail dimers in accordance with the present invention include those in which the two peptide subunits, and therefore the at least one first and at least one second peptide monomers have a structure of either (SEQ ID NO. 1), (SEQ ID NO. 2), or (SEQ ID NO. 3), (SEQ ID NO. 6).

Particularly advantageous head-to-tail dimers in accordance with the present invention may be produced from peptide monomers chosen from the group of peptides having the structures (SEQ ID NO. 3) and (SEQ ID NO. 6). As previously discussed, the present inventors have discovered that P1 is useful as an AMPPP by virtue of not only its activity against plant pathogenic bacteria, but also by virtue of its natural resistance to proteolytic degradation. P1 is also naturally low in phytotoxicity as a monomer. P1 is, however, somewhat limited in the scope of its antimicrobial impact. Therefore, its combination, in dimeric form with a modified magainin which, preferably, has been modified such that it is active against at least one plant pathogen and is also relatively resistant to proteolytic degradation, can, therefore, provide a potent oligopeptide for the defense of an organism and, in particular, plants and plant tissue. The resulting oligopeptide may also exhibit acceptable phytotoxicity.

Other particularly preferred head-to-tail dimers in accordance with the present invention include, without limitation: (SEQ ID NO. 2)-(SEQ ID NO. 2); (SEQ ID NO. 1)-(SEQ ID NO. 1); (SEQ ID NO. 1)-(SEQ ID NO. 2)*; (SEQ ID NO. 1)-(SEQ ID NO. 3); Met-(SEQ ID NO. 1)-(SEQ ID NO. 1) *; Met-(SEQ ID NO. 3)-(SEQ ID NO. 3)**; Met-(SEQ ID NO. 6)-(SEQ ID NO. 1)*; (SEQ ID NO. 3)-(SEQ ID NO. 7)*; Met-(SEQ ID NO. 1)-(SEQ ID NO. 9); (SEQ ID NO. 6)-(SEQ ID NO. 3); (SEQ ID NO. 10)-(SEQ ID NO. 3) ; Met-(SEQ ID NO. 7) -(SEQ ID NO. 3); (SEQ ID NO. 3)-(SEQ ID NO. 1); and Met-(SEQ ID NO. 3)-(SEQ ID NO. 6) wherein "*" indicates that the identified peptide MONOMER can be reversed in order and "****" indicates that the identified peptide monomer can be reversed in order and has the structure wherein $Xaa^5$ is Phe, $Xaa^6$ is Leu, $Xaa^7$ is selected from the group consisting of His, Lys, Phe, Ser and Arg, $Xaa^8$ is selected from the group consisting of Ser, His, Thr, Ala and Glu, $Xaa^{10}$ is selected from the group consisting of Gly and Lys, $Xaa^{11}$ is Lys, $Xaa^{12}$ is Phe, $Xaa^{13}$ is selected from the group consisting of Gly and Ala, $Xaa^{18}$ is selected from the group consisting of Gly and Ala, $Xaa^{19}$ is Glu $Xaa^{21}$ is Met, $Xaa^{22}$ is selected from Asn and Lys, and $Xaa^{23}$ is selected from the group consisting of Ser and Pro. Single and multiple residue omission derivatives of these monomers, including [Des (Gly 1, Ile 2)] Mag 2, [Des (Gly 1, Ile 2), Arg 7, Glu 8, Pro 23] Mag 1 [Des (Lys 22, Ser 23)] Mag 1, and derivatives thereof are also contemplated.

Head-to-tail trimers and other extended head-to-tail multimers in accordance with the present invention should include at least one first peptide monomer and at least one second peptide monomer, each of which are active against at least one pathogen and, preferably, against at least one plant pathogen. The remaining peptide subunit or subunits which, preferably, number from 1 to about 14, may also be antimicrobial peptides and/or AMPPPs. Most preferred head-to-tail oligopeptides include only antimicrobial peptide monomers. However, the remaining peptide subunits need not have antimicrobial activity. Examples of particularly preferred head-to-tail oligopeptide multimers include: (SEQ ID NO. 1)-(SEQ ID NO. 1)-(SEQ ID NO. 1); (SEQ ID NO. 1) $_4$; (SEQ ID NO. 1) $_6$; (SEQ ID NO. 2)-(SEQ ID NO. 2)-(SEQ ID NO. 2); (SEQ ID NO. 2)-(SEQ ID NO. 1)-(SEQ ID NO. 1)*; (SEQ ID NO. 1)-[(SEQ ID NO. 2)]$_4$-(SEQ ID NO. 3); and (SEQ ID NO. 7)-(SEQ ID NO. 1)-(SEQ ID NO. 9)*; wherein "*" and "**" have the same meaning as previously described.

Another type of oligopeptide which is structurally similar to the oligopeptides just described are the so-called "bridged" oligopeptides. These bridged oligopeptides can be identical to the head-to-tail oligopeptides just described with the exception that at least two of the peptide monomer subunits of which the oligopeptide is composed are separated by an interposed bridge. Thus, in its simplest form, the bridged oligopeptides in accordance with the present invention are composed of at least one first and at least one second peptide monomer, and a bridge. The C-terminus of the at least one first peptide monomer is directly peptide bound to the N-terminus of the bridge and the C-terminus of the bridge is directly peptide bound to the N-terminus of the at least one second peptide monomer. The resulting structure can be represented as a dimeric bridged oligopeptide having the structure of (SEQ ID NO. 2)-bridge-(SEQ ID NO. 2) which is a bridged dimer of two Magainin 2 subunits wherein the "-" represent peptide bonds and the "bridge" is a bridging peptide in accordance with the present invention.

The structurally simplest bridged multimer in accordance with this aspect of the present invention is a trimer having a single bridge. For example, if a peptide monomer having the structure (SEQ ID NO. 1) were directly attached, via its N-terminus, to the C-terminus of the second Magainin 2 in the above-described bridged dimer, the resulting oligopeptide would have a structure (SEQ ID NO. 2)-bridge-(SEQ ID NO. 2)-(SEQ ID NO. 1). Bridged trimers need not, however, be limited to a single bridging molecule. For example, the structure described immediately above could be modified by the use of an additional bridge such that the resulting trimeric bridged oligopeptide would have a structure of (SEQ ID NO. 2)-bridge$_1$-(SEQ. ID NO. 2)-bridge$_2$-(SEQ ID NO. 1). "Bridge$_1$" and "bridge$_2$" may be the same or may be different.

The term "bridge", as used herein, encompasses an amino acid based molecule which is used to separate two peptide subunits within an oligopeptide. Bridges in accordance with the present invention are molecules having an N and a C-terminus and therefore bound to each of the peptide subunits through a conventional peptide bond.

The "bridge" in accordance with the present invention can be of variable length and composition. However, irrespective of its dimensions or components, the bridge in accordance with the present invention must be capable of promoting inter-monomer interactions amongst the monomers in a specific oligopeptide. Furthermore, the bridge should be selected such that it is capable of conferring resistance to or minimizing undesirable cellular events within the bridged oligopeptide such as phosphorylation or glycosylation, to the extent such processes are disadvantageous. In a particularly preferred aspect of the present invention, the bridges should not interfere with the capacity of a bridged oligopeptide to travel across a cell membrane, and in particular, the cell membranes of eucaryotic plant cells. Thus, preferred bridged oligopeptides in accordance with the present invention are capable of being transported to an extracellular compartment.

Oligopeptides in accordance with the present invention have several advantages. One of the more important of these is the ability of these proteins to provide protection against pathogens. As previously explained, the present inventors are not completely aware of the mechanisms of this antimicrobial activity. However, without wishing to be bound to any particular theory of operation, the present inventors believe that this activity is related to the ability of a peptide to form aggregates and membrane disruptive ion channels in the cellular membrane of pathogens. The, ability of these oligopeptides to facilitate these phenomena appears to be dependent, at least in part, on the ability of the subunits of individual oligopeptides, and indeed, in many instances, a plurality of oligopeptides to interact.

While the head-to-tail oligopeptides in accordance herewith may exhibit the ability to promote beneficial aggregates, by an intermonomer interaction and/or by interoligopeptide interaction, the results obtained by the use of bridges in accordance with the present invention do show even greater activity of oligopeptides against at least plant pathogenic microbes than the associated AMPPP monomer subunits. Part of the explanation for this phenomenon may lie in the intramolecular dynamics of the various oligopeptide components. For example, the head-to-tail dimer (SEQ ID NO. 2)-(SEQ ID NO. 2) has been shown to have enhanced activity. This may be due to the "flexibility" of the region surrounding the peptide bond joining the two peptide monomers. Because this area may allow for advantageous secondary and tertiary conformations, the bound peptide monomers may be allowed to interact. This interaction is dependent, in part, upon the ability of portions of the monomers to be placed, even for a transitory period, in relatively close proximity. By close proximity it is understood to mean that some portion of each of the at least first and at least second peptide monomers are brought to within less than about 10 angstroms of each other, and, more preferably, within less than about 7 angstroms of each other.

The present inventors have discovered that the use of a bridge provides a further enhancement in activity. Thus, it is likely that the use of a bridge further facilitates the inter-monomer interaction between the subunits of an oligopeptide. Bridges in accordance with the present invention may accomplish this in a number of ways.

The use of a bridge, even a small one, may provide sufficient space between discrete monomers to prevent disadvantageous steric hindrance, or the creation of energetically stable bonds which would enhance advantageous inter-monomer interactions. Furthermore, the use of certain bridges may provide a sufficient degree of flexibility to the oligopeptide to allow for the formation of advantageous conformations. Thus, by imparting flexibility, it is possible to provide for advantageous spacing between peptide monomers and allow for advantageous inter-monomer interactions. Another possibility is that the use of a bridge which, while not "flexible," may impart a specific conformation which brings the peptide monomers into positions which promote advantageous intermonomer interactions.

The present inventors have found that relatively smaller bridges of five (5) amino acids or less are particularly useful in the construction of oligopeptides in accordance with the present invention. These bridges provide sufficient flexibility to the resulting structure to allow a range of motion which further facilitates the inter-monomer interaction, or provide a secondary structure which directly promotes or provides for such interaction.

The present inventors have also noted that undesirable peptide secondary structures such as alpha helix or beta strands which might dominate the structure of the resulting oligopeptide and hinder potential interactions between the monomers generally require more than five amino acids in length. See W. Kabsch and C. Sander, "Dictionary of protein secondary structure: pattern recognition of hydrogen-bonded and geometrical figures," *Biopolymers* 22, (1983), 2577–2637 and R. Muthusamy and P. K. Ponnuswamy, "Variation of amino acid properties in protein secondary structures, alpha-helices and beta-strands," *Int. J. Peptide Protein Res.* 38, (1990), 378–395 for analyses of alpha helices and beta strands in natural proteins.

One of the preferred bridges in accordance with the present invention has the structure of (SEQ ID NO. 5) wherein Xaa$^1$ through Xaa$^5$ are individually selected from the group consisting of Ala, Arg, Asn, Asp, Cys, Gln, Glu, Gly, Pro, Ser, Thr, Tyr and Val. Particularly preferred bridges include those where Xaa$^1$ is Gly, Xaa$^2$ is Gly, Xaa$^3$ is Ser, Xaa$^4$ is Ser and Xaa$^5$ is Gly, or where Xaa$^1$ through Xaa$^5$ are all the amino acid Gly. Another preferred 5 amino acid containing bridge has the structure of (SEQ ID NO. 5) wherein Xaa$^1$ is Gly, Xaa$^2$ is Arg, Xaa$^3$ is Arg, Xaa$^4$ is Pro, and Xaa$^5$ is Gly. The latter of these, which is a Gly-rich bridge, is expected to be flexible in solution because Gly side chain moieties are unlikely to sterically hinder any potential folding of the oligopeptide so as to allow and, in fact, promote intermonomer interactions between the peptide subunits of an oligopeptide. The result is increased activity of the oligopeptide against target pathogenic microorganisms. Additionally, Gly side chain atoms cannot participate in energetically stable bond structures or interactions such as hydrogen bonds or electrostatic charge bridges which might interfere with beneficial intermonomer interactions. Similarly, any peptide bridge which can be flexible in aqueous solution as predicted by a various secondary structure prediction algorithms, see, W. Kabsch & C. Sander, *Biopolymers* 22 (1984) 2577–2637; J. Garnier et al., *J. Mol. Biol.* 120 (1978) 97–120; and P. Y. Chou & G. D. Fasman,

*Biochemistry*, 13 (1974) 211–222, and are Gly-rich, would therefore be acceptable for the present invention. Exemplary preferred bridged peptide sequences would include but are not limited to the following bridges containing between 1 and 5 amino acids: Ser-Ser-Gly-Gly, Ser-Ser-Gly-Gly-Gly, Ser-Gly-Gly-Ser, Ser-Gly-Ser-Gly-Gly, Gly-Gly-Gly-Gly-Ser, Gly, Gly-Gly, and the like.

There are a large number of other compositions of bridge peptides which can satisfy the size requirements for preferred bridge peptides or more preferred bridge peptides. Preferred compositions would include but are not limited to those which form beta turns (cf. B. L. Sibanda and J. M. Thornton, *Nature*, 316, (1985), 170–174; and J. S. Richardson and D. C. Richardson, infra.

Similarly, single amino acid bridges such as, for example, the use of a single Gly as a bridge between two antimicrobial peptide monomers may provide sufficient flexibility, and/or sufficient secondary structure to promote intermonomer interactions of the type described herein.

Bridges need not be limited to five amino acids or less to be effective in accordance with the present invention. However, since longer bridges may impart undesirable secondary and/or tertiary conformation to the resulting oligopeptide, it is important to select only bridges which will provide for or promote inter-monomer interaction between the various peptide subunits of the oligopeptides of the present invention.

Groups of longer bridges useful in accordance with the present invention include helix-joining peptide units such as extracellular domains of transmembrane proteins, omega loops or other flexible connecting peptide chains. Extracellular domains of transmembrane proteins useful in accordance with the present invention vary in length from about 6 to about 100 amino acids. These domains rather than domains which reside in the cell or the cell membrane are useful because they can be transported across the cellular membrane, thus facilitating not only intermonomer interaction, but also excretion into the extracellular space. Additionally, these extracellular domains may, in some cases, act as signal or targeting peptides as described herein. See, K. Verner and G. Schatz, "Protein Translocation Across Membranes," *Science* 241 (1988), 1307–1313; L. Gierasch, "Signal Sequences," *Biochemistry* 28, (1989), 924–930; and *von Heijne, infra*. There are many such extracellular domains known in nature such as, for example, the peptides having the structure of (SEQ ID NO. 16) or (SEQ ID NO. 17).

Additional known extracellular domains which may be useful as bridges in forming oligopeptides in accordance with the present invention are identified in P. R. Schofield et al., "Sequence and Functional Expression of the GABA$_A$ Receptor Shows a Ligand-Gated Receptor Super-Family," *Nature* 328, (1987), 221–227; J. E. O'Tousa et al., "The Drosophila ninaE Gene Encodes an Opsin," *Cell* 40, (1985), 839–850; A. Vassarotti et al., "Independent Mutations at the Amino Terminus of a Protein Act as Surrogate Signals for Mitochondrial Import," *EMBO J.* 6, (1987), 705–711; J. P. Adelman et al., "Isolation Of The Gene and Hypothalamic cDNA for the Common Precursor of Gonadotropin-Releasing Hormone And Prolactin Release-Inhibiting Factor in Human and Rat," *Proc. Natl. Acad. Sci* (U.S.A.) 83, (1986), 179–183; C. S. Zuker et al., "Isolation and Structure of a Rhodopsin Gene from D. melanogaster," *Cell* 40, (1985), 851–858; H. Vogel et al., "The Structure of the Lactose Permease Derived from Raman Spectroscopy and Prediction Methods," *EMBO J.* 4, (1985), 3625–31; T. J. Jentsch et al., "Primary Structure of *Torpedo marmorata* Chloride Channel Isolated by Expression Cloning in Xenopus Oocytes," *Nature* 348, (1990), 510–514; A. Kamb et al., "Molecular Characterization of Shaker, a Drosphila Gene that Encodes a Potassium Channel," *Cell* 50, (1987), 405–413; A. Baumann et al., "Molecular Organization of the Maternal Effect Region of the Shaker Complex of Drosophila: Characterization of an I$_a$ Channel Transcript with Homology to Vertebrate Na$^+$ Channel," *EMBO J.* 6, (1987), 3419–29; T. Tanabe et al., "Primary Structure of the Receptor for Calcium Channel Blockers from Skelatal Muscle," *Nature* 328, 1987, 313–318; U. B. Kaupp et al., "Primary Structure and Functional Expression from Complementary DNA of the Rod Photoreceptor Cyclic GMP-gated Channel," *Nature* 342, (1989), 762–766; M. Noda et al., *Nature* 322, (1986), 826–828.

Omega loops are structures of generally between about 6 and about 16 amino acids in length that have no regular structure and whose end-to-end distance is less than about 10 angstroms. Some omega loops are longer. Some of these loops may also be classified as extracellular domains. There are many such loops known in nature such as those having the structure of a jp48 portion of Phage T4 lysozyme (residues 134–139, inclusive) (SEQ ID NO. 18) or a portion of *Bacillus stearothermophilus* thermolysin (residues 188–203, inclusive) (SEQ ID NO. 19). Additional known omega loops which may be useful as bridges in forming oligopeptides in accordance with the present invention are identified in J. F. Leszczynski and G. D. Rose, "Loops in Globular Proteins: A Novel Category of Secondary Structure," *Science* 234, (1986), 849–855. When used in the oligopeptides of the present invention, these omega loops may promote intermonomer interaction by bringing the monomers into a sufficiently close proximity.

Other flexible connecting peptide chains which may be used as a bridge in accordance with the present invention include, for example, the peptide having the structure of (SEQ ID NO. 23). See J. S. Huston, et al., "Protein Engineering of Antibody Binding Sites: Recovery of Specific Activity in an Anti-digoxin single-chain Fv analog produced in *Escherichia coli*," Proc. *Natl. Acad. Sci.*, (USA) 85, (1988), 5879–83.

In a preferred embodiment in accordance with the present invention such longer chain bridges would provide for or promote the spacing of some part of at least two peptide monomers in a single oligopeptide to be capable of being spaced within approximately 10 angstroms of each other and, more preferably, within about 7 angstroms of each other. See also J. S. Richardson, "The anatomy and taxonomy of protein structure," *Adv. Protein Chem.* 34, (1981), 167–339 and J. S. Richardson and D. C. Richardson, "Principles and patterns of protein conformation," in Prediction of Protein Structure and the Principles of Protein Conformation (G. D. Fasman, Ed.; Plenum Press, New York, N.Y.), pp. 1–98 (1989) for definitions and discussions of secondary structural elements of peptides or proteins mentioned in the preceding several paragraphs.

Therefore, a bridge in accordance with the present invention may be as small as a single amino acid or as large as 100 amino acids. More preferably, however, the bridge includes between about 1 and about 20 amino acids. The length of the bridge may vary based on a number of factors.

In one preferred embodiment in accordance with the present invention the "bridge" is a single amino acid which may be selected from the group of Ala, Arg, Asn, Asp, Cys, Gln, Glu, Gly, His, Ile, Leu, Lys, Met, Phe, Pro, Ser, Thr, Trp, Tyr, and Val.

In a more preferred embodiment in accordance with this aspect of the present invention, the bridge is composed of a single amino acid selected from the group consisting of Ala, Arg, Asn, Asp, Gln, Glu, Gly, His, Ile, Leu, Lys, Met, Phe, Ser, Thr, Trp, Tyr, and Val. Particularly preferred bridges in accordance with this aspect of the present invention include: Gly, Ala, or Ser.

Bridges having between 2 and 4 amino acids may also be used advantageously for the production of oligopeptides. The amino acids used in these bridges may be selected from the group consisting of Ala, Arg, Ash, Asp, Cys, Gln, Glu, Gly, His, Ile, Leu, Lys, Met, Phe, Pro, Set, Thr, Trp, Tyr, and Val. More preferably the amino acids are selected from the group consisting of Ala, Arg, Asn, Asp, Cys, Gln, Glu, Gly, His, Lys, Pro, Ser, Thr, Tyr, and Val.

Preferred bridges in accordance with the present invention include those having the structure of (SEQ ID NO. 4) wherein $Xaa^1$ through $Xaa^4$ may be substituted as described immediately above. The resulting bridges include those in which $Xaa^1$ is Gly, Ser, Asn or Lys, $Xaa^2$ is Gly, Lys, Asp, Ala or Arg, $Xaa^3$ is Gly, Glu, Thr, or Ser and $Xaa^4$ is Gly, Glu, Pro or Ser. Bridges including one or more Cys amino acids may also be included. Bridges of between 2 and 4 amino acids in length may include, for example, those peptides which form beta-turns such as Gly-Gly, Ser-Lys, Ser-Gly, Asn-Lys-Glu-Glu, and Ser-Asp-Gly-Pro, as well as other peptides such as Ser-Ser, Gly-Arg-Ser, Ala-Lys-Ala, Lys-Als-Thr-Glu, and Gly-Arg-Ser-Ser, and the like.

Other bridges containing between 2 and 5 amino acids in length include those constructed from the amino acids selected from the group consisting of Ala, Arg, Asn, Asp, Cys, Gln, Glu, Gly, His, Ile, Leu, Lys, Met, Phe, Pro, Ser, Thr, Trp, Tyr, and Val. More preferably the amino acids are selected from the group consisting of Ala, Arg, Asn, Asp, Cys, Gln, Glu, Gly, His, Lys, Pro, Ser, Thr, Tyr, and Val.

Another preferred bridge in accordance with the present invention is that having the structure of (SEQ ID NO. 5) wherein $Xaa^1$ through $Xaa^5$ may be selected from the groups described above. In a preferred embodiment this five-membered bridge is composed of amino acids selected from the group of Gly, Ala, His, Lys, Ser, Arg, and Pro and, one particularly preferred bridge of structure (SEQ ID NO. 5) is that where in $Xaa^1$ through $Xaa^5$ are Gly.

Some representative bridged oligopeptides in accordance with the present invention include, without limitation: (SEQ ID NO. 1)-(SEQ ID NO. 5)-(SEQ ID NO. 1); (SEQ ID NO. 2)-(SEQ ID NO. 5)-(SEQ ID NO. 2); (SEQ ID NO. 1)-(SEQ ID NO. 5)-(SEQ ID NO. 20)\*\*\*; (SEQ ID NO. 1)-Ala-(SEQ ID NO. 3)\*\*\*\*; (SEQ ID NO. 1)-(Gly)$_3$-(SEQ ID NO. 3) \*\*\*\*; (SEQ ID NO. 3)-(SEQ ID NO. 4)-(SEQ ID NO. 3)\*\*\*\*; (SEQ ID NO. 3)-Cys-Gly-Gly-(SEQ ID NO. 3)\*\*\*\*; (SEQ ID NO. 3)-Gly-Gly-Gly-(SEQ ID NO. 1); (SEQ ID NO. 1)-(SEQ ID NO. 5)-(SEQ ID NO. 1)-(SEQ ID NO. 1)-(SEQ ID NO. 7) \*\*\*; (SEQ ID NO. 3)-(SEQ ID NO. 5)-(SEQ ID NO. 3)-(SEQ ID NO. 5)-(SEQ ID NO. 3)\*\*\*\*; (SEQ ID NO. 3)-Gly-(SEQ ID NO. 3)-Gly-(SEQ ID NO. 3)\*\*\*\*; (SEQ ID NO. 3)-Gly-(SEQ ID NO. 3)-(SEQ ID NO. 5)-(SEQ ID NO. 3)\*\*\*\*; and (SEQ ID NO. 20)-(SEQ ID NO. 4)-(SEQ ID NO. 9)-(SEQ ID NO. 3)\*\*\*\*, wherein "\*\*\*" and "\*\*\*\*" have the same meaning as previously described and $Xaa^1$ through $Xaa^5$ of (SEQ ID NO. 5) are each Gly as are $Xaa^1$ through $Xaa^4$ of (SEQ ID NO. 4).

It is also possible to construct oligopeptides without the use of a bridging peptide and, in fact, without joining the peptide subunits by a peptide bond. Specifically, it is possible to produce oligopeptides in accordance with the present invention by joining individual peptide subunits by disulfide bonds or linkages which result from the oxidation of properly aligned Cys amino acids at the terminus of adjacent subunits.

Oligopeptides in accordance with this aspect of the present invention, unlike those previously described, may be joined in a "head-to-head" or "tail-to-tail" configuration such that the respective N-termini or C-termini of two adjacent peptide subunits are disulfide bound to each other. This may be accomplished by either appending a Cys to the N or C-termini respectively of two adjacent peptide monomers to be connected, i.e., using two single residue C or N-terminal addition derivatives of the various peptide monomers in accordance with the present invention, or by substituting Cys for the individual N or C-terminal amino acids contained within a particular peptide, i.e., joining two single or multiple residue substitution derivatives.

An example of the first form (i.e., "head-to-head") of disulfide bound oligopeptide in accordance with the present invention is a dimer created from two peptides having the structure of (SEQ ID NO. 1) each of which has a Cys appended and peptide bound to the N-terminal Gly. The two N-terminal Cys are joined, as are the peptide monomers, by a disulfide bond.

An example of the second form (i.e, "tail-to-tail") of disulfide bound oligopeptide in accordance with this aspect of the present invention includes the disulfide bonding of two peptides having the structure of (SEQ ID NO. 3) wherein $Xaa^5$ is Phe, $Xaa^6$ is Leu, $Xaa^7$ is His, $Xaa^8$ is Ser, $Xaa^{10}$ is Gly, $Xaa^{11}$ is Lys, $Xaa^{12}$ is Phe, $Xaa^{13}$ is Gly, $Xaa^{18}$ is Gly, $Xaa^{19}$ is Glu, $Xaa^{20}$ is Met, $Xaa^{22}$ is Lys and $Xaa^{23}$ is Cys. These single residue substitution derivatives of Magainin 1 are then attached by a disulfide bond which is formed between the two C-terminal Cys.

The peptide monomers used in the previous examples may also be combined to produce a disulfide bound oligopeptide. For example, the at least one first peptide monomer used could be a single residue substitution derivative as previously described having a base structure of (SEQ ID NO. 3) wherein the C-terminal amino acid (normally Ser) is replaced or substituted with a Cys and the at least one second peptide monomer would be a single residue C-terminal addition derivative of, for example, a peptide having a structure of (SEQ ID NO. 2) wherein a Cys is peptide bound to the C-terminal Ser thereof. A disulfide bond could then be formed between the two C-terminal Cys amino acids thus producing a "tail-to-tail" disulfide bridged dimeric oligopeptide in accordance with the present invention.

Disulfide linked oligopeptides in accordance with the present invention may also be linked in a head-to-tail configuration. For example, a first peptide having the structure of (SEQ ID NO. 3) and having a Cys substituted for the C-terminal amino acid and a second peptide of (SEQ ID NO. 1) having a Cys appended to the N-terminus may be linked by a disulfide linkage to form a dimeric oligopeptide. This oligopeptide would have the structure (SEQ ID NO. 3) -S-S-Cys- (SEQ ID NO. 1) wherein for (SEQ ID NO. 3) $Xaa^5$=Phe, $Xaa^6$=Leu, $Xaa^7$=His, $Xaa^8$=Ser, $Xaa^{10}$=Gly, $Xaa^{11}$=Lys, $Xaa^{12}$=Phe, $Xaa^{13}$=Gly, $Xaa^{18}$=Gly, $Xaa^{19}$=Glu, $Xaa^{21}$=Met, $Xaa^{22}$=Lys, and $Xaa^{23}$=Cys.

Preferably, the oligopeptides in accordance with the present invention contain only a single disulfide bridge. Thus, for example, an oligopeptide containing a disulfide bridge could include other peptide subunits which are directly bonded in a head-to-tail configuration as previously described and/or additional peptide subunits which may be attached by a bridge as previously described.

Examples of these oligopeptides include, without limit:

HO-(SEQ ID NO. 20)\*-Cys-S-S-Cys-(SEQ ID NO. 20)-OH;

H$_2$N-(SEQ ID NO. 20)-Cys-S-S-Cys-(SEQ ID NO. 20)-NH$_2$;

H₂N-Met-(SEQ ID NO. 9)-Cys-S-S-Cys-(SEQ ID NO. 1)-OH;

H₂N-Met-(SEQ ID NO. 20)-Cys-S-S-Cys-(SEQ ID NO. 20)-OH;

H₂N-Met-(SEQ ID NO. 20)-(SEQ ID NO. 5)-Cys-S-S-Cys-(SEQ ID NO. 20)-OH;

H₂N-Met-(SEQ ID NO. 20)₄-(SEQ ID NO. 1)-Cys-S-S-Cys-(SEQ ID NO. 2)-OH;

H₂N-(SEQ ID NO. 20)₄-(SEQ ID NO. 9)-Cys-S-S-Cys-(SEQ ID NO. 10)-OH;

H₂N-(SEQ ID NO. 1)-(SEQ ID NO. 15)-(SEQ ID NO. 3)-Cys-S-S-Cys-(SEQ ID NO. 9)-(SEQ ID NO. 5)-(SEQ ID NO. 20)-OH.

As previously described, "-" indicates a peptide bond, "-S-S-" indicates a disulfide bond, and "*" indicates a peptide in an inverted position.

The use of a terminal Cys as a way of providing for a disulfide linkage between adjacent peptide subunits also allows for the possibility of the same terminal Cys further bonding to another peptide via a peptide bond. In this context, the term "another peptide" includes structures which may be as small as a single amino acid residue, or may be a peptide which is active against at least one pathogen. It could be a totally inactive peptide as well. Thus, it is possible to produce branched oligopeptides wherein a particular Cys is functionally linked by peptide bonds to two peptides, one of which is a peptide monomer, and also linked by a disulfide bond to a Cys contained on at least one other peptide monomer. An example of such a peptide includes an oligopeptide wherein the at least one first peptide monomer is a single residue C-terminal addition derivative of a peptide having the structure of (SEQ ID NO. 1) and the at least one second peptide monomer is a single residue N-terminal addition derivative of a peptide having the structure of (SEQ ID NO. 2) and there being provided another peptide having, for example, the structure of (SEQ ID NO. 6). The resulting peptide can be illustrated as

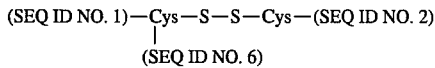

wherein the "-" represent peptide bonds, and "-S-S-" represents a disulfide linkage.

Another example of this type of oligopeptide has the structure of

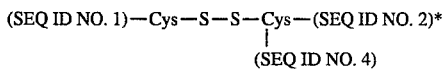

wherein the asterisk indicates an inverted peptide (in this instance, the inverted form of (SEQ ID NO. 2) with a single residue C-terminal addition of Cys), the "-" represent peptide bonds, and "-S-S-" represents a disulfide linkage.

The first example includes a "head-to-tail" configuration for the disulfide linked peptide monomers and the second example illustrates a "tail-to-tail" configuration. Another oligopeptide in accordance with the present invention includes at least one peptide monomer which is internally substituted with Cys. That is to say, these oligopeptides use at least one monomer which is substituted other than at the N or C-termini with a Cys. It is possible, therefore, to "cross-link" peptides from within the interior portion of each peptide monomer. For example, two peptide monomers each having a structure of (SEQ ID NO. 2) each of which is substituted at position 22 with a Cys (i.e., substitution of Asn normally in position Xaa²² with Cys) can be disulfide linked. Alternatively, one internally Cys substituted peptide monomer may be linked through a disulfide linkage to the N or C-terminal Cys monomers previously described. An example of such an oligopeptide includes a linkage, via a disulfide bond, of a first peptide monomer having the structure of (SEQ ID NO. 2)-Cys (i.e., a single residue C-terminal addition derivative of Magainin 2) and a second monomer having the structure of (SEQ ID NO. 2) wherein, for example, the Asn at position Xaa²² is substituted with Cys. These monomers are then connected via a disulfide linkage formed between the two Cys amino acids.

It may also be advantageous in accordance with the present invention to produce oligopeptides which have a bridging structure that includes both a bridge as defined herein and a disulfide linkage. Thus, for example, it is possible to produce an oligopeptide having the structure (SEQ ID NO. 3)-S-S-Cys-(SEQ ID NO. 4)-(SEQ ID NO. 2) wherein in (SEQ ID NO. 3) Xaa⁵ is Phe, Xaa⁶ is Leu, Xaa⁷ is His, Xaa⁸ is Cys, Xaa¹⁰ is Gly, Xaa¹¹ is Lys, Xaa¹² is Phe, Xaa¹³ is Gly, Xaa¹⁸ is Gly, Xaa¹⁹ is Glu, Xaa²¹ is Met, Xaa²² is Lys and Xaa²³ is Ser and Xaa¹–Xaa⁴ of (SEQ ID NO. 4) are each Gly. A disulfide linkage forms between the Cys in position 8 of the first peptide monomer and the N-terminal Cys attached to the five Gly-containing bridge attached to the second monomer. It may also be useful to include a plurality of bridge units such that, for example, the resulting structure would be (SEQ ID NO. 2)-(SEQ ID NO. 5)-Cys-S-S-Cys-(SEQ ID NO. 5)-(SEQ ID NO. 3) or (SEQ ID NO. 2)-Ala-Cys-S-S-Cys-Gly-(SEQ ID NO. 2)* wherein "*" indicates a peptide in an inverted position.

COMPLEMENTARY PEPTIDE MIXTURES

Bascomb, et al., supra, in attempting to modify the structure of known antimicrobial peptides discovered that certain peptides may lose efficacy against one particular pathogen or group of pathogens while at the same time gaining, or at least not substantially losing activity against others. Thus, for example, a peptide having a structure of (SEQ ID NO. 2) wherein the Ser at position 8 is substituted with Glu remains relatively active against plant pathogenic fungi when compared to Magainin 2. The modification, however, unexpectedly and beneficially produced a 50% or more decrease in the susceptibility of the resulting peptide to proteolytic degradation, as well as reducing the phytotoxicity of the peptide by 50%. Unfortunately, this peptide showed dramatic loss in its efficacy against at least one plant pathogenic bacteria. Similarly, the present inventors have discovered that a known naturally occurring peptide, P1, is highly effective as an AMPPP against plant pathogenic bacteria and is very low in both phytotoxicity and susceptibility to proteolysis. However, P1 has very little efficacy against at least some plant pathogenic fungi.

These observations and discoveries lead to the concept of combining compositions such as the two described immediately above such that the resulting mixture has a much broader spectrum of antimicrobial activity than could be realized from the use of either peptide singularly. The effect of the addition of these two compositions together is therefore complementary.

The antimicrobial compositions in accordance with this aspect of the present invention include one first antimicrobial peptide which is relatively active against one group of pathogens and relatively inactive against another group of pathogens and at least one second antimicrobial peptide which is relatively active against the group of pathogens which the at least one first antimicrobial peptide is relatively inactive against and relatively inactive against the group of pathogens which the at least one first antimicrobial peptide is relatively active against.

When the term "peptide" is used in accordance with this aspect of the present invention (i.e., for complementary peptide mixtures) the inventors are not contemplating "peptide monomers" as the complementary peptides. In the active form, complementary peptides are not intended to be bound to each other and, therefore, are not "monomers." Neither the at least one first antimicrobial peptide nor the at least one second antimicrobial peptide need be active against plant pathogens. However, it is preferred that at least one of the aforementioned is active against at least one plant pathogen and, in a more preferred embodiment in accordance with the present invention, both of said antimicrobial peptides are active against at least one plant pathogen.

In accordance with this more preferred aspect of the present invention the at least one first antimicrobial peptide is relatively active against plant pathogenic bacteria and relatively inactive against plant pathogenic fungi and the at least one second antimicrobial peptide is relatively active against plant pathogenic fungi and relatively inactive against plant pathogenic bacteria. In accordance with this aspect of the present invention, representative peptides from which the at least one first antimicrobial peptide may be selected include (SEQ ID NO. 6); (SEQ ID NO. 3) wherein $Xaa^5$ is Phe, $Xaa^6$ is Leu, $Xaa^7$ is His, $Xaa^8$ is Ser, $Xaa^{10}$ is Lys, $Xaa^{11}$ is Lys, $Xaa^{12}$ is Phe, $Xaa^{13}$ is Ala, $Xaa^{18}$ is Ala, $Xaa^{19}$ is Ile, $Xaa^{21}$ is Met, $Xaa^{22}$ is Asn, and $Xaa^{23}$ is Ser; (SEQ ID NO. 3) wherein $Xaa^5$ is Phe, $Xaa^6$ is Leu $Xaa^7$ is His, $Xaa^8$ is Ser $Xaa^{10}$ is Lys, $Xaa^{11}$ is Lys, $Xaa^{12}$ is Phe, $Xaa^{13}$ is Ala, $Xaa^{18}$ is Ala $Xaa^{19}$ is Ile, $Xaa^{21}$ is Met, $Xaa^{22}$ is Asn, and $Xaa^{23}$ is Ser and having a Met peptide bound to the N-terminal Gly; (SEQ ID NO. 2) peptide bound to (SEQ ID NO. 2); (SEQ ID NO. 2) peptide bound to the bridge of (SEQ ID NO. 5), said bridge also being bound to another peptide of structure (SEQ ID NO. 2); (SEQ ID NO. 3) wherein $Xaa^5$ is Phe, $Xaa^6$ is Leu, $Xaa^7$ is His, $Xaa^8$ is Ser, $Xaa^{10}$ is Lys, $Xaa^{11}$ is Lys, $Xaa^{12}$ is Phe, $Xaa^{13}$ is Ala, $Xaa^{18}$ is Ala, $Xaa^{19}$ is Glu, $Xaa^{21}$ is Met, $Xaa^{22}$ is Asn and $Xaa^{23}$ is Ser; the AMPPP just described further including an N-terminal Met peptide bound thereto, and identical Magainin 1 substitution derivatives.

The at least one second antimicrobial peptide may be selected from the group consisting of (SEQ ID NO. 1), (SEQ ID NO. 2), (SEQ ID NO. 2) having a Met peptide-bound to the N-terminal Gly, (SEQ ID NO. 2) wherein the Met at position 21 is oxidized, (SEQ ID NO. 1) wherein the Met at position 21 is deleted; (SEQ ID NO. 2) wherein the N-terminal Gly is deleted and the Ile at position 2 is replaced with a Met; (SEQ ID NO. 2) wherein the Lys in position 10 is replaced with His; (SEQ ID NO. 2) wherein the Lys in position 11 is replaced with His; (SEQ ID NO. 2) wherein the Lys in positions 10 and 11 are replaced with His and His, respectively; (SEQ ID NO. 2) wherein the Ser at position 8 is replaced with Thr; (SEQ ID NO. 2) wherein the Set at position 8 is replaced with Ala; (SEQ ID NO. 2) wherein the Set at position 8 is replaced with Glu; (SEQ ID NO. 2) wherein the His in position 7 is replaced with Phe; (SEQ ID NO. 2) wherein the Asn and the Ser in positions 22 and 23 respectively are deleted; (SEQ ID NO. 1) wherein the Gly in position 10 is replaced with His; (SEQ ID NO. 2) wherein the N-terminal Gly is deleted; (SEQ ID NO. 2) wherein the N-terminal Gly and the Ile in position 2 are deleted; (SEQ ID NO. 1) wherein the N-terminal Gly and the Ile in position 2 are deleted; (SEQ ID NO. 1) wherein the N-terminal Gly is deleted; (SEQ ID NO. 1) having a Met peptide bonded to the N-terminal Gly; (SEQ ID NO. 1) wherein the C-terminal Ser is deleted; (SEQ ID NO. 1) wherein the C-terminal Ser and the Lys in position 22 are deleted; (SEQ ID NO. 2) wherein the Asn in position 22 is replaced with Gly; (SEQ ID NO. 1) wherein the C-terminal Ser is deleted, the His in position 7 is replaced with Arg and the Ser in position 8 is replaced with Glu and having a Met peptide bound to the N-terminal Gly; and (SEQ ID NO. 1) wherein the His in position 7 is replaced with Arg, the Ser in position 8 is replaced with Glu, the Ser in position 23 is replaced with Pro and having a Met peptide bound to the N-terminal Gly (SEQ ID NO. 20).

Of course, the antimicrobial compositions in accordance with this aspect of the present invention need not be limited to the use of only two complementary antimicrobial peptides. For example, P1 which is highly active against plant pathogenic bacteria could be combined with two other AMPPPs, each of which are active against a discrete group of plant pathogenic fungi. The resulting three component mixture would thus provide a much broader spectrum of protection than any of the individual peptides singularly.

Thus additional benefits may accrue from the use of three or more antimicrobial peptides in a complementary mixture. For example, a third antimicrobial peptide may be added to a mixture which is somewhat similar in its range of activity against plant pathogens to one of the first two component peptides in the mixture, but this third antimicrobial peptide can be significantly less phytotoxic or significantly more resistant to proteolytic degradation than either of the first two component peptides. The resulting mixture may therefore allow for the sharing of the benefits of each individual component.

Preferred mixtures in accordance with the present invention include mixtures of (SEQ ID NO. 6) PLUS (SEQ ID NO. 1); (SEQ ID NO. 6) PLUS (SEQ ID NO. 10); (SEQ ID NO. 6) PLUS Met-(SEQ ID NO. 3) wherein for (SEQ ID NO. 3) $Xaa^5$ is Phe, $Xaa^6$ is Leu, $Xaa^7$ is Arg, $Xaa^8$ is Glu, $Xaa^{10}$ is Gly, $Xaa^{11}$ is Lys, $Xaa^{12}$ is Phe, $Xaa^{13}$ is Gly, $Xaa^{18}$ is Gly, $Xaa^{19}$ is Glu, $Xaa^{21}$ is Met, $Xaa^{22}$ is Lys, and $Xaa^{23}$ is Pro; (SEQ ID NO. 6) PLUS (SEQ ID NO. 3) wherein for (SEQ ID NO. 3) $Xaa^5$ is Phe, $Xaa^6$ is Leu, $Xaa^7$ is His, $Xaa^8$ is Ser, $Xaa^{10}$ is Gly, $Xaa^{11}$ is Lys, $Xaa^{12}$ is Phe, $Xaa^{13}$ is Gly, $Xaa^{18}$ is Gly, $Xaa^{19}$ is Glu, $Xaa^{21}$ is Met, and $Xaa^{22}$ and $Xaa^{23}$ are omitted; (SEQ ID NO. 6) PLUS (SEQ ID NO. 3) wherein for (SEQ ID NO. 3) $Xaa^5$ is Phe, $Xaa^6$ is Leu, $Xaa^7$ is His $Xaa^8$ is Ser, $Xaa^{10}$ is Lys, $Xaa^{11}$ is Lys, $Xaa^{12}$ is Phe, $Xaa^{13}$ is Gly, $Xaa^{18}$ is Gly $Xaa^{19}$ is Glu, $Xaa^{21}$ is Met, and $Xaa^{22}$ and $Xaa^{23}$ are omitted; (SEQ ID NO. 6) PLUS (SEQ ID NO. 3) wherein for (SEQ ID NO. 3) $Xaa^1$ is omitted and $Xaa^5$ is Phe, $Xaa^6$ is Leu, $Xaa^7$ is His, $Xaa^8$ is Ser, $Xaa^{10}$ is Gly, $Xaa^{11}$ is Lys, $Xaa^{12}$ is Phe, $Xaa^{13}$ is Gly, $Xaa^{18}$ is Gly, $Xaa^{19}$ is Glu, $Xaa^{21}$ is Met and $Xaa^{22}$ is Lys and $Xaa^{23}$ is Ser; (SEQ ID NO. 6) PLUS (SEQ ID NO. 3) wherein for (SEQ ID NO. 3) $Xaa^1$ is omitted and $Xaa^5$ is Phe, $Xaa^6$ is Leu, $Xaa^7$ is His, $Xaa^8$ is Ser, $Xaa^{10}$ is Lys, $Xaa^{11}$ is Lys, $Xaa^{12}$ is Phe, $Xaa^{13}$ is Gly, $Xaa^{18}$ is Gly, $Xaa^{19}$ is Glu, $Xaa^{21}$ is Met, and $Xaa^{22}$ is Ash and $Xaa^{23}$ is Ser; (SEQ ID NO. 6) PLUS (SEQ ID NO. 3) wherein for (SEQ ID NO. 3) $Xaa^5$ is Phe, $Xaa^6$ is Leu, $Xaa^7$ is His, $Xaa^8$ is Ser, $Xaa^{10}$ is Gly, $Xaa^{11}$ is Lys, $Xaa^{12}$ is Phe, $Xaa^{13}$ is Gly, $Xaa^{18}$ is Gly, $Xaa^{19}$ is Glu, $Xaa^{21}$ is Met, and $Xaa^{22}$ is Asn and $Xaa^{23}$ is Ser; (SEQ ID NO. 6) PLUS (SEQ ID NO. 3) wherein for (SEQ ID NO. 3) $Xaa^1$ is omitted and $Xaa^5$ is Phe, $Xaa^6$ is Leu, $Xaa^7$ is His, $Xaa^8$ is Ser, $Xaa^{10}$ is Gly, $Xaa^{11}$ is Lys, $Xaa^{12}$ is Phe, $Xaa^{13}$ is Gly, $Xaa^{18}$ is Gly, $Xaa^{19}$ is Glu, $Xaa^{21}$ is Met, and $Xaa^{22}$ is Lys and $Xaa^{23}$ is Ser; (SEQ ID NO. 6) PLUS (SEQ ID NO. 7); (SEQ ID NO. 2)-(SEQ ID NO. 2) PLUS (SEQ ID NO. 1); (SEQ ID NO. 2)-(SEQ ID NO. 2) PLUS (SEQ ID NO. 10); (SEQ ID NO. 2)-(SEQ ID NO. 2) PLUS Met-(SEQ ID NO. 3) wherein for (SEQ ID NO. 3)

Xaa$^5$ is Phe, Xaa$^6$ is Leu, Xaa$^7$ is Arg, Xaa$^8$ is Glu, Xaa$^{10}$ is Gly, Xaa$^{11}$ is Lys, Xaa$^{12}$ is Phe, Xaa$^{13}$ is Gly, Xaa$^{18}$ is Gly, Xaa$^{19}$ is Glu, Xaa$^{21}$ is Met, Xaa$^{22}$ is Lys, and Xaa$^{23}$ is Pro; (SEQ ID NO. 2)-(SEQ ID NO. 2) PLUS (SEQ ID NO. 3) wherein for (SEQ ID NO. 3) Xaa$^5$ is Phe, Xaa$^6$ is Leu, Xaa$^7$ is His, Xaa$^8$ is Ser, Xaa$^{10}$ is Gly, Xaa$^{11}$ is Lys, Xaa$^{12}$ is Phe, Xaa$^{13}$ is Gly, Xaa$^{18}$ is Gly, Xaa$^{19}$ is Glu, Xaa$^{21}$ is Met, and Xaa$^{22}$ and Xaa$^{23}$ are omitted; (SEQ ID NO. 2)-(SEQ ID NO. 2) PLUS (SEQ ID NO. 3) wherein for (SEQ ID NO. 3) Xaa$^1$ is omitted and Xaa$^5$ is Phe, Xaa$^6$ is Leu, Xaa$^7$ is His, Xaa$^8$ is Ser, Xaa$^{10}$ is Gly, Xaa$^{11}$ is Lys, Xaa$^{12}$ is Phe, Xaa$^{13}$ is Gly, Xaa$^{18}$ is Gly, Xaa$^{19}$ is Glu, Xaa$^{21}$ is Met, and Xaa$^{22}$ is Lys and Xaa$^{23}$ is Ser; (SEQ ID NO. 2)-(SEQ ID NO. 2) PLUS (SEQ ID NO. 3) wherein for (SEQ ID NO. 3) Xaa$^1$ is omitted and Xaa$^5$ is Phe, Xaa$^6$ is Leu, Xaa$^7$ is His, Xaa$^8$ is Ser, Xaa$^{10}$ is Lys, Xaa$^{11}$ is Lys, Xaa$^{12}$ is Phe, Xaa$^{13}$ is Gly, Xaa$^{18}$, Gly, Xaa$^{19}$ is Glu, Xaa$^{21}$ is Met, and Xaa$^{22}$ is Asn and Xaa$^{23}$ is Ser; (SEQ ID NO. 2)-(SEQ ID NO. 2) PLUS (SEQ ID NO. 3) wherein for (SEQ ID NO. 3) Xaa$^5$ is Phe, Xaa$^6$ is Leu, Xaa$^7$ is His, Xaa$^8$ is Ser, Xaa$^{10}$ is Gly, Xaa$^{11}$ is Lys, Xaa$^{12}$ is Phe, Xaa$^{13}$ is Gly, Xaa$^{18}$ is Gly, Xaa$^{19}$ is Glu, Xaa$^{21}$ is Met, Xaa$^{22}$ is Asn, and Xaa$^{23}$ is Ser; (SEQ ID NO. 2)-(SEQ ID NO. 2) PLUS (SEQ ID NO. 3) wherein for (SEQ ID NO. 3) Xaa$^1$ is omitted and Xaa$^5$ is Phe, Xaa$^6$ is Leu, Xaa$^7$ is His, Xaa$^8$ is Ser, Xaa$^{18}$ is Gly, Xaa$^{10}$ is Gly, Xaa$^{11}$ is Lys, Xaa$^{12}$ is Phe, Xaa$^{13}$ is Gly, Xaa$^{18}$ is Gly, Xaa$^{19}$ is Glu, Xaa$^{21}$ is Met, Xaa$^{22}$ is Lys, and Xaa$^{23}$ is Ser; (SEQ ID NO. 2)-(SEQ ID NO. 2) PLUS (SEQ ID NO. 7); (SEQ ID NO. 6) PLUS Met-(SEQ ID NO. 3) PLUS (SEQ ID NO. 1) wherein for (SEQ ID NO. 3) Xaa$^5$ is Phe, Xaa$^6$ is Leu, Xaa$^7$ is Arg, Xaa$^8$ is Glu, Xaa$^{10}$ is Gly, Xaa$^{11}$ is Lys, Xaa$^{12}$ is Phe, Xaa$^{13}$ is Gly, Xaa$^{18}$ is Gly, Xaa$^{19}$ is Glu, Xaa$^{21}$ is Met, Xaa$^{22}$ is Lys, and Xaa$^{23}$ is Pro; (SEQ ID NO 6) PLUS (SEQ ID NO. 3) PLUS (SEQ ID NO. 10) wherein for (SEQ ID NO. 3) Xaa$^5$ is Phe, Xaa$^6$ is Leu, Xaa$^7$ is Phe, Xaa$^8$ is Ser Xaa$^{10}$ is Lys, Xaa$^{11}$ is Lys, Xaa$^{12}$ is Phe, Xaa$^{13}$ is Gly, Xaa$^{18}$ is Gly, Xaa$^{19}$ is Glu, Xaa$^{21}$ is Met, Xaa$^{22}$ is Asn, and Xaa$^{23}$ is Ser; (SEQ ID NO. 6) PLUS (SEQ ID NO. 7) PLUS (SEQ ID NO. 1); (SEQ ID NO. 6) PLUS (SEQ ID NO. 7) PLUS (SEQ ID NO. 2); (SEQ ID NO. 6) PLUS (SEQ ID NO. 7) PLUS Met-(SEQ ID NO. 3) wherein for (SEQ ID NO 3) Xaa$^5$ is Phe, Xaa$^6$ is Leu, Xaa$^7$ is Arg, Xaa$^8$ is Glu, Xaa$^{10}$ is Gly, Xaa$^{11}$ is Lys, Xaa$^{12}$ is Phe, Xaa$^{13}$ is Gly, Xaa$^{18}$ is Gly, Xaa$^{19}$ is Glu, Xaa$^{21}$ is Met, Xaa$^{22}$ is Lys, and Xaa$^{23}$ is Pro; (SEQ ID NO. 2)-(SEQ ID NO. 2) PLUS (SEQ ID NO. 3) PLUS (SEQ ID NO. 3) where for the first (SEQ ID NO. 3) Xaa$^1$ and Xaa$^2$ are omitted and Xaa$^5$ is Phe, Xaa$^6$ is Leu, Xaa$^7$ is His, Xaa$^8$ is Ser, Xaa$^{10}$ is Gly, Xaa$^{11}$ is Lys, Xaa$^{12}$ is Phe, Xaa$^{13}$ is Gly, Xaa$^{18}$ is Gly, Xaa$^{19}$ is Glu, Xaa$^{21}$ is Met, Xaa$^{22}$ is Lys, and Xaa$^{23}$ is Ser, and wherein for the second (SEQ ID NO. 3) Xaa$^5$ is Phe Xaa$^6$ is Leu, Xaa$^7$ is His, Xaa$^8$ is Ser, Xaa$^{10}$ is Gly, Xaa$^{11}$ is Lys, Xaa$^{12}$ is Phe, Xaa$^{13}$ is Gly, Xaa$^{18}$ is Gly, Xaa$^{19}$ is Glu, Xaa$^{21}$ is Met, and Xaa$^{22}$ and Xaa$^{23}$ are omitted; (SEQ ID NO. 10) PLUS (SEQ ID NO. 3) PLUS (SEQ ID NO. 3) wherein for the first (SEQ ID NO. 3) Xaa$^1$ and Xaa$^2$ are omitted and Xaa$^5$ is Phe, Xaa$^6$ is Leu, Xaa$^7$ is His, Xaa$^8$ is Ser, Xaa$^{10}$ is Gly, Xaa$^{11}$ is Lys, Xaa$^{12}$ is Phe, Xaa$^{13}$ is Gly, Xaa$^{18}$ is Gly, Xaa$^{19}$ is Glu, Xaa$^{21}$ is Met, Xaa$^{22}$ is Lys and Xaa$^{23}$ is Ser, and wherein for the second (SEQ ID NO 3) Xaa$^5$ is Phe, Xaa$^6$ is Leu, Xaa$^7$ is His, Xaa$^8$ is Ser, Xaa$^{10}$ is Gly, Xaa$^{11}$ is Lys, Xaa$^{12}$ is Phe, Xaa$^{13}$ is Gly, Xaa$^{18}$ is Gly, Xaa$^{19}$ is Glu, Xaa$^{21}$ is Met, and Xaa$^{22}$ and Xaa$^{23}$ are omitted; Met-(SEQ ID NO. 3) PLUS (SEQ ID NO. 3) PLUS (SEQ ID NO. 3) wherein for the first (SEQ ID NO. 3) Xaa$^5$ is Phe, Xaa$^6$ is Leu, Xaa$^7$ is His, Xaa$^8$ is Ser, Xaa$^{10}$ is Gly, Xaa$^{11}$ is Lys, Xaa$^{12}$ is Phe, Xaa$^{13}$ is Ala, Xaa$^{18}$ is Ala, Xaa$^{19}$ is Glu, Xaa$^{21}$ is Met, Xaa$^{22}$ is Lys, and Xaa$^{23}$ is Ser; wherein for the second (SEQ ID NO. 3) Xaa$^1$ and Xaa$^2$ are omitted and Xaa$^5$ is Phe, Xaa$^6$ is Leu, Xaa$^7$ is His, Xaa$^8$ is Set, Xaa$^{10}$ is Gly, Xaa$^{11}$ is Lys, Xaa$^{12}$ is Phe, Xaa$^{13}$ is Gly, Xaa$^{18}$ is Gly, Xaa$^{19}$ is Glu, Xaa$^{21}$ is Met, Xaa$^{22}$ is Lys and Xaa$^{23}$ is Ser, and wherein for the third (SEQ ID NO. 3) Xaa$^5$ is Phe, Xaa$^6$ is Leu, Xaa$^7$ is His, Xaa$^8$ is Ser, Xaa$^{10}$ is Gly, Xaa$^{11}$ is Lys, Xaa$^{12}$ is Phe, Xaa$^{13}$ is Gly, Xaa$^{18}$ is Gly, Xaa$^{19}$ is Glu, Xaa$^{21}$ is Met and Xaa$^{22}$ and Xaa$^{23}$ are omitted; and the like.

In addition to the peptides described above, the complementary mixtures in accordance with the present invention may additionally include carriers, diluents, preservatives, buffers, and the like. These include buffers, such as Tris(tris-[hydroxymethyl]aminomethane); MES (2-[N-morpholino] ethane sulfonic acid); and HEPES (N-[2-hydroxyethyl]piperazine-N'-[2-ethanesulfonic acid]) and preservatives, such as sodium azide or thimerosal. Mixtures of these additives may also be useful. When present, these additives generally are present in an amount of about 0.01% to about 10% (w/v).

The peptides used in the complementary mixtures in accordance with the present invention may be made by either the chemical or genetic methods described herein. These peptides may then be collected and mixed in the appropriate ratio and therefore provided to plants or other organisms for their protection in much the same way as the RAMPPPs and oligopeptides of the present invention are provided. These mixtures may additionally be genetically produced by allowing for the co-expression of, for example, a P1 and [Arg 7] Mag 1 described above. The resulting expressed peptides would thus form in situ the complementary mixture of the present invention. Such an in situ formation could be realized within the internal compartments of a cell or could be realized after the peptides are individually excreted into the extracellular space between the cells.

Furthermore, the mixture could be produced by the creation of, for example, a bridged dimeric oligopeptide wherein the C-terminus of, for example, a peptide monomer of P1 was bound to the N-terminus of a peptide bridge composed of two amino acids having His at the N-terminus and Ser at the C-terminus, the C-terminus of the bridge being bound to, for example, the N-terminal Gly of the single residue substitution derivative of Magainin 1 described above. The present inventors have determined that plant proteases exist which are active and which recognize a His-Ser bond and cleave the bond therebetween. Thus, when the resulting oligopeptide is excreted from the cell, the extracellular proteases will cleave the two peptides resulting in a complementary mixture of a single residue C-terminal addition derivative (His) of P1 and the single residue N-terminal addition derivative (Ser) of the above-described substituted peptide. In this example, the at least one first peptide, P1, may additionally have a Met or (f)Met attached to its N-terminal end. The resulting peptide would, therefore, be a single residue N- and single residue C-terminal additional derivative of P1.

PROCEDURE FOR CHEMICALLY SYNTHESIZING PEPTIDES, PEPTIDE MONOMERS, INCLUDING REVERSE PEPTIDES, AND OLIGOPEPTIDES

Antimicrobial peptides, including AMPPPs, reverse peptides, as well as oligopeptides, bridges and peptide monomers in accordance with the present invention may be advantageously produced by either a traditional chemical synthesis or by one or more methods of inserting specific DNA material genetically encoding one or more peptides, bridges and/or fragments into a host cell and allowing that cell to express the desired peptide.

With regard to the traditional chemical synthesis, antimicrobial peptides, reverse peptides, bridges and oligopeptides, in accordance with the present invention can by synthesized using any of the known peptide synthesis protocols such as those described in "The Peptides: Analysis, Synthesis, Biology"; Volume 2—"Special Methods in Peptide Synthesis, Part A", E. Gross and J. Meienhofer, Eds., Academic Press, New York, 1980, and Volume 9—"Special Methods in Peptide Synthesis, Part C", S. Udenfriend and J. Meienhofer, Eds., Academic Press, San Diego, 1987.

Preferred for use in this invention for the chemical synthesis of peptides are solid phase techniques because they allow the rapid synthesis of highly pure peptides. In such procedures, peptides are synthesized, preferentially one amino acid at a time, on an insoluble polymer support (called a resin) starting from the C-terminus of the peptide. A synthesis is begun by appending the C-terminal amino acid (CTAA) of the peptide to the resin through a chemical linking group, such as an amide or an ester. If the latter is linked to the resin as an ester, the resulting peptide will be a C-terminal carboxylic acid; if linked as an amide, the resulting peptide will be a C-terminal amide. The CTAA, as well as all other amino acids used in peptide synthesis need to have their alpha-amino groups and side chain functionalities (if present) differentially protected as derivatives that can selectively be removed (deprotected) during the synthesis. Synthesis (coupling) is performed by reacting an activated form of an amino acid, such as its symmetrical anhydride or an active ester, with the unblocked alpha-amino group of the N-terminal amino acid appended to the resin. The sequence of deprotecting such alpha-amino groups followed by coupling is repeated until the entire peptide chain is constructed. All of the functionalities present in the peptide are then deprotected and the peptide is cleaved from the resin, usually in the presence of compounds called scavengers, which inhibit side reactions with the peptide during this process. The resulting peptide is then purified by a variety of techniques such as gel filtration, ion exchange and high performance liquid chromatography (HPLC). During the cleavage and purification processes, the peptide may be converted into any of a number of acid-salt forms bound to the amino groups present at the N-terminus and to any lysines (Lys), arginines (Arg), histidines (His) or ornithines (Orn) of the peptide and, consequently, the resulting pure peptide is usually obtained in the form of such a salt.

Preferred for use in this invention are Merrifield-type solid phase techniques as described in G. Barany and R. B. Merrifield, "Solid-Phase Peptide Synthesis," The Peptides: *Analysis, Synthesis, Biology*, Volume 2, Ch. 1, pp 3–284; and in J. M. Stewart and J. D Young in "Solid-Phase Peptide Synthesis, 2nd Ed", Pierce Chemical Company, Rockford, Ill., 1984. In general, any standard side group protection strategy may be advantageously utilized, although t-Boc (tert-butyloxycarbonyl; see, for example, Barany and Merrifield, and Stewart and Young, supra) and FMOC (9-fluorenylmethoxycarbonyl; see, for example, E. Atherton and R. C. Sheppard in "The Fluorenylmethoxycarbonyl Amino Protecting Group," supra, Volume 9, Ch. 1, pp 1–38) strategies are preferred.

The synthesis of peptide-resins required as precursors to peptides containing a C-terminal carboxylic acid are typically begun on commercially available cross-linked polystyrene or polyamide polymer resins such as chloromethyl, hydroxymethyl, aminomethyl, PAM (phenylacetamidomethyl), HMP (p-hydroxymethylphenoxyacetic acid), p-benzyloxybenzyl alcohol, Hycram (4-bromocrotonyl-beta-alanylamidomethyl); Advanced Chemtech, Inc., Louisville, Ky.), or Sasrin (2-methoxy-4-alkoxybenzyl) alcohol; Bachem Bioscience, Inc., Philadelphia, Pa.). Coupling of amino acids can be accomplished using either symmetrical anhydrides produced, for example, from DCC (dicyclohexylcarbodiimide), HOBT (1-hydroxybenzotriazole) active esters produced, for example, from DCC/HOBT or, for example, from various BOP reagents (see, for example, J. Coste, et al., "BOP and Congeners: Present Status and New Developments", Proceedings of the Eleventh American Peptide Symposium; Peptides: Chemistry, Structure and Biology, J. E. Rivier and G. R. Marshall, Eds., ESCOM, Leiden, Neith., 1990, pp 885–888) in solvents such as DCM (dichloromethane), DCM containing TFE (trifluoroethanol), DMF (N,N-dimethylformamide), NMP (N-methylpyrrolidone), or NMP containing DMSO (dimethylsulfoxide).

Preferred for use in this invention are coupling of symmetrical anhydrides of t-Boc-protected amino acids, except for arginine (Arg), asparagine (Asn), glutamine (Gln), and histidine (His), which are preferably coupled as HOBT active esters produced from DCC/HOBT, on PAM resins in DMF or DMF/DCM solutions, and coupling of DCC/HOBT produced HOBT active esters of FMOC protected amino acids on HMP-polystyrene resins in NMP solutions.

More preferred for use in this invention is coupling of DCC/HOBT produced HOBT active esters of t-Boc protected amino acids on PAM resins first in NMP, then in an 80/20 solution of NMP/DMSO, and finally in an 80/20 solution of NMP/DMSO containing 1.9 mmol DIEA/0.5 mmol PAM resin.

Synthesis of peptide-resins as precursors to peptides containing a C-terminal amide can satisfactorily be achieved using the previously described procedures. However, a polymer support such as a benzhydrylamine (BHA) or 4-methylbenzhydrylamine (MBHA) polystyrene resins should be used. Preferred for use in accordance with this aspect of the present invention, i.e., the production of AMPPPs having an amide group bound at the C-terminus are 4-methylbenzhydrylamine-polystyrene resins.

Many types of side-chain protecting groups may be used for either the t-Boc or FMOC solid-phase synthesis as described, for example, by Barany and Merrifield, supra, Gross and Meienhofer, Eds., "The Peptides: Analysis, Synthesis, Biology", Volume 3—"Protection of Functional Groups in Peptide Synthesis", Academic Press, New York, 1981, and Stewart and Young, supra, for t-Boc amino acids, and by Atherton and Sheppard, supra, for FMOC amino acids.

Preferred for use in this invention for t-Boc amino acids are MTS (mesitylene-2-sulfonyl) for arginine, OBzl (benzyl ester) for aspartic acid, 4-MeBzl (4-methylbenzylthioether) for cysteine, $Bzl_2$ (dibenzyldiether) for 3,4-dihydroxyphenylalanine, OBzl for glutamic acid, Bom (benzyloxymethyl) or Z (benzyloxycarbonyl) for histidine, Bzl for both 3- and 4-hydroxyproline, Cl-Z (2-chlorobenzyloxycarbonyl) for both lysine and ornithine, Bzl for both serine and threonine, CHO (formyl) for tryptophan and Br-Z (2-bromobenzyloxycarbonyl) for tyrosine. Methionine may be protected as its sulfoxide, Met(O), but preferably is used unprotected.

Peptides including AMPPPs, RAMPPPs, RAMPPPs, oligopeptides and bridges in accordance with the present invention can be synthesized using either automated instruments or manual techniques. However, automated techniques are preferred. All of the examples of AMPPPs described in this invention were actually prepared using an Applied Biosystems, Inc. (ABI) Model 430A automated peptide synthesizer using the t-Boc protocols described in the Applied Biosystems Model 430A peptide synthesizer User's Manual, Version 1.30, Section 6, Applied Biosystems, Foster City, Calif., February 1987 (revised November 1987 and October 1988).

According to these protocols, the peptides are assembled on the resins starting from the C-terminus of the peptide. PAM or HMP resins required for the synthesis of C-terminal carboxylic acids can be purchased from ABI or other manufacturers already linked to the alpha-amino acid and side chain protected C-terminal amino acid. However, when preparing C-terminal carboxyamides, the C-terminal amino acid must first be coupled to either a BHA or MBHA resin. In either case, the resin containing the alpha-amino and side chain protected C-terminal amino acid is placed into the reaction vessel and the peptide chain is preferably assembled one amino acid at a time (assemblage of peptide fragments is possible but is usually less preferred for the AMPPPs described in this invention) by a repetitive sequence of deprotecting the alpha-amino group of the N-terminal amino acid appended to the resin and coupling to this the next amino acid, which is also alpha-amino and side chain protected.

The sequence of deprotection of the alphaamino group of the N-terminal amino acid followed by coupling of the next, protected amino acid is continued until the desired peptide chain is assembled. The resulting N-terminal and side chain protected peptide linked to a polymer support resin is then subjected to the appropriate deprotection and cleavage procedure to provide the unprotected peptide, usually as N-terminal and lysine, histidine, arginine and ornithine acid salts.

Syntheses were performed using t-Boc protection strategies starting from 0.5 mmol of the C-terminal amino acid resin and 2.0 mmol of the side-chain protected, t-Boc amino acid in the coupling steps. These amounts, however, are not critical and proportionally larger or smaller amounts can be used depending on the type of automated instrument or manual apparatus employed. For example, syntheses utilizing as little as 0.1 mmol and as large as 0.6 mmol of amino acid-PAM resin have been performed by the inventors using the ABI instrument. Although a molar ratio of the to-be-coupled amino acid to the amino acid or peptide appended to the PAM resin of 4.0 is preferred when using this instrument, smaller and larger ratios may be employed. Ratios as low as 3.33 (0.6 mmol PAM resin/2.0 mmol of amino acid) have been used without any significant decrease in coupling efficiencies. Lower ratios may be employed to increase the quantity of peptide produced per run but are less preferred because the coupling efficiency and, hence, peptide purity may be lower. Larger ratios are generally not preferred because they are not any more efficient.

In syntheses based on t-Boc protection strategies in DMF, deprotection of alpha-amino groups is performed at ambient temperature using TFA/DCM followed by neutralization with DIEA/DMF. Symmetrical anhydrides are formed from DCC in DCM, except for leucine, methionine sulfoxides, tryptophan and formyl-tryptophan, which are formed in 10% DMF in DCM. After filtration of by-product DCU (N,N-dicyclohexylurea), the DCM is evaporated and replaced with DMF while the temperature is maintained at 10°–15° C. For AMPPPs synthesized using this protocol, amino acids were double coupled after the length of the growing peptide chain exceeded nine amino acids. For these cases, the DCM solution, after filtration, is used directly in the next step.

HOBT active esters are formed for asparagine, glutamine and protected histidine from the reaction of DCC with HOBT containing 8–10% v/v DCM, and from arginine(MTS) from the reaction of DCC with HOBT containing 25–30% v/v DCM. After filtration of by-product DCU, the HOBT active ester solutions are used directly in the next step without removal of the DCM. These four amino acids are always double coupled using the same procedure.

Once either the amino acid symmetric anhydride or HOBT active ester is produced in the appropriate solvent, the solution is transferred to the reaction vessel and shaken with the N-terminal alpha-amine deprotected peptide-resin. Coupling takes place during this period, which initially ranges from 18–26 minutes for symmetrical anhydrides to 26–42 minutes for HOBT active esters. The coupling period is gradually increased as the peptide chain is lengthened. For example, after 15 amino acids, an additional 10 minutes is added. Couplings are initially performed at the temperatures at which the symmetrical anhydrides are formed, but gradually ambient temperature is reached during the coupling period. At the completion of the coupling period, the resin is washed with DCM, a sample taken for ninhydrin monitoring (see Sarin et al., "Quantitative Monitoring of Solid-Phase Peptide Synthesis by the Ninhydrin Reaction," *Anal. Biochem.* 117, (1981), 147–157, and then dried in preparation for the next coupling cycle.

In syntheses based on t-Boc protection strategies in NMP, deprotection of alpha-amino groups is performed as above, except that neutralization of excess TFA is accomplished by washes with DIEA/DCM, DIEA/NMP and NMP alone. All amino acids are converted to HOBT active esters by reacting 1.0 equivalent each of DCC, HOBT and an N-terminal and side chain protected amino acid in NMP for about 40–60 minutes at ambient temperature. After filtration of by-product DCU, the HOBT active ester solutions are used directly in the coupling reaction. Coupling is performed at ambient temperature for 30 minutes in DMP, for another 16 minutes after enough DMSO is added to give a 20:80 solution of DMSO in NMP, and finally for another seven minutes after the addition of 1.9 mmol of DIEA. As the length of the peptide chain is increased, longer coupling times are used. For example, after the peptide chain has reached 15 amino acids, the coupling time will have increased by 15 minutes. Double couple cycles are performed in the same manner as the single couple cycles, but were generally used only for Lys$^4$ or the equivalent in AMPPPs. At the completion of the coupling cycles, unreacted amino groups remaining on the peptideresin are capped by treating them with a solution of 10% acetic anhydride and 5% DIEA in DCM for two minutes, followed by shaking with 10% acetic anhydride in DCM for four minutes. After washing well with DCM, a sample of the resin is taken for ninhydrin monitoring of coupling efficiency as above, and then dried in preparation for the next coupling cycle. Coupling efficiencies using either DMF or NMP were always greater than 98%, and in most cases greater than 99%.

Peptides including AMPPPs, oligopeptides, fragments, reverse peptides and fragments, in accordance with the present invention, may also be successfully synthesized using the FMOC chemistry described herein and available on an ABI Model 430A peptide synthesizer (K. M. Otteson, "Recent Developments with NMP Chemistry" in "Is Protein Chemistry an Art or a Science?", Applied Biosystems, FASEB Meeting, New Orleans, April, 1989). Also, S. Nozaki, "Solid Phase Synthesis of Magainin 1 Under Continuous Flow Conditions", *Chem. Lett.*, (1989), 749–752, has described in detail a method for synthesizing Magainin 1 using HMP resin and an automated FMOC procedure very similar to the one described herein.

Although all of the peptides described herein may be individually prepared, it is sometimes desirable and expedient to simultaneously prepare multiple peptides. Procedures for performing such syntheses are well known in the literature, and commercial instruments for performing such tasks are also available. For example, Cuervo, et al., "The Magainins: Sequence Factors Relevant to Increased Antimicrobial Activity and Decreased Hemolytic Activity" supra, and "Synthesis and Antimicrobial Activity of Magainin Alanine Substitution Analogues", supra reports the simultaneous preparation of omission and alanine substitution analogues of C-terminal amides and carboxylic acids of Magainin 1 and Magainin 2 using the SMPS (simultaneous multiple peptide synthesis) method with t-Boc protected amino acids on both PAM and 4-methylbenzhydryl amine resins. Also, F. S. Tjoeng, et al., "Multiple Peptide Synthesis Using a Single Support (MPS3)," Int. *J. Peptide Protein Res.* 35, (1990), 141–146, simultaneously prepared Magainin 2 analogues substituted with a variety of amino acids at position 21 using manual synthesis of t-Boc protected amino acids and PAM resins. In the same paper, however, these authors also showed that the method could be automated using an ABI Model 430A peptide synthesizer for the simultaneous synthesis of 11-substituted analogues of a porcine angeotensinogen peptide.

Procedures similar to those disclosed in the aforementioned paper can be used in the practice of the present invention specifically. In accordance herewith, a preferred technique could employ t-Boc amino acids, PAM resins and DCC/HOBT couplings in NMP-NMP/DMSO for the simultaneous synthesis of three magainin substitution analogues. A larger number of substitution analogues can simultaneously be coupled, but the separation of the resulting peptides becomes more difficult and the yield of each resulting peptide decreases.

In the practice of the present invention, it is possible to simultaneously synthesize portions of a variety of peptides containing large common segments. For example, peptides differing only at the C-terminus in substitution or chain length can simultaneously be synthesized by mixing together PAM resins containing the differing C-terminal sequences and then simultaneously sequentially coupling the common amino acid segments onto the mixture of resins in the normal manner. For this purpose, the use of HOBT active esters produced using DCC/HOBT in NMP or NMP/DMSO using t-Boc amino acids on PAM resins is the preferred method.

Similarly, large segments of peptides differing mainly at the N-terminus can simultaneously be synthesized by first preparing the peptide-PAM resin containing the common C-terminal chain until the first differing amino acid at the N-terminus is reached. The peptide-resin is then divided into separate vessels and each individual peptide synthesis continued independently. The two growing peptide-resins may be coupled to completion or further divided at a later stage of peptide synthesis if other desirable branching positions are reached. Preferred for use in multiple peptide syntheses within the scope of this invention are t-Boc protocols on PAM resins utilizing DCC/HOBT couplings in NMP or NMP/DMSO. In order to increase the amount of peptide-resin produced, 0.6 mmole rather than the standard 0.5 mmole of resin may be employed in multiple peptide syntheses without losing coupling efficiency.

The peptides obtained as precursors for either C-terminal carboxylic acid or amide peptides may be deprotected and cleaved from the resins using any of the well known, standard procedures described in the literature (see, for example, Barany and Merrified, supra; Stewart et al., supra; J. P. Tam and R. B. Merrifield in "Strong Acid Deprotection of Synthetic Peptides: Mechanisms and Methods", ("The Peptides: Analysis, Synthesis, Biology", Volume 9, Ch. 5, pp 185–248); and Applied Biosystems, "Strategies in Peptide Synthesis-Introduction to Cleavage Techniques", Applied Biosystems, 1990. For t-Boc peptide-resins, for example, these include standard anhydrous HF (hydrogen fluoride), low-high HF, TFMSA (trifluoromethanesulfonic acid) and TMSOTf (trimethylsilyl trifluoromethanesulfonate). However, standard HF and low-high HF procedures are preferred for use in this invention for deprotection of and cleavage from t-Boc peptide-resins. It is also preferred that the N-terminal t-Boc protecting group be removed before the peptide is subjected to HF deprotection and cleavage.

Cleavage and deprotection of t-Boc-peptide-PAM resins using "standard" anhydrous HF conditions is generally performed according to the procedures given in the references cited above. Typically, about 1 g of the peptide-resin is stirred for about 50–90 min. at $-5°$ C. to $0°$ C. in a solution of 10–12 mL of anhydrous HF containing 1.0 mL of anisole, 0.4 mL of dimethylsulfide (DMS), 0.2–0.4 mL of 1,2-ethanedithiol and 3 mg of 2-mercaptopyridine as scavengers. Slight variations in the amounts of scavengers present do not materially affect the results, and other scavengers, such as the ones described in the literature references cited above, may be used (for example, 3 mg of skatole should also be added for peptides containing tryptophan). It is preferred, however, that the reaction times and temperatures specified above be used, since shorter reaction times or lower reaction temperatures may result in incomplete deprotection or cleavage, while higher reaction temperatures may cause side reactions to occur. Longer reaction times are generally not beneficial and may lead to side reactions, although in certain cases, for example if an arginine protected with a tosyl group or several arginines are present in the peptide chain, reaction times up to two hours may be required to produce more complete deprotection. A particularly preferred procedure for performing the HF procedure is that of Immuno-Dynamics Inc., La Jolla, Calif. In this procedure the HF/scavenger/peptide-resin mixture is first stirred for 30 min. at $-10°$ C. and then for 30 min. at $0°$ C. (5 min. longer per arginine at $0°$ C.).

The "low-high" anhydrous HF procedure may be used for the deprotection and cleavage of any of the peptide-resins described in this invention in order to minimize side reactions, such as methionine alkylation, but is particularly preferred for deprotection and cleavage of the peptide-resin mixtures produced from the simultaneous synthesis of multiple peptides. The preferred procedure followed is basically that described by J. P. Tam et al. in "SN$_2$ Deprotection of Synthetic Peptides with a Low Concentration of HF in Dimethyl Sulfide: Evidence and Application in Peptide Synthesis", *J. Am. Chem. Soc.* 105, (1983), 6442–6455, and Tam and Merrifield, "Strong Acid Deprotection Of Synthetic Peptides: Mechanisms and Methods," supra and, involves stirring for about two hours at $-5°$ C. to $0°$ C. about 1 g of the peptide-resin in a solution of 10–20 mL (10–12 mL is preferred) of 2.5:6.5:1 anhydrous HF/dimethyl sulfide/p-cresol (if the peptide-resin contains Trp(For), then a solution of 10:26:3:1 anhydrous HF/dimethyl sulfide/p-cresol/thio-cresol is instead used). The HF and DMS are then removed at about $-5°$ C. to $0°$ C. under vacuum, and 10 mL of fresh, anhydrous HF is added. The "high" or "standard" cleavage is then performed by stirring the mixture for an additional 45–90 min. at −5° C. to 0° C. A more preferred method for performing this "high" HF deprotection is that of Immuno-Dynamics Inc. In this procedure, 1 mL of anisole, 0.4 mL of DMS, 0.4 mL of 1,2-ethanedithiol and 3 mg of 2-mercaptopyridine are added along with the 10 mL of fresh, anhydrous HF, and the mixture is stirred for 30 min. at −10° C. and 30 min. at 0° C. (5 min. longer per arginine at 0° C.).

After completion of either the "standard" or "low-high" HF deprotection and cleavage procedure, the HF and any remaining DMS are completely evaporated under vacuum at −5° C. to 0° C. The resulting peptide-resinscavenger mixture is then mixed with about 10–15 mL of diethyl ether, ethyl acetate or the like (volume is not critical, diethyl ether is preferred), filtered, and the residue washed another 2–4 times with 10–15 mL of diethyl ether, ethyl acetate or the like (volume is not critical, diethyl ether is preferred) to remove organic scavengers. It is preferable at this point to stir the residue for 30 min. with 5 mL of 2-mercaptoethanol (BME) in order to reduce methionine sulfoxides to methionines. The peptide is then extracted three times with 5–30 mL of 10–30% acetic acid containing 2% BME, the extracts are combined, diluted (if necessary) with water to give a final concentration of acetic acid of 10% or less, and then lyophilized (freeze-dried) to dryness. The weight of crude peptide obtained typically ranges from 50–90%.

After completing the "low-high" HF cleavage and deprotection procedure, a preferred method for extracting the peptide is that used by Immuno-Dynamics Inc. In this procedure, after evaporation of the HF and DMS, the peptide/resin mixture is swollen with chloroform, washed with 3×10 mL of ether, and stirred for 20–30 min. with 5 mL of BME. The mixture is then extracted three times with 5–30 mL of 1:1 10–30% acetic acid/BME (sometimes an additional extraction with 20–30 mL of 50% aqueous acetonitrile containing 0.1% TFA is beneficial). The extracts are then combined and extracted three times with 20 mL of ether to remove remaining scavengers, and the peptide is recovered by lyophilization of the aqueous acetic acid/(acetonitrile)/BME layer.

The crude peptides obtained from the HF deprotection cleavage procedures are present as N-terminal, lysine, arginine, histidine, and ornithine hydrogen fluoride salts and presumably also contaminated with other fluoride salts and scavengers (if other deprotection schemes are used, such as trifluoromethanesulfonic acid, other inorganic salts, such as trifluoromethanesulfonates, will instead be present). Such peptide or inorganic salts are not desirable, since alone or in the presence of moisture they may act as strong acids, which may either decompose the peptide or be toxic to a plant. It is therefore preferable to rid the peptide of such salts by further purification, which also provides a peptide with higher activity per unit weight. A preferred method for purifying the peptide is to remove the fluoride salts by anion exchange chromatography and then isolate it by HPLC (high performance liquid chromatography).

As typically performed in the practice of this invention, anion exchange chromatography provides the peptides as acetate salts, while HPLC provides the peptides as trifluoroacetate salts.

A typical method for performing ion exchange chromatography is to dissolve the crude peptide in a minimum volume of 5–30% acetic acid (the higher concentrations of acetic acid are required for the more hydrophobic peptides), filter off any residual insoluble material (such as occluded resin) and pass the solution through an anion exchange resin, such as BioRad AG 1X-8 (acetate form) (Bio-Rad Laboratories, Richmond, Calif.) in 5–30% acetic acid. The resulting peptide fractions, detected by a ninhydrin test (Sarin et al., supra) are combined and lyophilized to provide the peptides as N-terminal, lysine, arginine, histidine, and ornithine acetate salts, free of inorganic impurities, but possibly still containing scavengers. The peptides obtained in this manner are 50–80% pure, according to HPLC analysis (see below), and, as such, are highly effective in destroying plant pathogens. A peptide with somewhat higher activity per unit weight may be obtained, either before or after the anion exchange procedure, by treating the peptide salts with a weak base such as 5–10% ammonium bicarbonate or 6M guanidine hydrochloride in order to reverse any N→O acyl shift that occurred in peptides containing serines and/or threonines under the acidic cleavage conditions. Typically, this is accomplished by dissolving the peptide salt in 5–10% ammonium bicarbonate, allowing the solution to sit overnight at 15°–25° C. and then recovering the peptide by lyophilization.

In some cases, particularly when methionine is protected as its sulfoxides during the peptide chain assembly, it is advantageous to again treat the peptide mixture with a reducing agent in order to reduce any remaining methionine sulfoxides back to methionine. Although many reagents are described in the literature for this purpose, such as DTT (dithiothreitol) and DTE (dithioerythritol), MMA (N-methylmercaptoacetamide) is preferred. The reduction is typically performed by incubating a solution of 1 to 5 mg/mL of peptide in about a 10% w/v solution of MMA in 10–30% acetic acid for 12–48 hours at 20°–40° C. under a nitrogen atmosphere following the procedure of A. Culwell in "Reduction of Methionine Sulfoxide in Peptides Using N-Methylmercaptoacetamide" (MMA), Applied Biosystems Peptide Synthesizer User Bulletin No. 17, (1987), Foster City, Calif. The reduction can be monitored by HPLC, and the incubation stopped when the reduction is complete. Reduction of the methionine sulfoxides to methionine is not required, since the inventors have shown that such methionine sulfoxide containing peptides have activity against plant pathogens, but peptides with a higher activity per unit weight can be obtained by performing the reduction procedure. In cases where the peptides have been treated with MMA, excess MMA and associated by-products are removed by passing a solution of the peptide mixture in 5–30% acetic acid through a Sephadex G-25 column (Pharmacia LKB Biotechnology, Inc., Piscataway, N.J.) and monitoring the effluent at 254 nm. The peptide-containing fractions are combined and dried by lyophilization.

Peptides with the highest activity per unit weight are obtained by further purifying them by HPLC (high performance liquid chromatography). Typically, the peptides are purified by reversed phase HPLC by injecting 15–30 mg of the peptide dissolved in 1–2 mL of 0.1% TFA (trifluoroacetic acid) onto a 2.2×25 cm, 10 micron, 300 angstrom Vydac (Nest Group, Southboro, Mass.) C-4 column and eluting with various gradients of acetonitrile and water containing 0.1% TFA. The peptides obtained in this manner are N-terminal, lysine, arginine, histidine, and ornithine trifluoracetic acid salts, which are generally greater than 95% pure according to HPLC integration at 215 nm. Analytical HPLC of the peptide fractions is performed on a 0.46×25 cm, 10 micron, 300 angstrom, Vydac C-4 column using the following elution conditions: linear gradient of 0 to 60% B in A over 30 min; flow rate=1.0 mL/min; solvent A=0.1% aqueous TFA; solvent B=0.08% TFA in acetonitrile; monitoring by UV absorbance at 215 nm.

The structures of the peptides in most cases have been confirmed by amino acid or mass spectral analysis. Amino acid analysis of peptides was performed, following hydrolysis with 6N hydrochloric acid at 100° C. for 24 hours with an ion exchange column (for example, a Beckman Spherogel AA-Li$^+$ cation exchange column) by HPLC using a Beckman System Gold Amino Acid Analyzer (Beckman Instruments, Inc., Fullerton, Calif.) using ninhydrin detection. Amino acid analysis was also performed by Immuno-Dynamics, which detected the amino acids as PTC (phenylthiocarbamyl) derivatives on a Waters Associates Pico-Tag system (Millipore Corporation, Bedford, Mass.).

Amino acid analysis of the peptides have also been obtained using peptide-resins following the procedure of F. Westall et al. in "Fifteen Minute Acid Hydrolysis of Peptides," *Anal. Biochem* 61, (1974), 610–613. In these cases, the peptide-resin is hydrolyzed by 1:1 hydrochloric/propionic acid instead of hydrochloric acid alone. The resulting mixture is filtered through a 0.45 micron nylon filter using 2 to 4 volumes of water for washing, the filtrate is lyophilized and the residue analyzed as above.

Spectra from FAB-MS (fast atom bombardment-mass spectrometry) of the peptides were obtained using a Kratos MS5ORF mass spectrometer equipped with an Ion Tech B11NF saddled field gun operated at 8 kV and 40 microamps of current using xenon to create energetic ions. Spectra were obtained from a solution prepared by mixing 1 microliter of a 4 mM solution of the peptide with 1 microliter of 90% glycerol in 40 mM oxalic acid on the copper target of the sample probe. The instrument was calibrated with cesium iodide, scanned at a rate of 5 to 10 seconds per scan from a mass range from approximately 500 atomic mass units above and below the expected mass, and data were collected with multichannel analyzer programs available on a DS90 data system to provide (M+H)$^+$ fragments.

Chemical Synthesis of Oligopeptides

The chemical synthesis of oligopeptides of the type described in this invention, whether containing bridges or not, of lengths up to 140 amino acids may be accomplished using the techniques described above with t-Boc side-chain protection strategies (Clark-Lewis et al. "Automated Chemical Synthesis of a Protein Growth Factor for Hemopoietic Cells, Interleukin-3", *Science* 231 (1986) 134–139). The techniques, however, are preferred for the synthesis of oligopeptides of lengths up to 75 amino acids and more preferred for synthesis of oligopeptides of lengths up to 60 amino acids. The "Segment Condensation" method for the synthesis of peptides (E. T. Kaiser et al., "Peptide and Protein Synthesis by Segment Synthesis Condensation", *Science* 243 (1989) 187–192 is also a preferred method for the synthesis of oligopeptides of lengths from 60 to 75 amino acids, but more preferred for the synthesis of oligopeptides of lengths from 76 to 104 amino acids. The "Enzymatic Semisynthesis" method for the synthesis at peptides is another preferred method for the synthesis of oligopeptides of lengths from 60 to about 120 amino acids. For example, see V. DeFilippis, et al., "Semisynthesis of Carboxy-Terminal Fragments of Thermolysin", Proceedings of the Eleventh American Peptide Symposium; Peptides: Chemistry, Structure and Biology (J. E. River, et al.) (1990), pp. 1051–1053, published by ESCOM, Leiden, Neth; C. J. A. Wallone, et al., "Semisynthesis of a Deletion Mutant of Cytochrome by Condensation of Enzymatically Activated Fragments," Proceedings of the Tenth American Peptide Symposium; Peptides: Chemistry and Biology (G. R. Marshall) (1988), pp. 372–375, published by ESCOM, Leiden, neth; and J. van Binsbergen et al., "Trypsin-Catalyzed Coupling of Synthetic Peptides: Semisynthetic Production of Phospholipase A2 Mutants in High Yield", ibid., pp 381–382.

A modification of a combination of these procedures may be used to synthesize longer chain oligopeptides. Thus, segments of the oligopeptide of lengths up to 75 amino acids may be prepared as above and then either sequentially or in blocks be appended to each other using diphenyl phosphoryl azide as the coupling agent in a solvent such as NMP, DMF or DMSO (T. Shiori et al., "Diphenylphosphoryl Azide. A New Convenient Reagent for a Modified Curtius Reaction and for the Peptide Synthesis", *J. Am. Chem. Soc.* 94 (1972), 6203–6205. The use of Arg(NO$_2$) and Lys(TFA), which can be removed after the condensation, are preferred in this procedure. Multimers of a single peptide monomer may be prepared in the same manner (H. R. Bhattacharjee et al., "Bioadhesive Analogue Polypeptides Containing L-Dopa Residues: Synthesis, Polymerization and Adhesive Properties", *Polym. Mater. Sci. Eng.* 59 (1988), 110–114. The degree of oligomerization may be controlled by either the amount of diphenyl phosphorazide used or the reaction time. Higher molecular weight oligopeptides may be too insoluble in aqueous solvents to be purified by HPLC and thus be purified by column chromatography or used directly as a mixture.

Chemical Synthesis of Disulfide Linked Oligopeptides

Cys containing AMPPPs, reverse peptides and oligopeptides may be synthesized by the methods described in the invention subject to the same size limitation discussed in the previous section. The cysteines are then preferentially oxidized to cystines containing disulfides bridges using the procedure of R. S. Hodges, et al., "Peptide Design Using Model Synthetic Peptides", *Peptide Res.* 1 (1988), 19–30. Typically, solutions of cysteine-containing peptides are stirred in a phosphate buffer (pH 3–9 and preferred pH 7) containing a catalytic amount (0.001–25% and preferred 1.0%) of a cupric salt such as cupric chloride (0.001–0.5M and preferred 0.05M monosodium phosphate, $10^{-5}$ to $10^{-4}$M cupric chloride, 0.01–1M and preferred 0.5M sodium chloride) overnight at room temperature. The resulting oligopeptides are then purified.

AMPPP Genetic Synthesis and Purification

As previously noted, peptides including AMPPPs, reverse peptides, bridges, fragments, and oligopeptides in accordance with the present invention can also be prepared by introducing into a host cell a deoxyribonucleotide or DNA gene sequence encoding one or more peptides with appropriate regulatory signals such as a gene promoter sequence and a gene terminator sequence appended to such a gene sequence, and realizing expression of the gene sequences encoding these peptides in such a host cell through biological processes for protein synthesis. The host cell for this process can be either procaryotic (for example, a bacterial cell) or eucaryotic (for example, a plant or animal cell) in origin. For purposes of large scale production, microbial hosts such as bacteria or yeasts may be used due to the advanced state of fermentation processes for those organisms. Alternatively, other gene expression systems can be used for production of these peptides such as those involving fungi (for example, Neurospora), cultured human cells or insect cells.

Additionally, the use of genetic synthesis for peptides including AMPPPs, and particularly for the synthesis of oligopeptides as described in the present invention, may be particularly useful. As previously described, it is often useful to produce oligopeptide containing between about 2 and about 16 peptide subunits, exclusive of any bridging molecules. There currently are technical limitations on solid phase-based repetitive chemical synthesis of large oligopeptides as embodied in the present invention, with a practical limit in single syntheses of about 140 amino acids. Although there are, as previously described, chemical means for further polymerizing chemically derived peptides of up to this size, those chemical means lack precise control in the composition and number of peptide subunits which may be so polymerized. Therefore a need may exist for creating longer oligopeptides than possible by repetitive chemical synthesis, but many polymerization products may be too large or of an inappropriate size to be efficacious against plant pathogens. Furthermore, since antimicrobial peptides embodied by the present invention may incorporate bridging peptides which are tens, hundreds, even thousands of amino acid residues long and because genetic technology is well suited for production of oligopeptides and polypeptides that are very lengthy, of defined size and of defined composition, biological production of oligopeptides as well as monomeric antimicrobial peptides is a preferred means of obtaining quantities of antibiotic peptides useful within the scope of the present invention. Advancing technology in the creation of totally synthetic genes encoding large oligopeptides of precisely defined composition and the means of cheaply producing such oligopeptides by various biological mechanisms also suggest that biological production of antimicrobial peptides will become a more preferred method of production in the future and, in certain instances such as the production of AMPPPs in low value transgenic crop species, may be the only methodology available which is economically feasible.

Genes encoding AMPPPs, for example, can be prepared entirely by chemical synthetic means or can consist in part of a portion or all of a sequence derived from natural sequences encoding a peptide. Chemical synthesis of oligonucleotides composed entirely of deoxyribonucleotides can be achieved through application of solution chemistries or can be preferably carried out on solid supports. Several synthesis chemistries for oligonucleotides have been devised and include phosphotriester, phosphite-triester and phosphoramidite chemistries. See M. H. Caruthers, "New methods for chemically synthesizing deoxyoligonucleotides" in Methods of DNA and RNA Sequencing (S. M. Weissman, Ed.; Praeger Publishers, New York), (1983), 1–22, and K. Itakura et al., "Synthesis and use of synthetic oligonucleotides:, *Ann. Rev. Biochem.* 53, (1984), 323 356. Phosphoramidite synthesis chemistries such as those involving N,N-dimethylaminophosphoramidites or beta-cyanoethyl-diisopropylaminophosphoramidites or deoxyribonucleosidemorpholino-methoxyphosphines are preferred because of their efficient coupling of nucleotides to a growing oligonucleotide chain and for the stability of the chemical reagents employed. The most preferred phosphoramidite chemistries are those employing betacyanoethyl-diisopropylamino-phosphoramidites because of their extended stability relative to comparable intermediates and their avoidance of toxic reagents such as thiophenol. See, S. L. Beaucage and M. H. Caruthers, "Deoxynucleoside phosphoramidites—a new class of key intermediates for deoxypolynucleotide synthesis", *Tetrahedron Lett.* 22, (1981), 1859–1862; L. J. McBride and M. H. Caruthers, "An investigation of several deoxynucleotide phosphoramidites useful for synthesizing deoxyoligonucleotides:, *Tetrahedron Lett.* 24, (1983), 245–248; T. Dorper and E. L. Winnacker, "Improvements in the phosphoramidite procedure for the synthesis of oligodeoxyribonucleotides", *Nuc. Acids Res.* 11, (1983) 2575–2584; and S. P. Adams et al., "Hindered dialkylamino nucleoside phosphite reagents in the synthesis of two DNA 51-mers", *J. Amer. Chem. Soc.* 105, (1983), 661–663. Phosphoramidite chemistries on solid supports in brief consist of attaching a modified nucleotide to a solid material such as glass, silica gel, polyacrylamide, cellulose, polystyrene, nitrocellulose and some other generally chemically inert material. The nucleotide phosphate group and any exocyclic nitrogen atoms in the nucleotide base are protected on such supports with chemical groups so as to prevent unwanted side reactions during linear elongation of the oligonucleotide chain. Such attachments can be through a variety of linker or spacer moieties, but preferred linkers are generally long chain alkyl amines. See M. D. Matteucci and M. H. Caruthers, U.S. Pat. No. 4,458,066. The attached nucleotide is protected at the 5' sugar position with an acid labile dimethoxytrityl chemical group which is removed with an acid such as benzenesulfonic acid, trichloroacetic acid or dichloroacetic acid to free a 5'-OH group for coupling, thereby beginning linkage of additional nucleotides. Preferred acids for this deblocking or activation step are dichloroacetic acid or trichloracetic acid. A phosphoramidite monomer nucleoside protected similarly to the nucleotide attached to the solid support is then added in the presence of a weak acid to promote nucleophilic attack of the 5'-OH group on the phosphoramidite reagent. Preferred weak acids for the coupling step include tetrazole, amine hydrochlorides, and 3-nitrotriazole, with the most preferred weak acid being tetrazole. Failed coupling sites on the solid support are then blocked or capped by acetylation of free hydroxyl groups with acetic anhydride. A preferred coreactant in the capping step is 1-methylimidazole. The natural internucleotide phosphate diester linkage is subsequently generated at each cycle of nucleotide addition by treatment of the growing nucleotide chains on the solid support with a mild oxidation mixture. This oxidation step converts phosphorus (III) to the more stable phosphorus (V) oxidation state and prevents nucleotide chain scission at any subsequent deblocking or activation treatment steps by acid species such as dichloroacetic acid or trichloroacetic acid. Iodine is used as the oxidizing species with water as the oxygen donor. Preferred coreagents include tetrahydrofuran and lutidine. Following a wash of the solid support with anhydrous acetonitrile, the deblock/coupling/oxidation/capping cycle can be repeated as many times as necessary to prepare the oligonucleotide or oligonucleotides of choice, each time using the appropriate protected betacyanoethylphosphoramidite nucleoside to insert the nucleotide of choice carrying a purine or pyrimidine base. The purine bases preferably will be either adenine or quanine on the inserted nucleotide and the pyrimidine bases preferably will be cytosine or thymine. The simplicity of chemical synthesis of oligonucleotides has led to the development of practical guides for laboratory work and common use of commercial automated DNA synthesizers. See, M. H. Caruthers, "Gene synthesis machines: DNA chemistry and its uses", *Science* 230, (1985), 281–285; and J. W. Efcavitch, "Automated system for the optimized chemical synthesis of oligodeoxyribonucleotides" in Macromolecular Sequencing and Synthesis, Selected Methods and Applications (Alan R. Liss, Inc., New York), (1988), 221–234. Commercial instruments are available from several sources such as DuPont Company (Wilmington, Del.), Milligen/BioSearch, Inc. (San Rafael, Calif.) and Applied Biosystems (Foster City, Calif.). Instruments used in accordance with the present invention were the Biosearch 8700 or the Applied Biosystems 391 PCR-Mate DNA synthesis instruments. The operation of these instruments and the details of the beta-cyanoethylphosphoramidite chemistry cycles used with them is described in either the Biosearch, Inc. model 8600/8700 instruction manual or the PCR-Mate Model 391 DNA synthesizer user's manual (Applied Biosystems part number 900936, version 1.00, revision A dated May 1989).

The last coupling cycle of oligonucleotides can be completed leaving the 5' terminal dimethoxytrityl group on or off. The dimethoxytrityl group is preferably left on for convenience in subsequent purification of full-length oligonucleotides. The completed and protected oligonucleotides must be deprotected and cleaved from the solid support prior to purification. The solid support bearing the completed oligonucleotides is treated with fresh concentrated ammonium hydroxide at room temperature for at least one hour to cleave the oligonucleotides from the support resin. The solid support is then washed with more concentrated ammonium hydroxide and the combined concentrated ammonium hydroxide is incubated at 55°–60° C. for at least eight hours in a sealed vial in order to remove the protecting chemical functionalities from the protected bases. The sample is then cooled and evaporated to dryness under vacuum. The sample may also be reevaporated from fresh concentrated ammonium hydroxide or ethanol of at least 95% purity by volume. The final sample can then be stored in a lyophilized (dry) state or can be resuspended in sterile distilled water before storage at −20° C. See the PCR-Mate Model 391 user's manual, supra, and M. H. Caruthers et al., "Chemical Synthesis of Deoxyoligonucleotides by the Phosphoramidite Method," *Methods in Enzymology* 154, (1987), 287–313.

Any cleaved and deprotected oligonucleotides prepared by methodology drawn from the preferred choices above can be purified by one or more of several methods known in the art. These purification techniques include but are not limited to polyacrylamide gel electrophoresis, agarose gel electrophoresis, size exclusion chromatography, affinity chromatography, high performance liquid chromatography and hydrophobic interaction chromatography. The preferred method is selected from the group of purification techniques which consists of polyacrylamide gel electrophoresis, high performance liquid chromatography and hydrophobic interaction chromatography. One such preferred method is polyacrylamide gel electrophoretic purification of oligonucleotides, lacking a dimethoxytrityl moiety on the 5' terminus, on a vertical 12% polyacrylamide slab gel, 20×40×0.08 cm, in 7M urea, 90 mM Tris-HCl, pH 8.3, 90 mM borate, 1–2 mM disodium ethylenediaminetetraacetic acid (EDTA). A portion of each oligonucleotide to be purified (0.3–3.0 $A_{260}$ units) is evaporated to dryness under vacuum, resuspended in formamide:1 mM disodium EDTA (greater than 9:1) containing at least 0.01% bromophenol blue and at least 0.01% xylene cyanol, heated 2–3 minutes in a boiling water bath, quickly placed in an ice slurry and then loaded in an individual well (at least 6 mm in width). The sample(s) is electrophoresed at 80–90 W towards the anode until the bromophenol blue has migrated at least two-thirds the length of the polyacrylamide gel. The full-length oligonucleotides are then visualized by placing the polyacrylamide gel on a piece of flexible, clear plastic wrap such as Saran Wrap, placing it on top of a thin layer chromatography plate (e.g., Silica Gel F-254; Fisher Scientific Company, Pittsburgh, Pa.) containing a fluorescent indicator compound and examining the polyacrylamide gel under short wavelength ultraviolet light illumination. The full-length band material is then excised in polyacrylamide and can be purified out of the gel by various methods such as electroelution or simple diffusion in buffer. The preferred method of extraction is diffusion into 0.5 mL of 0.3M sodium acetate, pH 7.5, overnight with shaking and successive extractions of the aqueous phase with phenol:chloroform (1:1, v:v) and ethanol precipitation. The precipitated oligonucleotide can then be resuspended in an appropriate volume (usually in the range of 10–1000 microliters) of a suitable buffer such as 10 mM Tris-HCl, pH 7.5, 1 mM disodium EDTA or in sterile distilled water and stored at −20° C. See unit 2.12, "Purification of oligonucleotides using denaturing polyacrylamide gel electrophoresis," in *Current Protocols in Molecular Biology*, F. M. Ausubel et al., Eds., (1989).

An alternative more preferred method of purification and one well suited for purification of oligonucleotides still having a dimethoxytrityl moiety on the 5' terminus is high performance liquid chromatography (HPLC) on a reverse phase HPLC column. Such a reverse phase HPLC column can be packed with any of a variety of silica or polymer based resins which are commercially available from a number of vendors such as Millipore/Waters (Milford, Mass.), The Nest Group (Southboro, Mass.), Rainin Instrument Company, Inc. (Woburn, Mass.), J. T. Baker Inc. (Phillipsburg, N.J.), Alltech Associates Inc. (Deerfield, Ill.), or Pierce Chemical Company (Rockford, Ill.). Oligonucleotides are loaded, fractionated and eluted from such an HPLC column by, for example, an acetonitrile gradient in any of several suitable non-destructive buffers. Preferred acetonitrile gradients are in the range of 5% to 40% and more preferably in the range of 5% to 30% in 0.1M triethylammonium acetate, pH 7.0, buffer. Preferred reverse phase HPLC columns include those with linear alkyl chain moieties bound to them such as $C^4$, $C^8$, or $C^{18}$ alkyl chains. The appropriate fractions containing purified full-length oligonucleotide are then pooled, evaporated under vacuum and resuspended in 3% (v/v) acetic acid in water at room temperature for 10–30 minutes. The detrylated oligonucleotides are then ethanol precipitated or purified by other suitable means such as size exclusion chromatography. Alternatively, full-length detritylated oligonucleotides can also be purified by HPLC using various types of columns and gradient materials. For guidance, see G. Zon and J. A. Thompson, "A review of high-performance liquid chromatography in nucleic acids research," *BioChromatography* 1, (1986), 22–32.

Another alternative more preferred method is purification of the oligonucleotide by hydrophobic interaction chromatography. This purification technique for the purposes of the present invention is a form of reverse phase chromatography under atmospheric pressure over a hydrophobic resin. A crude oligonucleotide mixture in the ammonium hydroxide deprotection and cleavage solution is applied to the hydrophobic resin which has been equilibrated in a suitable buffer such as 1.0M triethylammonium acetate, pH 7.0. Bound oligonucleotides are then detrylated by exposure to 2% trifluoracetic acid for 1–3 minutes and then recovered in 15–40% acetonitrile in water. The recovered oligonucleotide is then lyophilized and resuspended as described above in a suitable buffer or sterile distilled water.

One or more synthetic oligonucleotides will be necessary to prepare a partially or completely synthetic gene for the purposes of the present invention. Any appropriate oligonucleotides and/or portions or all of a natural gene such as a natural magainin gene can be assembled into a gene encoding one or more AMPPPs by denaturing these DNAs by some means such as heating, mixing with a chaotropic agent such as urea or formamide or exposure to an alkaline solution. Phosphate moieties can be optionally attached enzymatically to any DNAs or oligonucleotides lacking them using an enzyme such as T4 polynucleotide kinase. See section 3.10 in *Current Protocols in Molecular Biology*, supra. Any oligonucleotides being used in the preparation of a gene within the scope of the present invention and in the presence or absence of any additional natural DNAs are then renatured or annealed by appropriate means, such as slow cooling to room temperature or dialysis to remove any chaotropic agents. These annealed DNAs can be linked covalently by treatment with a suitable enzyme such as T4 DNA ligase. See section 3.14 in *Current Protocols in Molecular Biology*, supra.

If necessary and where suitable, the gene products encoding peptides prepared by this means can be prepared for appending to genetic regulatory DNA sequences by treatment with restriction endonucleases according to manufacturer's specifications or by methods known in the art. See, for example, T. Maniatis et al., *Molecular Cloning*, supra, pp. 104–106.

The above procedures can be used for the production of genes encoding most or all antimicrobial peptides in accordance with the present invention, including RAMPPs or RAMPPPs, and oligopeptides. An alternative method of preparing genes encoding peptides and oligopeptides can also be used. This method would include preparing annealed DNAs coding for individual peptide subunits or for groups of individual subunits, including the gene segments encoding bridging molecules. It is also possible that the annealed DNAs, of which there are at least two, each would encode for some smaller portion of a peptide subunit so long as the composite gene which can be prepared from joining all such relevant individual annealed DNAs encodes the desired peptide without interruption.

The ends of the annealed DNAs would be chosen so as to allow bonding for overlapping and complementary short DNA sequences between ends of different DNA fragments. These bonding sites would also maintain the coding region for at least one peptide subunit into the next peptide subunit or the relevant bridging molecule without interruption when, at some later stage, the appropriate DNAs are annealed and ligated to form a larger gene encoding a peptide or oligopeptide. Two or more such DNA segments encoding various portions of a larger gene encoding, for example, an oligopeptide can be considered for attachment so as to maintain the appropriate DNA coding sequence, depending upon the size and composition of the desired final oligopeptide. The regions of overlapping and complementary ends on the smaller DNA segments can be chosen to be non-equivalent so as to prevent adventitious and undesirable joining of two or more DNA segments. These overlapping ends may or may not be equivalent to the product of treatment of precursor annealed DNAs with a restriction endonuclease as described above in the preparation of DNAs to be appended to genetic regulatory DNA sequences.

Those annealed DNA fragments which are meant to be joined into a larger DNA fragment encoding a larger oligopeptide within the scope of the present invention can be joined by gently annealing them by some means such as heating or exposure to an alkaline solution prior to reversal of the denaturation procedure. The method of annealing will preferentially not substantially denature the individual annealed DNAs during the process. The annealed DNAs can then be covalently joined by treatment with a suitable enzyme such as T4 DNA ligase. The appropriate DNA segments can be covalently joined to each other either simultaneously or in blocks which subsequently would go through at least one additional process of joining to form the final DNA fragment encoding the larger oligopeptide. If additional cycles or processes of DNA segment joining is needed prior to obtaining the final DNA fragment, the joined DNA segments obtained at intermediate stages of ligation should be purified by standard means such as purification by gel electrophoresis, through size exclusion chromatography and/or ethanol precipitation. See, for example, Chapter 2 of *Current Protocols in Molecular Biology*, supra. The final DNA fragment encoding a larger oligopeptide can then be appended to genetic regulatory DNA sequences as described above.

Genetic regulatory signals which are appended to genes encoding peptides so as to render them capable of expression as protein in a defined host cell may include gene promoter sequences, which are DNA sequences recognized by the biological machinery of the host cell and which induce transcription of the DNA sequence into messenger RNA (mRNA) by an RNA polymerase within the host cell. This mRNA must then be capable of being translated on ribosomes within the host cell into a protein product. The gene promoter sequences may be derived in part or in whole from promoter sequences found in cells unlike those of the host cell so long as they meet the above criteria for transcription and translation. For example, a vegetative gene promoter sequence from the gram-positive bacterium *Bacillus subtilis* may be satisfactory for expression of a peptide gene in the gram-negative bacterium *Escherichia coli*.

A second genetic regulatory element which may be appended to an AMPPP gene for the expression of one or more AMPPPs is a gene terminator or polyadenylation sequence. This DNA sequence contains genetic information that interrupts and halts further transcription, and, in the case of eucaryotic cells, provides information directing attachment of one or more adenosine nucleotides at the 3' end of the mRNA. A gene terminator sequence may represent in part or in whole a terminator sequence originating from the genome of the host cell or from the genome of some unlike cell that is known to be effective at appropriately terminating transcription within the host cell. An example of such a sequence would be the *Salmonella typhimurium his* operon rho-independent transcription terminator sequence (see, for example, M. E. Winkler, *Escherichia coli* and *Salmonella typhimurium: Cellular and Molecular Biology* [F. C. Neidhardt, Ed.-in-chief; American Society for Microbiology, 1987], chapter 25) or the octopine synthase terminator sequence from an *Agrobacterium tumefaciens* Ti plasmid (see, for example, H. DeGreve et al., "Nucleotide sequence and transcript map of the Agrobacterium tumefaciens Ti plasmid-encoded octopine synthase gene,", *J. Mol. Appl. Genet.* 1, (1982), 499–511).

A peptide expressing gene or genes with attached genetic regulatory signals is preferably introduced into a host cell of either procaryotic or eucaryotic origin for the intent of expressing the one or more peptides including AMPPPs encoded by the relevant genes. The means of introduction is well-described in the art and depends upon the type of host cell in which gene expression is being sought. For example, transformation of bacterial cells with externally supplied DNA such as cells of *Escherichia coli* can be accomplished by a calcium chloride procedure. Typically, the peptide gene or genes with attached genetic regulatory signals are covalently bound into a suitable transformation vector prior to the transformation procedure. Such vectors have been reviewed in Vectors: a Survey of *Molecular Cloning Vectors and Their Uses* by R. L. Rodriguez and D. T. Denhardt (Butterworths, Boston; 1988). See, also, T. Maniatis et al., *Molecular Cloning*, supra, pp. 247–255.

Once expressed with any such gene expression system in a suitable host cell, the peptide may be extracted and/or purified by conventional means and used against plant pathogens in either a partially purified or a substantially purified form. Methods of extracting peptide from host cells include heat and/or enzymatic lysis of the host cell, solubilization in a lipidic solvent or aqueous-organic micellar solution, and pressure rupturing of cell membranes and/or cell walls by forcing the host cells through a French press. The preferred method for cell lysis for the case of bacteria as host cells depends upon the scale of production being sought. For large scale production, heat or pressure rupturing of the bacterial cells is preferred. See, for example, H. Hellebust, "Different approaches to stabilize a recombinant fusion protein," Bio/Technology 7, (1989), 165–168. The extracted AMPPPs may be used in their immediate form without further purification or may be partially or completely purified by application of one or more fractionations of cellular contents by a method such as size exclusion chromatography, ion exchange chromatography, electrophoresis, affinity chromatography and the like.

Another possibility is to use totipotent plant cells as the host recipient for expressing those genes encoding peptides and expressing AMPPPs as protein product whereby the plant cells are capable of regenerating fertile crop plants. In this latter instance, the recipient plants are termed genetically transformed or transgenic plants. There are several known methods for introducing foreign genes into plants. The method of choice depends primarily on the type of crop plant that is to be transformed. However, many of these methods may be used in accordance with the present invention.

One method that is particularly efficient for the transfer of DNA into dicotyledonous plants involves the use of Agrobacterium. In this method the gene of interest (for example, a gene for an AMPPP with a Cauliflower mosaic virus 35S 5' promoter region and a 3' OCS terminator region) is inserted between the borders of the T-DNA region that has been spliced into a small recombinant plasmid with a selectable gene (for example, genes encoding neomycin phosphotransferase II (npt II) of transposon Tn5, phosphinothricin acetyltransferase, and the like). The recombinant plasmid is then introduced into an Agrobacterium host either by direct transformation or by triparental mating. The Agrobacterium strain carrying the gene of interest is then used in transformation of dicot plant tissue by co-culturing the bacterium with the plant sample (e.g., leaf disc) for a period of 2–3 days. Transformed cells are recovered by selection on the appropriate agent and plants can then be regenerated. See, R. B. Horsch et al., "A Simple and General Method of Transferring Genes into Plants," *Science* 227, 1985), 1229–1231.

Other methods that have been used in the transformation of plant cells, and in particular on the more recalcitrant monocotyledonous crop plants, include chemically induced transfer (e.g., with polyethylene glycol; see H. Lorz et al., "Gene transfer to cereal cells mediated by protoplast transformation." *Mol. Gen. Genet.* 199, (1985), 178–182), biolistics (W. J. Gordon-Kamm et al., "Transformation of Maize Cells and Regeneration of Fertile Transgenic Plants," *The Plant Cell*, 2, (1990), 603–618), microinjection (G. Neuhaus et al., "Transgenic rapeseed plants obtained by microinjection of DNA into microspore-derived proembryoids," *Theor. Appl. Genet.*, 74, (1987), 30–36) and others (I. Potrykus, *Bio/technology* 9, (1990), 535–542.

As described by Bascomb et al., supra, proteins produced in nature often comprise a Met amino acid bonded to the amino or N-terminal end. These methionines are sometimes formylated, "(f)Met". Therefore, the proteins disclosed herein can also be produced with a methionine or N-formylated methionine appended to the N-terminus. ("Met-proteins")

SIGNAL PEPTIDES

Since pathogens normally attack cells, and in particular, plant tissue from locations outside the cell, it is likely that the proteins intended to protect host plant cells will need to be secreted from the cell. This may be accomplished by appending a peptide sequence known in the literature as a targeting peptide (G. von Heijne "The Signal Peptide" *J. Membrane Biol.* 115, (1990), 195–201; S. F. Nothwehr and J. I. Gordon "Targeting of Proteins into the Eukaryotic Secretory Pathway: Signal Peptide Structure/Function Relationships" *Bioassays*, 12, (1990) 479–484; and K. Verner and G. Schatz, "Protein Translocation Across Membranes", *Science*, 24, (1988), 1307–1313) to the N-terminus of the peptide.

A targeting or signal peptide is one that when attached to the N-terminus of another peptide or protein is instrumental in directing that peptide or protein to a specific sub-cellular compartment and preferably into the extra-cellular space. Examples of targeting or signal peptides in accordance with the present invention are those of carrot extensin (SEQ ID NO. 21) (J. Chen and J. E. Varner "An Extracellular Matrix Protein in Plants, Characterization of a Genomic Clone for Carrot Extensin" *Embo J.*, 4, (1985) 2145–51) and barley alpha-amylase (SEQ ID NO. 22) (J. C. Rogers and C. Milliman "Isolation and Sequence Analysis of a Barley Alpha-Amylase cDNA Clone" *J. Biol. Chem.* 258, (1983), 8169–74; T. H. D. Ho. et al., "Regulation of Gene Expression in Barley Aleurone Layers" in *Molecular Biology of Plant Growth Control*, Alan R. Liss, Inc., (1987), pp. 35–49; C. R. P. Knox et al., "Structure and Organization of Two Divergent Alpha-Amylase Genes from Barley", *Plant Mol. Biol.*, (1987), 9, 3–17; and B. Khursheed and J. C. Rogers "Barley Alpha-Amylase Gene:Quantitative Comparison of Steady-State mRNA Levels from Individual Members of the Two Different Families Expressed in Aleurone Cells", *J. Biol. Chem.*, 263 (1988), 18953–18960).

Preferred for use in this invention is the carrot extensin signal peptide. For the reasons discussed supra, the targeting peptide will normally have either a methionine or a formylated methionine appended to its N-terminus. The appendage of a targeting peptide to peptides or oligopeptides in accordance with the present invention, either with or without a methionine or an N-formylated methionine attached to its N-terminus, should have no effect upon the efficacy of the peptide, because the targeting peptide normally would be cleaved from the peptide by proteases during transport to the extracellular space.

Exemplary peptides within the scope of the present invention which contain signal peptide sequences appended to the N-terminus of AMPPPs are (SEQ ID NO. 21)-(SEQ ID NO. 1)-(SEQ ID NO. 1);

(SEQ ID NO. 21)-(SEQ ID NO. 1)-(SEQ ID NO. 6);

(SEQ ID NO. 21)-(SEQ ID NO. 2)-(SEQ ID NO. 5)-(SEQ ID NO. 2);

(SEQ ID NO. 21)-(SEQ ID NO. 1)-(SEQ ID NO. 5)-(SEQ ID NO. 1); and (SEQ ID NO. 21)-(SEQ ID NO. 2)-(SEQ ID NO. 5)-[(SEQ ID NO. 10)-(SEQ ID NO. 5)]$_3$-(SEQ ID NO. 1)-(SEQ ID NO. 5)-(SEQ ID NO. 10); wherein for (SEQ ID NO. 5) $Xaa^1$–$Xaa^5$ are Gly.

When the signal peptides of the above oligopeptides are cleaved following expression and excretion into the extracellular space, the released oligopeptides are available in the event of an invasion of the host plant by a microbial pathogen.

THE USE OF PEPTIDES AND OLIGOPEPTIDES

Antibiotic peptides embodied by the present invention can have wide use in a number of everyday situations where one desires to inhibit the growth or survival of microbes. The present inventors are particularly interested in the application of AMPPPs in enhancing crop yields by reducing the economic impact of crop destruction brought about by plant microbial pathogens. However, AMPPPs of the present invention may also be valuable as pharmaceutical reagents in the treatment of human or animal disease caused by microbes, as additives to foodstuffs for the purpose of food preservation during storage or shipping, as domiciliary or medical disinfectants, or as a preservative in cosmetic, pharmaceutical or other products. AMPPs or AMPPPs of the present invention could be useful in any or all of these contexts either by themselves or in combination with other chemical or pharmaceutical compounds which are effective against microbial pathogens of humans, animals or plants.

EXTERNAL APPLICATION OF PEPTIDES AND OLIGOPEPTIDES

If an external application of the peptides and oligopeptides of the present invention is to be used to protect, for example, a plant against pathogens, it would be expected that the AMPPPs used would be diluted to form a liquid solution or suspension containing between 1–1000 micrograms/mL of the AMPPPs or mixed with a diluent solid to be applied as a dust. The precise nature of application will depend in part on the particular pathogens being targeted. Detailed methods for adapting general methods of application to specific crops and pathogens can be found in *Methods For Evaluating Pesticides For Control of Plant Pathogens*, K. D. Hickey, Ed., The American Phytopathological Society (St. Paul, Minn.), 1986. Methods of application that are expected to be particularly useful in accordance with this aspect of the present invention include intermittent aqueous and non-aqueous sprays of the entire plant or parts thereof, seed coatings, and inclusion in irrigation systems (e.g., greenhouse mistbenches). Adjuncts that could be added to the formulation would include agents to aid solubilization, wetting agents and stabilizers, or agents that would produce a microencapsulated product. The formulation should preferably not contain high concentrations of inorganic salts and particularly not divalent cations such as $Ca^{++}$, $Mg^{++}$, or $Fe^{++}$. External applications could also utilize recombinant microorganisms in either a viable form or after being converted into a non-viable form by a method that does not inactivate the AMPPPs. If viable recombinant organisms are used to deliver the AMPPPs, it would be preferable if they had the ability to colonize the target plant.

PHYTOTOXICITY SCREENING OF PEPTIDES WITH CULTURED PLANT CELLS

Bascomb et al., supra, disclosed a screening technique for antimicrobial peptides which utilized isolated plant chloroplasts. The effect of these antimicrobial peptides on the chloroplasts was a general indication of the potential phytotoxicity associated with the presence and possible expression of a particular peptide in plant tissue. Bascomb et al., supra, also disclosed the desirability of utilizing antimicrobial peptides which have a minimum level of phytotoxicity. However, while this screening technique has several advantages as an indicator of phytotoxicity it is inconvenient in that it requires the collection and use of chloroplasts. Furthermore and because of the fact that the screening process is only intended as a general indicator of phytotoxicity, the data generated are not necessarily predictive of toxicity to specific plant cells or plant tissue with which an AMPPP RAMPPP or oligopeptide is to be used. Specifically, the phytotoxic effect of a particular antimicrobial peptide on a chloroplast, because of the chloroplast's unique structure and membrane chemistry, is not necessarily an indication of the phytotoxicity of the antimicrobial peptide against chemically dissimilar plant plasma membranes or membranes of other subcellular organelles.

The present inventors have discovered a new screening method employing cultured plant cells which is more efficient than prior phytotoxicity screening methods because it does not require the use of isolated chloroplasts. Furthermore, the screening technique of the present invention is a more accurate reflection of the phytotoxic effects of an antimicrobial peptide against, for example, a host cell's membrane chemistry. Furthermore, the metabolic end point used in accordance with the present invention is oxygen consumption, rather than oxygen evolution as determined with isolated chloroplasts assays. Therefore, it is possible, through the use of the present invention, to obtain data on the phytotoxic impact of various antimicrobial peptides on different metabolic pathways.

While the assay in accordance with the present invention is described in terms of plant cells, it is understood that the technique is also applicable to other types of cells as well. Another advantage in accordance with this aspect of the present invention is the ability to test the phytotoxic effect of specific antimicrobial peptides on specific host plant cells. Therefore, if one were intending to produce, for example, a transgenic maize of a particular genotype which contains a gene which could express a particular antimicrobial peptide, it would be possible to test the phytotoxic effect of this peptide on the maize plant cells prior to genetic engineering. The compatibility of the potential host cell and/or host tissue and the antimicrobial peptide would therefore be approximated.

With reference to plant cells, a measure of the relative phytotoxicity of a peptide to a plant cell or plant tissue may be determined by testing the peptide against any cell culture regularly maintained as a cell suspension. Cultured whole cell suspensions may be produced using standard methods for initiating and maintaining cell suspensions such as those discussed in the Handbook of *Plant Cell Culture*, Vols. 1–3, (Macmillan Publishing Company, New York, N.Y., 1983–84). A phytotoxic response can be demonstrated in a cell line by observing the effect of a particular peptide on oxygen consumption. In particular, a dose response relationship can be inferred for any peptide if it can be demonstrated that incubating increasing concentrations of that peptide with a determined number of suspension cells leads to a decreased oxygen consumption.

Likewise, a dose response relationship can be inferred for a given peptide if it can be demonstrated that incubation of a single concentration of a peptide with increasing numbers of cultured whole cells leads to an overall decreased inhibition of oxygen consumption. A cuvette assay is generally used in these determinations.

Solutions used in the cuvette to actually test percent inhibition of whole cell oxygen consumption may include simply water to which the peptide is added or it may consist of any standard solution in which cell suspension cultures are grown to which peptide is added. These solutions may include sugars such as sucrose, glucose, fructose, xylose and arabinose. Any combination of inorganic salts may be included such as ammonium chloride, ammonium nitrate, ammonium phosphate, ammonium sulfate, boric acid, calcium chloride, calcium nitrate, calcium phosphate, cobalt chloride, cupric sulfate, ethylenediaminetetraacetic acid, ferric chloride, ferric citrate, ferric sulfate, ferric tartrate, ferrous sulfate, magnesium sulfate, manganese chloride, manganese sulfate, molybdenum trioxide, molybdic acid, nickel chloride, nickel sulfate, potassium chloride, potassium iodide, potassium nitrate, potassium phosphate, potassium sulfate, sodium nitrate, sodium phosphate, sodium sulfate, zinc nitrate, and zinc sulfate. Likewise, any combination of organics may be included such as activated charcoal, adenine hemisulfate, aminobenzoic acid, 6-benzylaminopurine, D-biotin, calcium pantothenate, choline chloride, dimethylallylamino purine, folic acid, glycine, indole-3-acetic acid, myo-inositol, indole-3-butyric acid, kinetin, alpha-naphthaleneacetic acid, nicotinamide, nicotinic acid, peptone, pyridoxine HCl, riboflavin, thiamine HCl, vitamin A, vitamin B12, and vitamin D. Mixtures of any or all of the above agents may be useful. When included, the concentration of each agent is generally present in amounts between 0 and 1 molar. Buffering agents may also be included in the cell solutions to maintain the solution pH in the preferred range of 4 to 9. Examples of these buffers are Tris (tris-[hydroxymethyl]aminomethane), MES (s-[N-morpholino]-ethane sulfonic acid), acetate salts, and HEPES (N-[2-hydroxyethyl]piperazine-N-[2-ethanesulfonic acid]). When used, these buffers are generally present in the amount of 0.01% to about 10% (w/v). The total volume of cell suspension to be tested in the described phytotoxicity assay could range from 10 microliters to 1 milliliter. The actual amount of cells useful in the present invention may range from a low of only a few cells per cuvette to a high limited by the size of the cuvette and the necessity of constant agitation of the cell suspension by a magnetic stirrer. The lowest number of cells which can be tested is the number which consumes a recordable amount of oxygen. This consumption could be monitored by a variety of techniques and instruments available in the art such as a Warburg apparatus or, preferably, an oxygen electrode. See "The Use of the Oxygen Electrode and Fluorescence Probes in Simple Measurements of Photosynthesis," D. Walker, 1987, Hansatech Ltd., Kings Lynn, Norfolk, England.

It is also possible in accordance with the present invention to use plant cell protoplasts for testing. A protoplast as used herein is a plant cell which has had its cell wall removed. This may be accomplished enzymatically by use of lignases, cellulases or other known enzymes, or by mechanical means such as tissue slicing combined with osmotic shock. The use of isolated protoplasts allows for the realization of many of the advantages of the screening technique in accordance with the present invention except for the additional time and labor required for preparing a protoplast as a reagent for the measurement. Furthermore, there is a loss of the ability to measure the potential interaction between the cell wall and the particular antimicrobial peptide.

The following examples are offered for the purpose of further illustrating the concepts of the present invention. They are not intended to be limiting.

These examples make reference to a number of peptides including RAMPPPs and oligopeptides throughout. For convenience, these peptides have been assigned an arbitrary number which will be used to reference the compounds identified in Table I.

TABLE I

| Peptide No. | Peptide | SEQ ID NO. |
|---|---|---|
| 1 | Magainin 2 | (SEQ ID NO. 2) |
| 2 | Magainin 1 | (SEQ ID NO. 1) |
| 3 | Cecropin A-NH$_2$ | (SEQ ID NO. 8) |
| 5 | P1 (head-to-tail) | (SEQ ID NO. 6)-SEQ ID NO. 2) |
| 6 | Mag 2 dimer (bridged) | (SEQ ID NO. 2)-(SEQ ID NO. 5)-(SEQ ID NO. 2) |
| 7 | PGL$^c$ | (SEQ ID NO. 7) |
| 8 | Reverse Magainin 2 | (SEQ ID NO. 10) |
| 9 | Met-Mag 1 dimer (head-to-tail) | Met-(SEQ ID NO. 1)-(SEQ ID NO. 1) |
| 10 | [Glu 8] Mag 2 | (SEQ ID NO. 3)** |
| 11 | Met[Arg 7, Glu 8, Des Ser 23] Mag 1 | Met-(SEQ ID NO. 3)** |
| 12 | Met [Arg 7, Glu 8, Pro 23] Mag 1 | Met-(SEQ ID NO. 20) |
| 13 | Cys [Arg 7, Glu 8, Pro 23] Mag 1 | Cys-(SEQ ID NO. 20) |
| 14 | Dislufide linked peptide No. 13s | (SEQ ID NO. 20)-S-S-(SEQ ID NO. 20) |
| 15 | Head-to-tail peptide Nos. 11 and 12*** | (SEQ ID NO. 3)**-(SEQ ID NO. 20) |
| 16 | Met-head-to-tail peptide Nos. 4 and 12*** | Met-(SEQ ID NO. 6)-(SEQ ID NO. 20) |
| 17 | Met-peptide No. 16 | Met-(SEQ ID NO. 6)-(SEQ ID NO. 20) |
| 18 | Reverse Magainin 1 | (SEQ ID NO. 9) |
| 19 | Ser-Magainin 2 | Ser-(SEQ ID NO. 2) |

**Indicates the most closely related (SEQ ID NO.)
***Indicates the omission of the N-terminal Met of this peptide monomer.
Xaa$^1$-Xaa$^5$ of (SEQ ID NO. 5) are each Gly.

EXAMPLE 1

Preparation of Peptide No. 5 t-Boc-(Mag 2)-OCH$_2$PAM resin was prepared using an ABI Model 430A peptide synthesizer employing t-Boc protection, DCC/HOBT produced active esters in NMP and Glu(OBzl), His(Bom), Lys(Cl-Z) and Ser(Bzl) as side chain protecting groups. The synthesis was started from 0.5 mmol (740 mg) of t-Boc-Ser(Bzl)-OCH$_2$PAM resin (substitution level=0.68 mmol/g), which was subjected to repetitive deprotection, neutralization and coupling steps following the standard NMP/t-Boc chemistry cycles used by the instrument. At the completion of each coupling step a sample of the resin was taken for ninhydrin monitoring (see Sarin et al., supra), which showed coupling efficiencies of greater than 98.4% at each step.

About two-thirds of the resin was removed for use in the synthesis of Mag 2-OH (Peptide No. 11, Example 13) and (Mag 2)-(Gly)$_5$-(Mag 2)-OH (Peptide No. 6, Example 2). The synthesis of t-Boc-(Mag 2)-(Mag 2)OCH$_2$PAM resin was then completed in the same manner except that double couplings were used for the synthesis of the last 19 amino acids. The yield of t-Boc-(Mag 2)-(Mag 2)OCH$_2$PAM was 0.690 g.

The N-terminal t-Boc group was removed by the peptide synthesizer using TFA, and the peptide was then deprotected and cleaved from the resin using the following low/high HF procedure: 0.39 g of the peptide-PAM resin mixture was stirred for two hours at 0° C. with a solution of 1.0 mL of anhydrous HF, 2.6 mL of DMS and 0.4 mL of p-cresol. After evaporation of the HF and DMS, the peptide-resin mixture was stirred with a fresh solution of 7 mL of anhydrous HF, 0.5 mL of anisole, 0.3 mL of DMS, 0.2 mL of 1,2- ethanedithiol and 3.0 mg of 2-mercaptopyridine for 30 min. at −10° C. and 30 min. at 0° C. After evaporation of the HF and other volatiles, the resin was swollen with chloroform and the mixture was washed with 3×5 mL of ether, stirred for 30 minutes with 3 mL of BME and extracted with 3×3 mL of 1:1 15% acetic acid/BME, and once with 15 mL of 50% aq. acetonitrile containing 0.1% TFA. The aqueous extracts were combined, extracted with 3×10 mL of ether and lyophilized to provide 152 mg (about 65%) of a peptide mixture. The crude peptide was dissolved in about 4 mL of 1N acetic acid containing 1% BME and passed through a 2.6×10 cm Bio-Rad AG 1X-8 ion exchange column (acetate form) in 1N acetic acid in order to remove fluoride salts and convert the peptide to its acetate salt form. The peptide fractions, detected by ninhydrin monitoring (Sarin et al., supra), were combined and lyophilized to give 122 mg of peptide. The peptide was then dissolved and stirred in 40 mL of 10% ammonium bicarbonate for 24 hrs. under a nitrogen atmosphere at room temperature. The solution was lyophilized and the residue was repeatedly freeze-dried from 1N acetic acid containing 1% BME to finally give 199 mg of peptide.

Final purification was accomplished by preparative, reversed phase HPLC using repetitive injections of peptide (10–15 mg) into a 2.2×25 cm, 10 micron, 300 angstrom, Vydac C-4 column and elution with the following linear gradient: 0% B to 60% B in A over 60 min; flow rate 6.0 mL/min; solvent A: 0.1% TFA; solvent B: 0.08% TFA in acetonitrile; monitoring: UV absorbance at 235 nm. The main peak eluting at 51.7 min, presumably the undecatrifluoroacetate form of the peptide, was collected and shown to be greater than 95% pure by HPLC. The structure was confirmed by FAB-MS: theoretical $(M+H)^+$ in amu: 4917.3; observed: 4917.8.

EXAMPLE 2

Preparation of peptide No. 6 t-Boc-(Mag 2)-OCH$_2$PAM resin (680 mg) was prepared as in Example 1 and the rest of the peptide was appended using the same procedure except that the amino acids of the second Mag 2 unit were added using double couplings. The yield of t-Boc-(Mag2)-(Gly)$_5$-(Mag2)-OCH$_2$PAM resin was 737 mg. After removal of the t-Boc group, deprotection and cleavage of 563 mg of the peptide resin using the same procedure as in Example 1 afforded 204 mg of crude peptide. Ion exchange of this material as in Example 1 afforded 168 mg of peptide, which, after ammonium bicarbonate treatment as in Example 1, resulted in 205 mg of peptide. Final purification was performed using preparative HPLC as in Example 1 except that 10–20 mg injections and the following program were used: linear gradient of 20% B in A to 40% B in A over 60 min followed by 40% B in A for 20 min. The main peak eluting at 69.3 min, presumably the undecatrifluoroacetate form of the peptide, was collected and shown to be greater than 85% pure by HPLC. The structure was confirmed by FAB-MS: theoretical $(M+H)^+$ in amu: 5202.6; observed 5201.6

EXAMPLE 3

Preparation of Peptide No. 7 t-Boc-PGL-OCH$_2$PAM resin was prepared from 0.5 mmol (661 mg) of t-Boc-Leu-OCH$_2$PAM resin (substitution level=0.76 mmol/g) using the procedure of Example 1 and double couplings after the eleventh amino acid. The yield of PGL-OCH$_2$PAM resin was 1.61 g. After removal of the t-Boc group, deprotection and cleavage of 1.59 g of this resin was performed by stirring for 30 min. at −10° C. and then 30 min at 0° C. in a solution of 18.0 mL of anhydrous HF, 1.5 mL of anisole, 0.6 mL of DMS, 0.3 mL of 1,2-ethanedithiol and 3.0 mg of 2-mercaptopyridine. After evaporation of the HF and DMS at 0° C., the peptide/resin/scavenger mixture was washed with 3×15 mL of cold 99:1 ether/BME to remove scavengers and other by-products. The residue was stirred with 5 mL of BME and then extracted with 3×10 mL of 15% acetic acid/2% BME. The extracts were combined and, in turn, extracted with 2×20 mL of ether. The acetic acid layer was then lyophilized to provide 559 mg (71%) of crude peptide. After ion exchange and treatment with ammonium acetate as in Example 1, final purification was obtained using preparative HPLC as in Example 1 except that a gradient of 24% B in A to 44% B in A over 40 min was used. The main peak eluting at 27.1 min, presumably the pentatrifluoroacetate form of the peptide, was collected and shown to be greater than 98% pure by HPLC. The structure was confirmed by FAB-MS: thoretical $(M+H)^+$ in amu: 1970.2; observed: 1970.1.

EXAMPLE 4

Preparation of Peptide No. 8 t-Boc-R-Mag 2-OCH$_2$PAM resin was prepared from 0.5 mmol (653 mg) of t-Boc-Gly-OCH$_2$PAM resin (substitution level=0.77 mmol/g) using the procedure of Example 1 except that, after the synthesis of t-Boc-[Ala$^{15}$-Gly$^{23}$]R-Mag2-OCH$_2$PAM resin, about half of the resin was removed for use in the synthesis of R-Mag 1-OH (peptide #18). The yield of t-Boc-R-Mag 2-OCH$_2$PAM resin was 1.17 g. After removal of the t-Boc group, deprotection and cleavage of this resin was performed using the procedure given in Example 3 to provide 473 mg (76%) of crude peptide. Ion exchange of 200 mg of this material followed by ammonium bicarbonate treatment as described in Example 1 resulted in 158 mg of peptide. Final purification was performed by HPLC using the procedure of Example 1 except that a gradient of 24% B in A to 44% B in A over 40 min was used. The main peak eluting at 27.9 min, presumably the hexatrifluoroacetate form of the peptide was collected and shown to be greater than 98% pure by HPLC. The structure was confirmed by FAB-MS: theoretical $(M+H)^+$ in amu: 2467.4; observed: 2467.5. "R-Mag 2" indicates a RAMPPP of Magainin 2.

EXAMPLE 5

Preparation of Peptide No. 9 t-Boc-Met-(Mag 1)-(Mag 1)-OCH$_2$PAM resin was prepared from 0.5 mmol (714 mg) of t-Boc-Ser(Bzl)-OCH$_2$PAM resin (substitution level=0.71 mmol/g) using the procedure of Example 1 except that, after the assembly of the first magainin 1 unit, about half of the resin was removed for use in the preparation of Mag 1-OH, (peptide No. 2) and the rest of the amino acids were appended using double couplings. The yield of t-Boc-Met-(Mag 1)-(Mag 1)-OCH$_2$PAM resin was 1.50 g. After removal of the t-Boc group, deprotection and cleavage of this resin was performed using the procedure described in Example 1 to give 796 mg (82%) of crude peptide. After ion exchange and ammonium bicarbonate treatment as in Example 1, final purification was performed by HPLC using the procedure of Example 1 except that a gradient of 27% B in A to 47% B in A over 60

59 min was used. The main peak eluting at 42.4 min, presumably the undecatrifluoracetate form of the peptide was collected and shown to be greater than 97% pure by HPLC. The structure was confirmed by FAB-MS; theoretical (M+H)$^+$ in amu: 4933.3; observed: 4931.9.

EXAMPLE 6

Preparation of Peptide No. 12 t-Boc-Met [Arg$^7$, Glu$^8$, Pro$^{23}$] Mag 1-OCH$_2$PAM resin was prepared from 0.61 mmol (763 mg) of t-Boc-Pro-OCH$_2$PAM resin (substitution level=0.80 mml/g) using the method of Example 5 except that about half of the resin was removed after the synthesis of the fragment t-Boc (9-23) [Pro$^{23}$] Mag 1-OCH$_2$PAM resin. Completion of the synthesis followed by removal of the t-Boc- group resulted in 1 366 g of Met[Arg$^7$, Glu$^8$, Pro$^{23}$] Mag 1-OCH$_2$PAM resin. Deprotection and cleavage of 719 mg of this resin using the procedure of Example 1 provided 25 mg of the crude peptide. After ion exchange using the procedure of Example 1, the peptide was purified by HPLC using the procedure of Example 1 except that a gradient of 24% B in A to 44% in A over 40 min was used. The major peak eluting at 34.1 min, presumably the hexatrifluoroacetate form of the peptide, was collected and shown to be greater than 95% pure by HPLC. The structure was confirmed by FAB-MS; theoretical (M+H)$^+$ in amu: 2612.4; observed: 2612.0.

EXAMPLE 7

Preparation of Peptide No. 13 t-Boc [Arg$^7$, Glu$^8$, Pro$^{23}$] Mag 1-OCH$_2$PAM resin was prepared from 0.606 mmol (0.758 g) of t-Boc-Pro-OCH$_2$-Pam resin (substitution level=0.80 mmol/g) using the procedure of Example 1. At the completion of the synthesis, approximately two thirds of the peptide-resin was removed and set aside for use in Examples 9, 10 and 11. The remaining one third was coupled with t-Boc-Cys(4-MeBzl) and subjected to TFA deprotection to produce the desired Cys(4-MeBzl)-Pro$^{23}$-OCH$_2$PAM resin. This was then deprotected and cleaved using the low/high HF procedure described in Example 1 to give 260 mg (73%) of peptide, which was converted to the acetate form as described in Example 1. Final HPLC purification was performed using the method described in Example 1, except that a linear gradient from 25% to 45% B in A over 60 minutes was instead used. The main peak eluting at 49.1 minutes, presumably the hexatrifluoroacetate form of the peptide, was collected and shown by HPLC analysis to be greater than 90% pure. The structure was confirmed by FAB-MS; theoretical (M+H)$^+$ in amu: 2584:4; observed: 2583.9.

EXAMPLE 8

Preparation of Peptide No. 14

This peptide dimer is prepared by oxidation of Peptide No. 13 (see Hodges et al., supra), by stirring a solution of Peptide No. 13 (3.2×10$^{-4}$M, 10 mg/mL) in a phosphate buffer of Cu$^{2+}$(0.05M NaH$_2$PO$_4$, 1.6×10$^{-5}$M CuCl$_2$, 0.5M NaCl, pH=7.0) overnight (12–20 h) at room temperature in air. The solution is then desalted by elution of the concentrated reaction mixture through a Sephadex G-25 column (2.6×25 cm) with 10% acetic acid. Final purification is performed by preparative HPLC as described for Peptide No. 16.

60

EXAMPLE 9

Preparation of Peptide No. 15

The desired peptide-PAM resin (1.05 g) was prepared using double couplings and the procedure described in Example 13 starting from about one-third of the t-Boc-[Arg$^7$, Glu$^8$, Pro$^{23}$] Mag 1-OCH$_2$PAM resin prepared in Example 7. After removal of the t-Boc group, deprotection and cleavage using the procedure described in Example 1 provided 562 mg (84%) of the crude peptide. Ion exchange and HPLC purification were performed as in Example 1 except that a gradient of 40% B in A to 60% B in A over 60 min was used. The main peak eluting at 43.8 min, presumably the undecatrifluoroacetate form of the peptide, was collected and shown to be greater than 95% pure by HPLC. The structure was confirmed by FAB-MS.

EXAMPLE 10

Preparation of Peptide No. 16 t-Boc-P1-[Arg$^7$, Glu$^8$, Pro$^{23}$Mag] 1-OCH$_2$PAM resin (1.40 g) was prepared using double couplings, Trp(CHO) and the procedure described in Example 1 starting from about one-third of the t-Boc-[Arg$^7$, Glu$^8$, Pro$^{23}$] Mag 1-OCH$_2$PAM resin prepared in Example 7. After removal of the t-Boc group, deprotection and cleavage of 681 mg of peptide-resin using the procedure described in Example 1 (except that 3 mg of skatole was also added to the high HF solution) provided 347 mg of crude peptide, which was purified by ion exchange chromatography and treatment with ammonium bicarbonate as in Example 1. Analysis of the product was performed by HPLC on a 2.2 mm×25 cm, 300 Ångstrom Vydac C-18 column using a gradient of 30% B in A to 65% B in A over 40 min (flow rate equals 1 mL per min). The analysis showed that the main peak, presumably the dodecatrifluoroacetate form of the peptide, eluted at 19 min. The structure was confirmed by FAB-MS.

EXAMPLE 11

Preparation Of Peptide No. 17

Using the procedure described in Example 1, t-Boc-Met was double coupled to 740 mg of the t-Boc-P1-[Arg$^7$, Glu$^8$, Pro$^{23}$] Mag 1-OCH$_2$PAM resin prepared in Example 10. After removal of the t-Boc group, and the procedure described in Example 10, deprotection and cleavage of 741 mg of the peptide-resin afforded 305 mg (66%) of the crude peptide. Purification of the peptide was performed as in Example 1, except that a gradient of 35% B in A to 55% B in A over 60 min was used. The main peak eluting at 57.5 min, presumably the dodecatrifluoroacetate form of the peptide, was collected and shown to be greater than 90% pure by HPLC. The structure was confirmed by FAB-MS.

EXAMPLE 12

Preparation of peptide No. 18 t-Boc-R-Mag 1-OCH$_2$PAM resin (930 mg) was prepared using the procedure describe in Example 1 starting from the remainder of the t-Boc[Ala$^{15}$-Gly$^{23}$]R-Mag 2-OCH$_2$PAM resin prepared in Example 4. After removal of the t-Boc group, deprotection and cleavage of 920 mg of the peptide-resin using the procedure described in Example 1 provided 296 mg of crude peptide. Purification of the peptide was performed as in Example 4 except that a gradient of 20% B

EXAMPLE 13

Preparation of Peptide No. 11 t-Boc-Met[Arg$^7$, Glu$^8$, Des Ser 23] Mag 1-OCH$_2$PAM resin was prepared from 0.6 mmol (923 mg) of t-Boc-Lys(Cl-Z)-OCH$_2$PAM resin (substitution level=0.65 mmol/g) using Arg(Mts) and the procedure in Example 1 except after the synthesis of fragment [Glu$^8$-Lys$^{22}$, Des Ser 23] Mag 1-OCH$_2$PAM resin, about two-thirds of the resin was removed. At the end of the synthesis after t-Boc removal, 622 mg of [Arg$^7$, Glu$^8$, Des Ser $^{23}$] Mag 1-OCH$_2$PAM resin was obtained. Deprotection and cleavage of 593 mg of this material using the procedure described in Example 3 provided 237 mg (73%) of the crude peptide. After ion exchange chromatography and ammonium bicarbonate treatment using the procedure described in Example 1, final purification was performed by HPLC also using the procedure of Example 1 except a linear gradient of 25% B in A to 45% B in A over 40 min was used. The main peak eluting at 32.6 min, presumably the hexatrifluoroacetate form of the peptide, was collected and shown to be greater than 96% pure by HPLC. The structure was confirmed by FAB-MS; theoretical (M+H)$^+$ in amu: 2515.4; observed: 2515.7.

EXAMPLE 14

Preparation of Peptide Nos. 1, 2, 3, 4 and 10

Magainin 2-OH (Peptide No. 1) and Magainin 1-OH (Peptide No. 2) were purchased from Applied Biosystems, Inc., Foster City, Calif. or were made as described in Bascomb et al., supra. [Glu$^8$] Mag 2-OH (Peptide No. 10) was prepared as described in Bascomb et al., supra. Cecropin A-NH$_2$ (Peptide No. 3) was purchased in the form of its trifluoroacetate salt from Star Biochemicals, Inc., Torrance, Calif.. P1-OH, also known as Cecropin P1-OH (Peptide No. 4), was purchased from Peninsula Laboratories, Inc., Belmont Calif., catalogue #6300.

EXAMPLE 15

Preparation of Peptide No. 19 t-Boc-Ser-Mag 2 was prepared as in Example 1 except that DCC-promoted symmetrical anhydride formation protocols in DMF and double couplings after the eleventh amino acid were used. Deprotection and cleavage of 875 mg of this resin using the same procedure as in Example 3 provided 360 mg of crude peptide. After ion exchange and ammonium bicarbonate treatment using the methods described in Example 1, the peptide was reduced with N-methylmercaptoacetamide (MMA) using the procedure of A. Culwell, supra. A solution of the resulting oily residue in 10% acetic acid/1% BME was passed through a 2.6×70 cm Sephadex G25 column at a flow rate of 1 mL/min and the peptide fractions were detected by monitoring the effluent at 254 nm. These were combined and lyophilized to provide MMA free peptide in nearly a quantitative yield. Final purification was performed by HPLC using the procedure of Example 1 except that a gradient of 22% B in A to 42% B in A over 40 min was used. The main peak eluting at 31.7 min, presumably the hexatrifluoracetate salt form of the peptide was collected and shown to be greater than 90% pure. The structure was confirmed by amino acid analysis.

EXAMPLE 16

Antifungal Bioassay

Fungi were grown on an appropriate medium, in this case a potato dextrose agar plate, for several weeks. At the end of that period, the plate was flooded with about 5 mL of sterile distilled water to harvest spores. The spore concentration was determined by use of a hemocytometer and the spore suspension was stored in a sterile tube at 4° C. until it was needed. Then 82 microliters of potato dextrose broth and 3 microliters of spore suspension (ranging from 10$^5$ to 10$^7$ spores total) were added to 12 wells in a 96 well microtiter plate for each AMPPP to be tested, with 1–4 replicate sets of 12 wells prepared for each AMPPP within a single experiment. In several instances, more than one spore concentration was used in order to determine the efficacy of certain AMPPPs as a function of the number of target spores. Stock solutions of each AMPPP were prepared at a concentration of 1 mg/mL and 0–15 microliters of each peptide stock solution were added to a single well in the microtiter plate followed by a sufficient volume of water to bring the total well volume to 100 microliters. The peptides tested were prepared or obtained as described in Examples 1–5, 7, 9, 10, 12, 14, and 15. Typical peptide volumes assayed were 0, 1, 2, 3, 4, 5, 6, 7, 8, 9, 10, and 15 microliters, which corresponds to a final peptide concentration in the range of 0–150 micrograms/mL. The microtiter plates were sealed with parafilm and incubated at room temperature for 48 hours. The fungal growth was observed after 24 and 48 hours by microscope using a 4× and/or a 10× objective lens. The amount of spore germination and fungal growth was recorded as a quantitative measurement at each observation time using a system of pluses and minuses: [−] meant no germination having occurred, [+] meant swollen spores with an extended germ tube, [++] meant the beginnings of mycelial growth with the overall appearance of a loose lattice, and [+++] meant a dense mycelial growth with the overall appearance of a thick opaque meshwork. The MCIC value for each AMPPP tested was then recorded, where the MCIC value is defined as the lowest peptide concentration at which no spore germination occurred (rating=[−]). Table II lists mean MCIC values (stated as micrograms per mL) computed after 24 hours of treatment from at least three replicates with each AMPPP for each of two or three plant pathogenic fungi tested: P3 Fusarium (field isolate), *Trichoderma reesei* (a gift of Dr. John Ellis, USDA-ARS, Peoria, Ill.) Cercospora sp. (a gift of Dr. James Hawk, University of Delaware, Newark, Del.) and *Helminthosporium carbonum*.

TABLE II

| | MCIC Values With: | | | |
|---|---|---|---|---|
| Peptide No. | P3 Fusarium (10$^7$) | Trichoderma reesei (10$^6$) | Cercospora sp. (No. spores/test) (10$^6$) | Helminthosporium carbonum (*10$^5$ or 10$^6$) |
| Pep No. 1 | 19+/−5 | 35+/−6 | 29+/−5 | 20+/−0* |
| Pep No. 2 | 18+/−5 | 35+/−6 | 20+/−0 | 15+/−6* |
| Pep No. 3 | 20+/−0 | 20+/−0 | 45+/−6 | 20+/−0* |
| Pep No. 4 | 60+/−0 | 67+/−6 | Nd | 70+/−0 |

TABLE II-continued

| | MCIC Values With: | | | |
|---|---|---|---|---|
| Peptide No. | P3 Fusarium ($10^7$) | Trichoderma reesei ($10^6$) | Cercospora sp. (No. spores/test) ($10^6$) | Helminthosporium carbonum (*$10^5$ or $10^6$) |
| Pep No. 5 | 57+/–5 | Nd | Nd | 85+/–0 |
| Pep No. 6 | 37+/–9 | Nd | Nd | Nd |
| Pep No. 7 | 30+/–0 | 40+/–0 | 35+/–6 | 35+/–6 |
| Pep No. 8 | 38+/–0 | 38+/–5 | 68+/–21 | 65+/–6 |
| Pep No. 9 | 15+/–6 | 24+/–12 | 25+/–10 | 63+/–29 |
| Pep No. 13 | 15+/–6 | 13+/–5 | 26+/–6 | 37+/–15 |
| Pep No. 15 | 98+/–5 | 73+/–5 | Nd | 150+/–0 |
| Pep No. 16 | 65+/–6 | 50+/–8 | Nd | 90+/–0 |
| Pep No. 18 | 98+/–5 | 88+/–5 | Nd | 150+/–0 |
| Pep No. 19 | 35+/–7 | 75 (no replicates) | Nd | Nd |

Nd = No data

Most peptides tested were effective at low levels (less than 70 ug/ml) in preventing the growth of four different pathogens. Most of the peptides were approximately as active against fungi as against the bacterium Ecc SR319 (see below). The peptides, Nos. 7, 8, 15, and 18, however, were much more active against fungi than against Ecc SR319.

EXAMPLE 17

Antibacterial Bioassays

*Erwinia carotovora carotovora* strain SR319 (Ecc SR319) (a gift of Dr. C. H. Liao, USDA-ARS, Philadelphia, Pa.) was streaked on a plate of Luria-Bertani ("LB") broth agar and grown overnight at 28° C. After 24 hours, a loopful of Ecc SR319 was picked from the agar plate and was added to 3 ml of LB broth (10 g Bacto-tryptone, 5 g Bacto-yeast extract, and 10 g sodium chloride per liter of solution; autoclaved sterile) in a capped sterile 10 ml test tube. This culture was grown overnight before its optical density at 630 nm was recorded using a Dynatech MR 600 microplate reader (Dynatech Laboratories, Inc., Alexandria, Va.). A portion of the overnight culture was adjusted with Luria broth to obtain a culture with an optical density at 630 nm of 0.2. About 250 microliters of this culture was added to 2250 microliters of Luria broth in a capped, sterile 10 ml test tube before this diluted culture was grown for 3–4 hours at 28° C. in a shaking incubator until the optical density of the freshly grown culture at 630 nm reached 0.2. A portion of this mid-logarithmic growth phase culture was diluted 1000-fold with Luria broth to an approximate concentration of about $10^5$ colony forming units per ml of culture. About 85 microliters of this diluted culture were added to each well in a 96 well microtiter plate with three replicate sets of 12 wells prepared for each AMPPP within a single experiment. Stock solutions of each AMPPP were prepared at a concentration of 1 mg/ml and 1–15 microliters of each peptide stock solution were added to a single well in the microtiter plate followed by a sufficient volume of water to bring the total well volume to 100 microliters. Typical peptide volumes assayed were 0, 1, 2, 3, 4, 5, 6, 7, 8, 9, 10, and 15 microliters, which corresponds to a final peptide concentration in the range of 0–150 micrograms per ml. The microtiter plates were sealed with parafilm and incubated on a shaking platform at 28° C. for 44 hours. The optical density of each Ecc SR319 culture well was recorded at 20 hours and then at 44 hours. A minimum complete inhibitory concentration (MCIC) was then determined for each replicate set of varying peptide concentrations at which no bacterial growth was observed. Table III lists mean MCIC values (stated as micrograms per mL) observed after 20 hours of treatment from at least three replicate experiments with each AMPPP. The AMPPPs tested were prepared or obtained as described in Examples 1–5, 7, 9, 10, 12, 14 and 15.

TABLE III

| | MCIC Values |
|---|---|
| Pep No. 1 | 50 +/– 5 |
| Pep No. 2 | 80 +/– 0 |
| Pep No. 3 | 5 +/– 0 |
| Pep No. 4 | 5 +/– 0 |
| Pep No. 5 | 17 +/– 6 |
| Pep No. 6 | 23 +/– 6 |
| Pep No. 7 | Greater than 150 |
| Pep No. 8 | Greater than 150 |
| Pep No. 9 | 33 +/– 5 |
| Pep No. 13 | 33 +/– 5 |
| Pep No. 15 | Greater than 150 |
| Pep No. 16 | 30 +/ 0 |
| Pep No. 18 | Greater than 150 |
| Pep No. 19 | 30 +/– 10 |

Nearly all of the peptides tested were effective in controlling the growth of Ecc SR319 except Pep Nos. 7, 8, 15, and 18. These latter four peptides were not active against Ecc SR319 even at concentrations higher than 150 micrograms of peptide per milliliter. Note that Peptide Nos. 5, 6, 9, and 16 had better activity than at least one of the the parent monomers (Pep Nos. 1, 2, 4, and 12) when tested at equivalent microgram per mL quantities.

EXAMPLE 18

Oxygen Evolution Bioassay Phytotoxicity

The following procedure for the preparation of chloroplasts to use in an oxygen electrode is similar to that of Gupta et al., "Development and Use of Chlorotetracycline Fluorescence as a Measurement Assay of Chloroplast Envelope-Bound $Mg^{2+}$, "Plant Physiol. 89, (1989) 753–761. Spinach (Spinacia oleracea L. var. 'Melody') was grown in 1:1 peat/vermiculite potting mix in a growth chamber with a 10 hour light period. The chamber temperature was maintained at 21° C. (day) and 16° C. (night) during the growth period. All plants were used for chloroplast isolation after 6–8 weeks of growth.

In order to obtain an enriched chloroplast fraction, about 12 g of deribbed spinach leaves were thoroughly washed and surface dried. The leaves were then cut into small pieces, each about ½ inch square, and were placed in a small blender jar containing 50 mL of chilled homogenization medium (0.33M sorbitol, 50 mM Hepes-NaOH, pH 6.8, 2mM $Na_2EDTA$, 1 mM $MnCl_2$, 1 mM $MgCl_2$). The tissue was blended twice for three second intervals on high speed in a blender. The resulting homogenate was filtered through four layers of cheesecloth and two layers of miracloth (Behring Diagnostics, La Jolla, Calif.) into two chilled 30 mL glass centrifuge tubes. The filtered solution was centrifuged for 1.0 minute at 750 g (2,200 RPM) in a JS 13.1 swinging bucket rotor in a Beckman J2-21M centrifuge (Beckman Instruments, Inc., Somerset, N.J.). The supernatant was then decanted and the pellet was gently resuspended by swirling at 0° C. About 15 mL of homogenization medium was added to each tube of chloroplasts before the chloroplasts were layered onto a 40% Percoll gradient (6 mL Percoll, 9 mL homogenization medium, and 0.03 g bovine serum albumin) in a 30 mL glass centrifuge tube. These tubes were centrifuged for 4.0 minutes at 2500 g (4000 RPM) in a JS 13.1 swinging bucket rotor in a Beckman J2-21M centrifuge. The supernatant was removed and the resulting pellet was resuspended in a small amount of homogenization medium (about 500 microliters).

Plastid concentration was generally expressed on a chlorophyll basis. Chlorophyll was determined by the method of Arnon "Copper Enzymes in Isolated Chloroplasts, Polyphenol Oxidase in Beta Vulgaris," *Plant Physiol.* 24, (1949) 1–15. About 50 microliters of chloroplast stock suspension was added to 10 mL of 80% acetone and this solution was incubated 5.0 minutes in the dark and then centrifuged for 5.0 minutes at 500 g (1630 RPM) in a Beckman GP centrifuge. The absorbance of the acetone-chloroplast solution was monitored at 645 nm, at 663 nm and at 730 nm. The chlorophyll concentration was then calculated as 10× [(absorbance at 645 nm×20.2)+(absorbance at 663 nm×8.02)—background at 730 nm]. This gave the amount of chlorophyll in micrograms for the original 50 microliters of chloroplasts. The concentration of chloroplasts was then adjusted with homogenization medium so that 50 microliters of suspension contained 26 micrograms of chlorophyll. These chloroplasts were only active for 1½ to 2 hours and were therefore used immediately.

An oxygen electrode (Hansatech Instruments Ltd., Kings Lynn, Norfolk, England) was used to measure oxygen evolution from isolated chloroplasts. For a detailed discussion of the method see, D. Walker, "The Use of the Oxygen Electrode and Fluorescence Probes in Simple Measurements of Photosynthesis," supra. A saturated KCl solution was placed in the electrode well and a one-inch square of rolling paper or lens paper was placed in to the electrode well so that it soaked up KCl and formed an ionic bridge. A one-inch square of teflon membrane was then prepared, being careful not to touch its surface, and was placed over the soaked paper. Using the membrane applicator, an O ring was placed over the head of the electrode, thereby securing paper and membrane across the electrode. The CB-1D control box was turned on and the system was allowed to warm up approximately one hour before calibration. The system temperature was maintained at 20° C. with a circulating water bath. The system was then calibrated using air-saturated water from a vigorously shaken wash bottle of deionized water with the assumption that the oxygen concentration of air-saturated water is 276 nmoles/mL. Using the gain switch, the output was subsequently set so that the pen on the chart recorder was at the maximum chart height. To remove all air from the water in the cuvette and to zero the chart recorder, about 2–3 mg of sodium dithionite was added and the plotter pen was observed to move to the bottom of the graph. If the slope of the line was unstable, the membrane and the paper were removed and the setting up of the oxygen electrode was restarted.

In order to carry out a phytotoxicity bioassay with the oxygen electrode, the following components were added to the oxygen electrode cuvette: 830 microliters assay medium (homogenization medium adjusted to pH 7.6 plus 25 mM $NaH_2PO_4$), 50 microliters of 0.1M fresh $NaHCO_3$, 20 microliters catalase (a total of 49.6 units/microliter), and 50 microliters chloroplast suspension (added last). The light source to the electrode then was then illuminated. An initial lag phase was seen as the chloroplast system equilibrated. If the initial lag phase was greater than one minute, then the plants used for chloroplast isolation were judged to be inadequate. In productive experiments, a steady rate of oxygen evolution was established for 3–4 minutes, then 50 microliters of solution containing peptide were added using a Hamilton syringe. The oxygen evolution rate was monitored for 3 minutes after peptide addition. The reduction in rate of oxygen evolution in these experiments after the addition of a peptide was determined by comparing the slope of the chart recorder output line before the addition of the peptide to the slope of the line at a set time point after addition of the peptide. The results were normalized for chlorophyll content since there was some variability between experiments in chloroplast concentration. These rates were expressed as micromoles of oxygen per milligram of chlorophyll per hour. The final result was expressed as percent inhibition of oxygen evolution derived by dividing the rate of oxygen evolution after addition of the peptide by the initial control rate of oxygen evolution, multiplying that number by 100, and subtracting the resulting percent from 100 percent.

Table IV summarizes observations on several AMPPPs for chloroplasts exposed to peptides at a final concentration of 8 uM. The peptides were prepared or obtained as described in Examples 1–5, 7, 9, 10, 12, 14, and 15. Mean values and standard deviations were calculated from 8–10 replicate assays with each AMPPP. Control oxygen evolution rates were in the range of 72–283 umoles $O_2$/chlorophyll hour/mg. Multiple peptides were studied in each experiment to minimize day-to-day variability in the results.

TABLE IV

| Percent Inhibition of Oxygen Evolution | |
|---|---|
| Pep No. 1 | 70 +/− 18 |
| Pep No. 2 | 12 +/− 16 |
| Pep No. 3 | 100 +/− 0 |
| Pep No. 4 | 5 +/− 6 |
| Pep No. 5 | 100 +/− 0 |
| Pep No. 6 | 100 +/− 0 |
| Pep No. 7 | 39 +/− 30 |
| Pep No. 8 | 5 +/− 6 |
| Pep No. 9 | 100 +/− 0 |
| Pep No. 13 | 100 +/− 0 |
| Pep No. 15 | 100 +/− 0 |
| Pep No. 16 | 100 +/− 0 |
| Pep No. 18 | 3 +/− 5 |
| Pep No. 19 | 67 +/− 13 |

There was a wide range in the percent inhibition of oxygen evolution caused by different peptides. In particular, Peptide Nos. 3, 5, 6, 9, 13, 15, and 16 all caused 100 percent inhibition of oxygen evolution each time the experiment was performed. By contrast, it is interesting to note that Peptide No. 8, reverse Magainin 2, had an extremely low Phytotoxicity effect compared to native Magainin 2. Reversing the orientation of Magainin 2 allowed a retention of antifungal activity but a loss of antibacterial activity (while decreasing substantially the phytotoxicity of Peptide No. 8 relative to Peptide No. 1). Combining this peptide with other peptides as described in Examples contained in this patent could provide a mixture with cooperative antifungal and antibacterial activity but with much lower phytotoxicity than single peptides alone.

EXAMPLE 19

Whole Cell Phytotoxicity Screening Technique

Oxygen consumed by maize BMS suspension cells were determined as an indication of the relative phytotoxicity of antimicrobial peptides. Black Mexican Sweet (BMS) cell suspension cultures were maintained by transferring 25 mls of cell culture to 25 mls of fresh MSA2D media (4.4 g bottle of Murashige and Skoog basal salt mixture Sigma catalog No. M5524, 100 mg myoinositol, 150 mg L-asparagine, 30 g sucrose, 20 mls of 0.1 mg/ml 2.4-dichlorophenoxy acetic acid stock and 1 ml of vitamin stock consisting of 25 mg/100 ml calcium pantothenate, 50 mg/100 ml pyridoxine, 50 mg/100 ml nicotinic acid, 50 mg/100 ml thiamine, 200 mg/100 ml glycine all added to 1 liter sterile distilled water followed by autoclaving 25 minutes at 121° C.) in a capped sterile 250 ml Erlenmeyer flask 3 days after culture initiation. Four days later 12.5 mls of the cell culture was transferred to 35.5 mls of fresh MSA2D media. Cultures were continuously maintained by alternating 3 and 4 day transfer regimes. The cultures were shaken in low light at 125 RPM at room temperature. For oxygen consumption experiments cells were used one day after transferring to fresh media. Cells were poured into a sterile 50 ml centrifuge tube and allowed to settle by gravity. Spent media was drawn off and 7.8 mls of fresh MSA2D media was added per gram of settled cells. The cell stock solution was placed on a shaker for continued aeration and was used in all assays conducted on that day.

An oxygen electrode (Hansatech Limited, Kings' Lynn, Norfolk, England) was inspected to insure that no corrosion was present. A saturated KCl solution was then placed in the clean electrode well. A 1 inch square of rolling paper or lens paper was cut and placed over the well so that the edges of the paper soaked up KCl and formed an ionic bridge. A 1 inch square of teflon membrane was cut, being careful not to touch the surface, and placed over the soaked rolling paper. A membrane applicator was used to press an O-ring over the head of the electrode thereby securing paper and membrane across the electrode. The CB-1D control box (Hansatech Limited) was turned on and allowed to warm up approximately one hour before calibration. The CB-1D control box was set at 1X output. A chart recorder was set at 0.05 V input with a chart speed of 3 cm/min. A circulating water bath set at 20° C. was hooked up to the electrode chamber. The entire system was calibrated using air-saturated water obtained by vigorously shaking a wash bottle of distilled water. Using the gain switch, the output was set so that the pen on the chart recorder was at the maximum chart height (900=top). The oxygen concentration of air-saturated water was assumed to be 276 nmole/mL at 20° C. All air was removed from the water in the cuvette by adding 2–3 mg of sodium dithionite. The pen on the chart recorder responded by moving to the bottom of the graph. If the slope of the line was unstable, the membrane and rolling paper were removed and the set-up steps were repeated.

For a 1 mL assay, 888 uL water and 62.5 uL BMS stock cell suspension were added to the oxygen electrode cuvette. The final concentration of cells used in the assay was approximately 8 mg/mL. The rate of oxygen consumed by the cells was monitored on the chart recorder for 3 minutes. Fifty microliters of peptide was then added to the cuvette using a Hamilton syringe. (Peptide stocks were adjusted to deliver the desired concentration in a 50 uL volume). Oxygen consumption was monitored for 5 minutes after peptide addition. The time period for the complete test was 8 minutes.

The rate of suppression of oxygen consumption after the addition of a peptide was determined by comparing the slope of the line before the addition of the peptide to the slope of the line at a set time point after addition of the peptide. The rate of oxygen consumption after addition of the peptide was divided by the initial control rate of oxygen consumption and then multiplied by 100. This percentage was then subtracted from 100% to give the final result expressed as percent inhibition of oxygen consumption.

Mean values and standard deviations were calculated from 4–5 replicate assays with each AMPPP. The AMPPPs tested were prepared or obtained as described in Examples 1, 4, and 14. The results are tabulated in TABLE V.

TABLE V

| Percent Inhibition of Oxygen Consumption Caused by Addition of 4 µM Peptide | |
|---|---|
| Pep No. 1 | 65 +/– 6 |
| Pep No. 2 | 52 +/– 6 |
| Pep No. 4 | 59 +/– 6 |
| Pep No. 5 | 72 +/– 13 |
| Pep No. 8 | 16 +/– 12 |

Peptide No. 1 caused a much higher level of inhibition of oxygen consumption compared to the reverse peptide, Peptide No. 8. This result agrees with the preceding Example (see TABLE IV, Example 18) which showed that reversing the orientation of Peptide No. 1 significantly reduced the phytotoxic effects on chloroplast oxygen evolution. Results for Peptide No. 2 and Peptide No. 4 indicate that there is a greater overall phytotoxic effect on whole cells compared to the relatively low phytotoxic effect on isolated chloroplasts (see TABLE IV, Example 18). This result may not be surprising since the whole cell is much more complex and has numerous metabolic pathways which could be affected by a peptide. Peptide No. 5, an oligopeptide composed of monomers of Peptide No. 1, had no significantly different effect on phytotoxicity compared to the parent monomer.

EXAMPLE 20

Measure of Resistance to Proteolytic Degradation

In an attempt to determine the sensitivity of peptides to extracellular plant proteases, and to determine the site or sites of processing by these proteases, a system was designed to obtain extracellular fluid from leaves of maize, tobacco, or potato and to use these to test the stability of various peptides.

Extracellular fluid (ECF) was obtained by cutting interveinal pieces from tobacco leaf after they were rinsed in deionized water. The segments were submerged in water in a vacuum desicator and vacuum was applied for 5 to 10 min. The vacuum was released slowly, the leaves were blotted dry and 4 to 5 pieces were rolled and placed in a 50 mL disposable syringe barrel cut down so as to be able to fit in a swinging bucket centrigue rotor. The syringe barrel was placed in a 50 mL screw cap conical centrifuge tube and centrifuged in a swinging bucket rotor at 600×g for 30 min. The liquid was recovered and centrifuged in a microfuge for 10 min. The supernatant was stored at –80° C. and used in subsequent experiments.

To test the stability of a peptide to extracellular plant proteases, 10 ug of the peptide (1 mg/mL) was incubated with 10% extracellular fluid in 50 mM Tris HCL buffer, pH 7.4. The peptides tested were prepared or obtained as described in Examples 6, 13, and 14. After incubation at 37° C. for 0, 15, 30, 45 and 60 min the proteases were inactivated by the addition of trifluoroacetic acid (TFA) to 1% final concentration (v/v).

Peptides were analyzed by reverse phase chromatography on a 2.1×30 mm POROS R/H column (PerSpective Biosystems, Cambridge, Mass.) using a 5 to 35% acetonitrile gradient in 0.1% TFA on a Hewlett-Packard HP1090 high pressure liquid chromatograph (Hewlett Packard, Avondale, Pa.) at 3.5 mL/min. When the duration of incubation with the ECF was increased, it was observed that two early eluting peaks were generated from the parent peak. The results in Table VI illustrate the rate of disappearance of the parent peak (whole peptide) and thus indicates the relative resistance to proteolytic degradation; the slower the rate in decline of the peak height of the parent the slower the rate of degradation.

TABLE VI

| | Percentage of Area Under the Parent Peak | | | | |
|---|---|---|---|---|---|
| Peptide No./Time = | 0 | 15 | 30 | 45 | 60 |
| 1 | 100 | 23 | 18 | 5.3 | 0.5 |
| 11 | 100 | 95 | 92 | 82 | 73 |
| 12 | 100 | 115 | 107 | 111 | 102 |

EXAMPLE 21

Construction of Synthetic Peptide Gene Capable of Secretion and Establishment of the Synthetic Gene in *Escherichia coli.*

A synthetic peptide gene capable of secretion was designed on the basis of the universal genetic code and, for the portion of the synthetic gene distinct from the targeting signal peptide sequence, a maize codon usage table compiled from entries in GenBank (cf. D. M. Bashe and J. P. Mascarenhas, Maize *Gen. Coop. Newsletter* 63, 4–5 (1989)). This gene consisted of a portion of a carrot extensin gene encoding a plant signal peptide sequence targeting the extensin protein to the extracellular space (J. Chen and J. E. Varner, *EMBO J.* 4, 2145–2151 (1985)) joined through a DNA sequence containing an NcoI restriction endonuclease recognition site to a coding sequence for Peptide No. 12, Met-(SEQ ID NO. 20). The presence of the NcoI recognition sequence added an Ala residue between the carrot extensin signal peptide and Peptide No. 12. The synthetic AMPPP gene portion coding for Met-(SEQ ID NO. 20) was designed with flanking non-equal NcoI and PstI recognition sequences for convenient directed insertion into any plasmid vector containing plant gene expression regulatory signals. The AMPPP synthetic gene portion was prepared from two synthetic oligonucleotides chemically synthesized on a model 391 PCR-MATE automated oligonucleotide synthesizer (Applied Biosystems, Foster City, Calif.) and having the structures of (SEQ ID NO. 24) and (SEQ ID NO. 25). These gene portions were purified according to the manufacturer's specifications.

About 500 ng of each purified oligonucleotide was mixed in a 9 microliter volume of solution to which 1 microliter of 10X linker-kinase buffer was added (see T. Maniatis et al., *Molecular Cloning,* p. 396; Cold Spring Harbor Laboratory, Cold Spring Harbor, N.Y., 1982). The mixture was heated 15 minutes at 80° C. and then was cooled slowly to room temperature over 3 hours in 200–300 mL water. The mixture was then further chilled to 4° C. over 60 minutes by putting it in a refrigerator.

A plasmid vector into which the annealed synthetic AMPPP gene segment was to be cloned and which contained plant gene expression regulatory signals to be appended in the correct orientation was prepared by cutting the plasmid DEPGUSO (a gift of J. Cozzitorto, EniMont America Inc.) with the restriction enzymes NcoI and PstI (New England Biolabs, Beverly, Mass.).

The plasmid DEPGUSO contains various DNA segments cloned into the widely used plasmid pUC19 (C. Yanisch-Peron et al., *Gene* 33, 103–119 (1985)). These DNA inserts are, reading in order from the EcoR1 restriction endonuclease recognition site to the HindIII recognition site in the pUC19 polylinker, about 560 base pairs of DNA surrounding the 35S transcriptional start site from Cauliflower mosaic virus (Strasbourg strain) which terminates at the DdeI recognition site at +129 relative to the major transcriptional start site, a synthetic DNA segment flanked by XbaI and NcoI recognition sites and encoding the 32 amino acid leader peptide sequence of a carrot extensin gene (J. Chen and J. E. Varner, ibid.) followed by a codon for an addition Ala residue, a DNA coding sequence for *E. coli* beta-glucuronidase (GUS) (E.C.3.2.1.31), a small non-functional portion of the nptII gene from transposon Tn5 of about 50 base pairs, and about 700 base pairs of DNA derived from a PvuII fragment spanning the polyadenylation site or sites from the octopine synthase gene of the T-DNA from a Ti plasmid of Agrobacterium tumefaciens (H. De Greve et al., *J. of Mol. Applied. Gen.* 1, 499–511 (1982)).

Digestion of DEPGUSO with NcoI and PstI enzymes releases the GUS gene and provides a parent vector into which genes can be directly cloned in proper reading frame for expression as peptide or protein fusion products targeted for secretion in plant cells. The plasmid DEPGUSO was digested at 37° C. for 90 minutes in a total volume of 15 microliters containing 4 ug of DNA, 8 U of NcoI enzyme and 20 U PstI enzyme in 1X KGB buffer (M. McClelland et al., *Nucleic Acids Res.* 16, 364 (1988)) and the resulting DNA fragments were separated by gel electrophoresis on an 0.8% agarose gel in 1X TAE buffer (T. Maniatis et al., *op. cit.*, p. 156).

The larger DNA fragment was cut out with a scalpel and purified with Gene-Clean (Bio101, La Jolla, Calif.) according to the manufacturer's directions prior to resuspending the larger DNA) fragment in 15 microliters of distilled water. Four microliters of the larger DNA fragment (or about 500 ng of DNA were mixed with 0, 0.5 or 1.5 microliter of annealed synthetic AMPPP gene DNA in a total volume of 25 microliters containing 1X ligase buffer and 600 U T4 DNA ligase (New England Biolabs, Beverly, Mass.). These mixtures were incubated overnight at 15° C.

Five microliters of each ligation mixture were then added to 100 uL competent *E. coli* strain DH5α cells (GIBCO BRL, Life Technologies Inc., Gaithersburg, Md.) and the transformation mixes were each incubated for 40 minutes on ice. The mixes then were heat shocked 60 seconds at 42° C., incubated 2 minutes on ice, and subsequently stored at 37° C. for 45 minutes after the addition of 500 microliters SOC medium (T. Maniatis et al., *Molecular Cloning* (2nd edition), p. A.2; Cold Spring Harbor Laboratory, Cold Spring Harbor, N.Y., 1989). The transformed cells were then briefly spun down and each cell pellet was resuspended in 500 microliters LB broth (T. Maniatis et al., *op. cit.*, p. A.1).

Three 100 microliter portions of each transformed cell suspension was plated on fresh LB agar plates containing 100 ug/mL ampicillin and the plates were incubated overnight at 37° C.

Transformed *E. coli* clones containing appropriate plasmid constructs, the constructs being designated DEPMYP300, were identified by restriction enzyme mapping and DNA sequencing of plasmid DNAs isolated by a miniprep procedure from individual colonies grown overnight at 37° C. in five mL LB broth containing 50 ug/mL ampicillin (See T. Maniatis et al., *op. cit.*, pp. 1.25–1.28).

The plant expression vector DEPMYP300 DNA can be used for plant cell transformation without additional modification, utilizing transformation methods such as electroporation, microinjection or microprojectile bombardment which directly insert transforming DNA into target cells. Such transformation of totipotent embryogenic cells can lead to regenerable plants. Direct transformation methods such as these are valuable for crop species which are not easily transformed, such as with cultured embryogenic cells of monocot cereal crops.

EXAMPLE 22

Construction of Synthetic AMPPP Met-([Arg$^7$, Glu$^8$, Pro$^{23}$] Magainin 1)$_2$ Dimer Gene, Establishment of the Synthetic Gene in *Escherichia coli* and Regulated Expression of the Synthetic AMPPP Gene.

A synthetic AMPPP Met-([Arg$^7$, Glu$^8$, Pro23] Magainin 1)$_2$ dimer gene was designed on the basis of the universal genetic code and with flanking nonequal NcoI and PstI recognition sequences for convenient directed insertion into the polylinker region of the commercially available bacterial plasmid pKK233-2 (LKB/Pharmacia Inc., Piscataway, N.J.) capable of regulated expression in the gram negative bacterium *Escherichia coli*. Regulated expression of the synthetic AMPPP dimer gene is desirable to avoid deleterious effects on the growth of the host cells due to toxic activity of Met-([Arg$^7$, Glu$^8$, Pro$^{23}$] Magainin 1)$_2$. The synthetic gene incorporates ATG as the first codon to allow for expression of this peptide in an appropriate strain of *Escherichia coli*. This synthetic gene portion would be prepared from two synthetic oligonucleotides having the structures of (SEQ ID NO. 26) and (SEQ ID NO. 27) chemically synthesized on a model 391 PCR-MATE automated oligonucleotide synthesizer (Applied Biosystems, Foster City, Calif.) and would be purified according to the manufacturer's specifications.

About 1–3 micrograms of each purified oligonucleotide would be mixed in a 9 microliter volume of solution to which one microliter of 10X linker-kinase buffer would be added (See T. Maniatis et al., *Molecular Cloning*, p. 396; Cold Spring Harbor Laboratory, Cold Spring Harbor, N.Y., 1982). The mixture would be heated 15 minutes at 85° C. and then would be cooled slowly to room temperature over 3 hours in 200–300 mL water. The mixture would be then further chilled to 4° C. over 60 minutes by putting it in a refrigerator. Five micrograms of the plasmid pKK233-2 would be digested to completion in a total volume of 15 microliters with the restriction enzymes NcoI and PstI (New England Biolabs, Beverly, Mass.) according to the manufacturer's specifications or known methods. See T. Maniatis et al., *Molecular Cloning*, supra, pp. 98–106.

Two microliters of 5M ammonium acetate and 70 microliters of (−20° C.) 100% ethanol then would be added to the aqueous reaction mixture and the sample would be stored 10 minutes at −20° C. before it would be centrifuged in an Eppendorf microfuge at 4° C. for 30 minutes. The supernatant would be discarded and the pellet would be dried under vacuum for 3–5 minutes. The dried pellet then would be resuspended in 10 microliters sterile distilled water and the entire sample would be electrophoresed in an 0.8% agarose gel containing 1 microgram/mL ethidium bromide in 1X TBE buffer (89 mM Tris-OH, 89 mM boric acid, pH 8.3, 2.5 mM Na$_2$EDTA).

Full-length linear pKK233-2 plasmid DNA would be visualized under long-wavelength Ultraviolet light and the linear DNA band would be excised from the gel with a razor blade). Purified linear plasmid DNA would be obtained from this sample using Gene-Clean II(Bio101, La Jolla, Calif.) according to the manufacturer's specifications or similar procedures such as size exclusion chromatography. See T. Maniatis et al., *Molecular Cloning*, supra, pp. 464–467.

Linear pKK233-2 DNA and annealed oligonucleotides would be mixed in a molar ratio in the range of 1:3–1:10 using at least 0.5 micrograms of pKK223-2 DNA in a solution containing 16 microliters of DNA in water. Then 2 microliters of 10X ligase buffer (New England Biolabs, Beverly, Mass.) and 2 microliters of T4 DNA ligase (New England Biolags, Beverly, Mass.; 400 U/microliter) would be added. This ligation reaction mixture would be incubated overnight at 14°–15° C.

Competent *Escherichia coli* strain IG109 cells (I. Goldberg et al., "Cloning and expression of a collagen-analog-encoding synthetic gene in *Escherichia coli*," *Gene* 80, 305–314 (1989)) would be prepared by conventional means (See T. Maniatis et al., *op. cit.*, p. 250). This strain of *Escherichia coli* would be used because of its preferred genetic properties which aid in minimizing intragenic deletions within the synthetic AMPPP gene during strain maintenance. Two microliters of the ligation reaction mixture would be mixed on ice with 100 microliters of competent cells and the mixture would be left on ice for 30–60 minutes. The transformation mixture would then be heated at 42° C. for 60 seconds, chilled on ice for 2 additional minutes and subsequently would be stored at 37° C. for 45 minutes after addition of 500 microliters SOC medium (T. Maniatis et al., *Molecular Cloning*, (2nd edition), p. A.2; Cold Spring Harbor Laboratory, Cold Spring Harbor, N.Y., 1989). The transformed cells would be spun down and each cell pellet would be resuspended in 500 microliters LB broth (T. Maniatis et al., *op. cit.*, p. A.1). Three 100 microliters portions of each transformed cell suspension would be plated on fresh LB agar plates continuing 100 ug/mL ampicillin and the plates would be incubated overnight at 37° C. Transformed E. coli clones containing appropriate plasmid constructs, the constructs being designated DEPMYP300, would be identified by restriction enzyme mapping and DNA sequencing of plasmid DNAs isolated by a mini-prep procedure from individual colonies grown overnight at 37° C. in five mL LB broth containing 50 ug/mL ampicillin (See T. Maniatis et al., *op. cit.*, pp. 1.25–1.28).

Regulated expression of the synthetic [(f)Met-([Arg$^7$, Glu$^8$, Pro$^{23}$] Magainin 1)$_2$] gene would be achieved by fermenting a recombinant bacterial clone at 30°–37° C. and increasing the temperature of the culture to 42° C. for 2–60 minutes. The temperature of the culture could then be reduced to 37° C. for 30–90 minutes before the cells would be harvested. The bacterial cell paste could then be passed through a French press and the (f)Met-([Arg$^7$, Glu$^8$, Pro$^{23}$] Magainin 1)$_2$] protein could be purified by conventional means. See, for example, Chapter 16 of Current Protocols in *Mol. Biol.*, F. M. Ansubel et al., Eds.; Wiley Interscience, 1988. Alternatively, the bacterial cell paste enriched in [(f)Met-([Arg$^7$, Glu$^8$, Pro$^{23}$] Magainin 1)$_2$] might be utilized in any of the methods embodied within the present invention for direct delivery of AMPPP gene products or AMPPPs in general to plant tissues for the purpose of retarding or eliminating plant pathogen infection or colonization.

EXAMPLE 23

Subcloning of Plant Expression Cassette Containing AMPPP Gene into Recombinant Ti plasmid and Establishment in *Agrobacterium tumefaciens*.

The plant expression cassette contained in DEPMYP300, spanning the DNA region from the Cauliflower mosaic virus 35S promoter through the octopine synthase transcription terminator, was subcloned into a disarmed binary Ti plasmid for the eventual purpose of establishing the recombinant Ti plasmid in an *Agrobacterium tumefaciens* strain capable of transforming plant tissue for a large number of dicot crop species. Codon usage in the plant expression gene cassette DEPMYP300 was optimized for expression in maize plant tissue, but codon usage in this cassette is also acceptable for expression in certain dicot plants such as tobacco as judged by examination using the GCG software analysis program CodonFrequency (See J. Devereux et al., *Nucleic Acids Res.* 12, (1984), 387–395). About 1.3 micrograms of DEPMYP300 DNA was digested at 37° C. for 2 hours with 27 U BamH1 restriction enzyme (Promega Corporation, Madison, Wis.) in a total volume of 12 microliters of solution containing 1.2 microliters of 10X BamH1 buffer (Promega Corporation, Madison, Wis.). The digested DNA was then electrophoresed in an 0.8% agarose gel in 1X TAE buffer (T. Maniatis et al., *op. cit.*, p. 156). The smaller DNA fragment was cut out with a scalpel and purified with Gene-Clean (Bio101, La Jolla, Calif.) according to the manufacturer's directions prior to resuspending the larger DNA fragment in 15 microliters of distilled water.

About 1.0 microgram of the disarmed *Argobacterium tumefaciens* Ti plasmid pBin19B (a gift of D. Trollinger, EniMont America Inc.) was concurrently digested with the restriction enzyme BamH1 under the same conditions as described above for the digestion of DEPMYP300 DNA. The plasmid pBin19B is identical with the Ti plasmid pBin19 (M. Bevan, *Nucleic Acids Res.* 12, (1984), 8711–8721) except for the removal of a portion of the lac polylinker which nevertheless left the unique BamH1 and EcoR1 restriction endonuclease recognition sequences of the polylinker. The BamHl-cut pBin19B was phenol extracted and ethanol precipitated by standard practices (cf. section 2.1.1 in *Current Protocols in Molecular Biology*, F. M. Ausubel et al., eds.; John Wiley and Sons, New York, N.Y., 1989) prior to resuspension in 10 microliters of distilled water.

Enzymatic ligation reactions were then set up with 0.7 microliters of BamHl-cut pBin19B DNA and 3.0 microliter of the smaller BamH1 fragment of DEPMYP300 in a total volume of 10 microliters containing 3 U T4 DNA ligase (Promega Corporation, Madison, Wis.) and 1X ligase buffer (final concentration; Promega Corporation, Madison, Wis.).

The ligation sample was incubated 2 hours at room temperature before 2.0 microliters of the ligation mixture was added to 35 microliters competent *E. coli* strain DH5α on ice. This transformation mixture was maintained on ice for 45 minutes before it was heat shocked 60 seconds at 42° C. and was returned to ice for 2 minutes. The mixture was subsequently stored at 37° C. for 45 minutes after addition of 500 microliters SOC medium (T. Maniatis et al., *Molecular Cloning* (2nd edition), p. A.2; Cold Spring Harbor Laboratory, Cold Spring Harbor, N.Y., 1989). The transformed cells were then briefly spun down and the cell pellet was resuspended in 500 microliters LB broth (T. Maniatis et al., *op. cit.*, p. A.1).

Three 100 microliter portions of each transformed cell suspension was plated on fresh LB agar plates continuing 50 ug/mL kanamycin and the plates were incubated overnight at 37° C. Transformed *E. coli* clones containing appropriate plasmid constructs, the constructs being designated DEPMYP300/Bin19B, were identified by restriction enzyme mapping of plasmid DNAs isolated by a mini-prep procedure from individual colonies grown overnight at 37° C. in 5 mL LB broth containing 50 ug/mL kanamycin (T. Maniatis et al., *op. cit.*, pp. 1.25–1.28). A 5.0 mL culture of Agrobacterium tumefaciens strain LBA4404 (a gift of J. Willis, EniMont America Inc.) was grown overnight in YEB medium (See G. An et al. in Chapter 3, Section A, of *Plant Molecular Biology Manual* (Kluwer Academic Publishers, Boston, Mass., 1990)) containing 500 ug/mL streptomycin. The strain LBA4404 contains a Ti plasmid lacking a transforming T DNA segment (A. Hoekema et al., *Nature* 303, 179–181 (1983)). These cells were then concentrated 100-fold in YEB medium and 1–2 micrograms of DEPMYP300/Bin19B DNA were mixed with 200 microliters competent cells on ice. This mixture was frozen for 5 minutes in liquid nitrogen, then heat shocked by a 5 minute exposure at a temperature of 37° C. Then, 1.0 mL YEB medium was added to each transformation mixture and the mixtures were incubated 2.5 hours at 29° C. with moderate shaking. The cells were then spun down 30 seconds (12,500 rpm) in a room temperature microfuge, resuspended in 500 uL YEB medium and three 100 microliter portions of each transformed cell suspension were plated on fresh YEB agar plates containing 500 ug/mL streptomycin and 50 ug/mL kanamycin. These plates were incubated overnight at 37° C. Transformed *A. tumefaciens* clones containing appropriate plasmid constructs were identified by restriction enzyme mapping and DNA sequencing of plasmid DNAs isolated by a mini-prep procedure from individual colonies grown overnight at 29° C. in 5 mL YEB broth containing 50 ug/mL kanamycin and 500 ug/mL streptomycin (See, G. An, ibid.). Recombinant *A. tumefaciens* clones of the type identified herein can be used to transform a large number of crop species, primarily dicots, by methods known in the art of plant transformation.

EXAMPLE 24

Transformation of Tobacco Leaf Discs by *Agrobacterium tumefaciens* Strain Harboring a Recombinant Ti Plasmid Bearing a Synthetic AMPPP Gene.

Transformation of tobacco with foreign genes using recombinant Ti plasmids carried by strains of *Agrobacterium tumefaciens* has become a common practice for transferring marker genes or genes of agronomic interest into dicots. Standard methods of tobacco plant transformation with *Agrobacterium tumefaciens* strains bearing disarmed (i.e., non-virulent) Ti plasmids have been delineated. One such efficient method is transformation of freshly excised tobacco leaf discs. Any isolate of the *Agrobacterium tumefaciens* strain LBA4404 (cf. A. Hoekema et al., Nature 303, 179–181 (1983)) identified as described in Example 23 as bearing the plasmid DEPMYP300/Bin19B could be used in transformation of tobacco leaf discs, leading to the establishment of transgenic tobacco plants bearing the plant expression cassette DEPMYP300. As mentioned in Example 23, this recombinant expression cassette construct was subcloned in the disarmed binary Ti plasmid pBin19B for the eventual purpose of establishing the recombinant Ti plasmid in *Agrobacterium tumefaciens* strain LBA4404 which is capable of transforming plant tissue for a large number of dicot crop species, including tobacco.

The method of transformation of tobacco leaf discs with *Agrobacterium tumefaciens* strain LBA4404 harboring the recombinant plasmid DEPMYP300/Bin19B would be that described in detail by R. B. Horsch et al., in Chapter 5, Section A, of *Plant Molecular Biology Manual* (Kluwer Academic Publishers, Boston, Mass., 1990) entitled "Leaf disc transformation" beginning at procedure 4 on p. A5/3. The optional transformation step 7 on that page would not be used, nor would optional transformation step 14 on the next page. However, optional steps 13 and 16 on p. A5/4 of R. B. Horsch et al., ibid., would be used in establishing and, in the instance of step 16 of this reference, in verifying by at least one independent means, several putative transgenic tobacco plants successfully transformed with DEPMYP300/Bin19B. Indirect biochemical evidence in support of T DNA transfer into putative transgenic tobacco plant tissue can also be obtained by enzymatic detection of the nptII gene product encoded by the T DNA portion of the Agrobacterium vector pBin19B using radioactively labeled ATP and unlabeled kanamycin in a blotting procedure (cf. B. Reiss et al., *Gene* 30, 211–218 (1984) and A. Reynaerts et al. in Chapter 9, Section A, of *Plant Molecular Biology Manual* (Kluwer Academic Publishers, Boston, Mass., 1990) entitled "Selectable and screenable markers" on pp. A9/7-8).

Expression of the AMPPP fusion gene product encoded by the plant gene expression cassette DEPMYP300 in putative transgenic tobacco plants generated by the method described in this Example can be indirectly confirmed by detection of specific messenger RNA (mRNA) produced by this plant expression cassette through Northern hybridization analysis. Total RNA would be isolated from small portions of tobacco leaf sample collected from putative transgenic plants 4–8 weeks following their initiation by tobacco leaf disc transformation using a scaled up version of the RNA isolation method of T. C. Verwoerd et al. (*Nucleic Acids Res.* 17, 2362 (1989)). Briefly, about 10 grams of leaf tissue from each plant to be tested would be washed, cut up into a 50 mL Beckman centrifuge tube and placed in liquid nitrogen where the plant tissue would be ground slowly for 1–2 minutes using a ⅜-inch CRAFTSMAN cordless drill (Sears, Roebuck and Co., Chicago, Ill.) with a homogenizing drill bit or, optionally, with a plastic adapter which conformed to the shape of the bottom of the tube. About 25 mL of prewarmed (80° C.) extraction buffer ([0.1M LiCl, 0.1M Tris-HCl, pH 8.0, 0.1M Na₂EDTA, 1.0% sodium dodecyl sulfate]:phenol, 1:1; mixed just prior to use) would be added to each ground tissue sample and the samples would be vortexed for 30 seconds. About 12 mL of (chloroform:isoamyl alcohol, 24:1) would be added to each tube and the tubes again would be vortexed for 5–30 seconds.

The tube contents then would be centrifuged for 30 minutes at top speed in a room temperature model GP centrifuge (Beckman Instruments, Inc., Palo Alto, Calif.) and the upper liquid phase in each tube would be discarded. An equal volume of 4M LiCl plus 0.03% diethyl pyrocarbonate would be added to each tube (about 20–25 mL), the tubes again would be vortexed for 5–30 seconds and then they would be left overnight at 4° C. The tubes would be spun the next day at maximum speed in a table top centrifuge (Beckman Instruments, Inc., Palo Alto, Calif.) for 30 minutes and the supernatants would be discarded. The pellets would be briefly rinsed in 5–10 mL of 100% ethanol and respun for 5–30 minutes in a table top centrifuge at maximum speed.

The ethanol supernatant would be removed from each sample and each pellet would be resuspended in 5 mL of distilled water pretreated with 0.1% diethyl pyrocarbonate plus 5 microliters of RNasin inhibitor (Promega Corporation, Madison, Wis.). About 500 microliters of 3M sodium acetate, pH 5.5, and two volumes of (−20° C.) 100% ethanol would be added to each RNA-containing solution and all samples would be stored for 1.5–2 hours in an ice bath. The samples then would be spun for 30 minutes in a table top centrifuge at maximum speed, the supernatants would be discarded and each pellet would be briefly rinsed in 1–5 mL (−20° C.) 100% ethanol before the samples would be respun under the same conditions. The supernatants would be again discarded and each pellet would be resuspended in 5 mL distilled water pretreated with 0.1% diethyl pyrocarbonate.

The concentration of each sample would be determined spectrophotometrically at wavelengths of 230, 240, 260, 280, and 320 nm for a 1:400 dilution of each sample in distilled water. Optical density ratios of $A_{260}/A_{280}$ in the range of 1.3–2.0, $A_{240}/A_{260}$ and $A_{230}/A_{260}$ less than 1.0, and $A_{320}/A_{260}$ of less than 0.15 would be deemed acceptable; more preferred values would be $A_{260}/A_{280}$ in the range of 1.5–2.0, $A_{240}/A_{260}$ and $A_{230}/A_{260}$ less than 1.0, and $A_{320}/A_{260}$ of less than 0.10.

About 110 micrograms of each sample would be electrophoresed on a denaturing polyacrylamide gel by standard Northern hybridization blot techniques (cf. (T. Maniatis et al., *Molecular Cloning*, (2nd edition), pp. 7.37–7.52; Cold Spring Harbor Laboratory, Cold Spring Harbor, N.Y., 1989) and would be transferred to 0.22 micron Nylon membrane (MSI, Westboro, Mass.) according to conventional techniques (See, T. Maniatis et al., *Molecular Cloning*, (2nd edition), *op. cit.*, pp. 7.49–7.50). Whole DEPMYP300 plasmid DNA as described in Example 21 would be nick-translated using a standard nick translation kit (BRL GIBCO, Life Technologies Inc., Gaithersburg, Md.) according to the manufacturer's specifications. $^{32}$p-labeled plasmid DNA would be purified by Sephadex G-50 chromatography (cf. T. Maniatis et al., *Molecular Cloning*, p. 464; Cold Spring Harbor Laboratory, Cold Spring Harbor, N.Y., 1982). The radiolabeled plasmid DNA would then be hybridized to the RNA samples on the Nylon membrane by standard techniques (cf. T. Maniatis et al., *Molecular Cloning*, (2nd edition), p. 7.52; Cold Spring Harbor Laboratory, Cold Spring Harbor, N.Y., 1989) prior to washing the Nylon membrane in 1X SSC (cf. T. Maniatis et al., *Molecular Cloning*, p. 447; Cold Spring Harbor Laboratory, Cold Spring Harbor, N.Y., 1982) plus an additional wash in 0.1X SSC plus 1% sodium dodecyl sulfate at 58° C. for one hour. The air dried Nylon membrane then would be stored for 1–7 days with GBX-2 X-ray film (Eastman Kodak, Rochester, N.Y.) with 1–2 Cronex intensifying screens (DuPont Corporation, Wilmington, Del.) prior to development of the X-ray film. The resulting autoradiogram would show an RNA transcript of approximately 400 bases for those RNA samples which are taken from true transgenic plants.

EXAMPLE 25

ANTIMICROBIAL PEPTIDE COMPLEMENTARY MIXTURE BIOASSAYS

Preferred complementary mixtures of antimicrobial peptides within the scope of the present invention are those mixtures which include at least one antimicrobial peptide which is relatively active against at least one plant pathogenic fungus and a second antimicrobial peptide which is relatively active against at least one plant pathogenic bacterium. The combination of these two peptides provides complete inhibition of the growth of both the plant pathogenic bacterium and the plant pathogenic fungus without each impeding the respective activity of the other peptide.

For this Example, Peptide No. 1 (which is relatively antifungal) and Peptide No. 4 (which is relatively antibacterial) were tested. These peptides were prepared or obtained as described in Example 14. The antifungal bioassay with these peptides individually or in combination was performed as described in Example 16. Stock solutions of each peptide to be tested were prepared and yielded the final following concentrations in the microtiter plate assay wells:

| Peptide No. 1 | | Peptide No. 4 | |
|---|---|---|---|
| Stock Concentration | Final Concentration | Stock Concentration | Final Concentration |
| 66.67 ug/mL | 30 ug/mL | 133.34 ug/mL | 60 ug/mL |
| 44.45 ug/mL | 20 ug/mL | 88.89 ug/mL | 40 ug/mL |
| 22.23 ug/mL | 10 ug/mL | 44.45 ug/mL | 20 ug/mL |
| 11.12 ug/mL | 5 ug/mL | 22.23 ug/mL | 10 ug/mL |
| 5.56 ug/mL | 2.5 ug/mL | 11.12 ug/mL | 5 ug/mL |
| 2.78 ug/mL | 1.25 ug/mL | 5.56 ug/mL | 2.5 ug/mL |
| 1.39 ug/mL | 0.625 ug/mL | 2.78 ug/mL | 1.25 ug/mL |
| 0.695 ug/mL | 0.313 ug/mL | 1.39 ug/mL | 0.625 ug/mL |
| 0.347 ug/mL | 0.156 ug/mL | 0.695 ug/mL | 0.313 ug/mL |
| 0.1738 ug/mL | 0.078 ug/mL | 0.347 ug/mL | 0.156 ug/mL |

Forty-five microliters of each peptide stock solution and 45 microliters of sterile distilled water were added to a single well containing fungal spores for peptides tested alone. For peptides tested in all possible combinations, 45 microliters of one peptide at a selected concentration was added to 45 microliters of the second peptide at a selected concentration in a single well. The microtiter plates were sealed with parafilm and incubated at room temperature for 48 hours. Fungal growth was observed after 24 and 48 hours by microscope using a 4X and/or a 10X objective lens. The amount of spore germination and fungal growth was recorded as a qualitative measurement at each observation time using a system of pluses and minuses: [–] meant no germination having occurred, [+] meant swollen spores with an extended germ tube, [++] meant the beginnings of mycelial growth with the overall appearance of a loose lattice, and [+++] meant a dense mycelial growth with the overall appearance of a thick opaque meshwork. The MCIC value for each peptide was then recorded, with the MCIC value defined as the lowest peptide concentration at which no spore germination occurred (rating=[–]).

Table VII below lists the degree of spore germination for the individual peptides where the concentration of Peptide No. 1 (the relatively antifungal peptide in this mixture) is equivalent to its MCIC value. Table VII also shows the effect of combining these antimicrobial peptides at these same concentrations of the respective peptides in a mixture.

TABLE VII

| Peptide Concentration (in micrograms/mL) | | Degree of Spore |
|---|---|---|
| Peptide No. 1 | Peptide No. 4 | Germination |
| 20 | 0 | [–] |
| 0 | 5 | [+++] |
| 20 | 5 | [–] |

The antibacterial bioassay with these peptides individually or in combination was performed as described in Example 17. About 7.5 microliters of each peptide stock solution to be tested and 7.5 microliters of water or the second peptide stock solution were added to a single well in the microtiter plate for each experimental replicate. The peptide dilutions tested corresponded to final peptide concentrations as listed:

| Peptide No. 1 | | Peptide No. 4 | |
|---|---|---|---|
| Stock Concentration | Final Concentration | Stock Concentration | Final Concentration |
| 666.5 ug/mL | 50 ug/mL | 133.3 ug/mL | 10 ug/mL |
| 400 ug/mL | 30 ug/mL | 66.7 ug/mL | 5 ug/mL |
| 266.7 ug/mL | 20 ug/mL | 33.3 ug/mL | 2.5 ug/mL |
| 133.4 ug/mL | 10 ug/mL | 16.7 ug/mL | 1.25 ug/mL |
| 66.7 ug/mL | 5 ug/mL | 8.3 ug/mL | 0.625 ug/mL |
| 33.3 ug/mL | 2.5 ug/mL | 4.26 ug/mL | 0.313 ug/mL |
| 16.7 ug/mL | 1.25 ug/mL | 2.1 ug/mL | 0.156 ug/mL |
| 8.35 ug/mL | 0.625 ug/mL | 1.04 ug/mL | 0.078 ug/mL |
| 4.2 ug/mL | 0.313 ug/mL | 0.52 ug/mL | 0.039 ug/mL |
| 2.138 ug/mL | 0.156 ug/mL | 0.26 ug/mL | 0.0195 ug/mL |

The microtiter plates were sealed with parafilm and incubated on a shaking platform at 28° C. for up to 44 hours. The optical density of each Ecc SR319 culture well was recorded at 20 hours and 44 hours. A minimum complete inhibitory concentration (MCIC) was then determined for Peptide No. 1 and Peptide No. 4 alone.

Table VIII below lists the percent inhibition of bacterial growth in single wells in the microtiter plate for bacteria exposed in the individual peptides where the concentration of Peptide No. 4 (the relatively antibacterial peptide in this mixture) is equivalent to its MCIC value. Table VIII also shows the effect of combining these antimicrobial peptides at these same concentrations of the respective peptides in a mixture.

TABLE VIII

| Peptide Concentration (in micrograms/mL) | | Degree of Inhibition of Bacterial |
|---|---|---|
| Peptide No. 1 | Peptide No. 4 | Inoculum Growth (%) |
| 20 | 0 | 19 |
| 0 | 5 | 100 |
| 20 | 5 | 100 |

Comparison of the results summarized in Tables VII and VIII make it clear that the concentrations of 20 micrograms/mL for Peptide No. 1 and 5 micrograms/mL for Peptide No. 4 fulfill the requirements for a complementary mixture of the two peptides which effectively retards the growth of both a bacterial and a fungal plant pathogen.

The principles, preferred embodiments and modes of operation of the present invention have been described in the foregoing specification. The invention which is intended to be protected herein, however, is not to be construed as limited to the particular embodiments disclosed, since these are to be regarded as illustrative rather than restrictive. Variations and changes may be made by others without departing from the spirit and scope of the invention.

We claim:

1. A compound comprising a peptide which is a reverse antimicrobial peptide active against at least one microbial pathogen, said peptide having at least about an equal degree of resistance to proteolytic degradation when compared to a peptide of the identical sequence in the opposite order and wherein said reverse antimicrobial peptide is selected from the group consisting of reverse Magainins, reverse PGL$^c$, reverse P1's, reverse Cecropins, reverse Sarcotoxins, reverse Bombinins, reverse XPFs, reverse Thionins, reverse Defensins, reverse Melittins, and reverse PGL$^a$.

2. The compound of claim 1 wherein said peptide has the amino acid structure of (SEQ ID NO. 9) and functional derivatives thereof.

3. A compound of claim 1 wherein said peptide has the amino acid sequence of (SEQ ID NO. 10) and functional derivatives thereof.

4. A compound of claim 1 wherein said peptide has the amino acid structure of (SEQ ID NO 11), wherein Xaa$^1$, Xaa$^2$, Xaa$^3$, Xaa$^5$, Xaa$^6$, Xaa$^{11}$, Xaa$^{12}$, Xaa$^{13}$, Xaa$^{14}$, Xaa$^{16}$, Xaa$^{17}$, Xaa$^{18}$, and Xaa$^{19}$ may be the same or different and are selected from the group consisting of Ala, Arg, Cys, Asn, Asp Gln, Glu, Gly, His, Ile, Leu, Lys, Met, Phe, Pro, Ser, Thr, Trp, Tyr, and Val.

5. A compound of claim 4 wherein said peptide has the amino acid structure of (SEQ ID NO. 11) wherein Xaa$^1$ and Xaa$^3$ may be the same or different and are amino acids selected from the group consisting of Arg, Asp, Cys, His, Glu, Lys, Gln, Tyr, Thr, Trp, Met, Ser, Ala, Phe, Val, Ile, Leu, and Pro, Xaa$^2$ is an amino acid selected from the group consisting of Arg, Asp, Cys, His, Glu, Ser, Gly, Lys, Gln, Tyr, Met, Asn, Ala, Pro, and Thr, Xaa$^5$ is an amino acid selected from the group consisting of Ala, Cys, Pro, Gln, Glu, His, Met, and Trp, Xaa$^6$ is an amino acid selected from the group consisting of Thr, Trp, Tyr, Asp, Glu, Lys, Arg, Gln, His, Met, Ala, Cys, Pro, and Gly, Xaa$^{11}$ is an amino acid selected from the group consisting of Leu, Ile, Cys, Pro, Trp, Phe, Val, Ala, and Gly, Xaa$^{12}$ is an amino acid selected from the group consisting of Phe, Ile, Trp, Leu, Cys, and Val, Xaa$^{13}$ is an amino acid selected from the group consisting of Met, Trp, Tyr, Cys, Gln, Lys, His, Pro, Ser, and Arg, Xaa$^{14}$ is an amino acid selected from the group consisting of Gly, Leu, Ile, Val, Ala, Phe, Met, Cys, Thr, Ser, Trp, Tyr, Gln, Lys, Asn, Glu, His, Asp, and Arg, Xaa$^{16}$ is an amino acid selected from the group consisting of Ala, Met, Thr, Pro, Ser, Trp, Tyr, Gln, Lys, Asn, Glu, His, Asp, and Arg, Xaa$^{17}$ is an amino acid selected from the group consisting of Phe, Ala, Met, Pro, Cys, Ser, Thr, Trp, Tyr, Gln, Lys, Asn, Glu, His, Asp, and Arg, Xaa$^{18}$ is an amino acid selected from the group consisting of Asn, Ile, Cys, Pro, and Leu, and Xaa$^{19}$ is an amino acid selected from the group consisting of Phe, Cys, Ile, Leu, Trp, and Val.

6. The compound of claim 5 further comprising a single residue N-terminal addition which is a single amino acid bound to the N-terminus through a peptide bond.

7. The compound of claim 1 wherein said peptide has the amino acid sequence of (SEQ ID NO. 12) wherein Xaa$^1$ is an amino acid selected from the group consisting of Ser, Cys and Pro, Xaa$^2$ is an amino acid selected from the group consisting of Cys, Lys, His, Arg and Asn, Xaa$^6$ is an amino acid selected from the group consisting of Cys, Gly and Ala, Xaa$^{11}$ is an amino acid selected from the group consisting of Cys, Gly and Ala, Xaa$^{14}$ is an amino acid selected from the group consisting of Cys, Gly, His, Arg and Lys, Xaa$^{16}$ is an amino acid selected from the group consisting of Cys, Ser, Ala, Glu, and Thr, and Xaa$^{17}$ is an amino acid selected from the group consisting of Cys, His, Lys, Arg, and Phe.

8. The compound of claim 1 wherein said peptide has the amino acid sequence of (SEQ ID NO. 13) and functional derivatives thereof.

9. The compound of claim 1 wherein said peptide has the amino acid sequence of (SEQ ID NO. 14) and functional derivatives thereof.

10. The compound of claim 1 wherein said peptide has the amino acid sequence of (SEQ ID NO. 15) and functional derivatives thereof.

11. The compound in any of claims 1 or 2 further comprising a signal peptide, peptide bound to the N-terminus thereof.

12. The composition of claim 1 wherein said reverse antimicrobial peptide is a reverse Magainin.

13. The composition of claim 1 wherein said reverse antimicrobial peptide is a reverse PGL$^c$.

14. The composition of claim 1 wherein said reverse antimicrobial peptide is a reverse P1.

15. The composition of claim 1 wherein said reverse antimicrobial peptide is a reverse Cecropin.

16. The composition of claim 1 wherein said reverse antimicrobial peptide is a reverse Sarcotoxin.

17. The composition of claim 1 wherein said reverse antimicrobial peptide is a reverse Bombinin.

18. The composition of claim 1 wherein said reverse antimicrobial peptide is a reverse XPF.

19. The composition of claim 1 wherein said reverse antimicrobial peptide is a reverse Thionin.

20. The composition of claim 1 wherein said reverse antimicrobial peptide is a reverse Defensin.

21. The composition of claim 1 wherein said reverse antimicrobial peptide is a reverse Melitin.

22. The composition of claim 1 wherein said reverse antimicrobial peptide is a reverse PGL$^a$.

* * * * *

UNITED STATES PATENT AND TRADEMARK OFFICE
CERTIFICATE OF CORRECTION

PATENT NO. : 5,519,115
DATED : May 21, 1996
INVENTOR(S) : Mapelli et al.

It is certified that error appears in the above-identified patent and that said Letters Patent is hereby corrected as shown below:

Delete "ug/mL" wherever it appears throughout the patent and substitute --$\mu$g/mL--

Column 6, line 19, "monmers" should read --monomers--.

Column 11, line 13, delete "lo".

Column 14, line 34, "Cys His or Ser," should read --Cys, His, or Ser,--.

Column 14, line 35, "amono" should read --amino--.

Column 22, line 6, "MONOMER" should read --monomer--.

Column 26, line 7, "Skelatal" should read --Skeletal--.

Column 27, line 9 "Ash" should read --Asn--.

Column 27, line 25, "Lys-Als-Thr-Glu," should read --Lys-Ala-Thr-Glu,"--.

Column 28, line 66, "H$_2$N-(SEQ ID NO. 20)-Cys-S-S-Cys-(SEQ ID NO.20)-" should read --H$_2$N-(SEQ ID NO. 20)-Cys-S-S-Cys-(SEQ ID NO.20)*-".

Column 31, line 27, "Leu Xaa$^7$" should read -- Leu, Xaa$^7$--.

Column 31, line 28, "Ser Xaa$^{10}$" should read -- Ser, Xaa$^{10}$--.

Column 31, line 29, "Ala Xaa$^{19}$" should read -- Ala, Xaa$^{19}$--.

UNITED STATES PATENT AND TRADEMARK OFFICE
CERTIFICATE OF CORRECTION

PATENT NO. : 5,519,115
DATED : May 21, 1996
INVENTOR(S) : Mapelli et al.

It is certified that error appears in the above-identified patent and that said Letters Patent is hereby corrected as shown below:

Column 31, line 53, "Set" should read --Ser--

Column 31, line 55, "Set" should read --Ser--

Column 32, line 43, "His Xaa$^8$" should read -- His, Xaa$^8$--.

Column 32, line 44, "Gly Xaa$^{19}$" should read -- Gly, Xaa$^{19}$--.

Column 32, line 54, "Ash" should read --Asn--.

Column 34, line 3, "Set" should read --Ser--.

Column 41, line 11, "peptide-resinscavenger mixture" should read -- peptide-resin-scavenger mixture --.

Column 51, line 5, "Cells" should read --cells--.

Column 56, line 9,   "5      P1            (SEQ ID NO. )-" should read
                     --4     P1            (SEQ ID NO. 6)--.

Column 56, line 9, "     (head-to-tail    (SEQ ID NO. 2 )-" " should read
                   --5   Mag 2 dimer      (SEQ ID NO. 2 )-
                         (head-to-tail)   (SEQ ID NO. 2 )--.

Column 56, line 21, "Dislufide" should read --Disulfide--.

Column 58, lines 21-22, "thoretical" should read --theoretical--.

Column 59, line 2, "undecatrifluoracetate" should read --undecatrifluoroacetate--.

Column 59, line 17, "1 366" should read --1.366--.

UNITED STATES PATENT AND TRADEMARK OFFICE
CERTIFICATE OF CORRECTION

PATENT NO. : 5,519,115  Page 3 of 5
DATED : May 21, 1996
INVENTOR(S) : Mapelli et al.

It is certified that error appears in the above-identified patent and that said Letters Patent is hereby corrected as shown below:

Column 59, line 53, "2584:4," should read --2584.4,"--.

Column 60, line 22, "Pro$^{23}$Mag]" should read --Pro23]Mag--.

Column 61, line 17, "Ser$^{23}$]" should read --Ser23]--.

Column 61, line 67, "hexatrifluoracetate" should read --hexatrifluoroacetate--.

Column 62, line 62,     "Pep    19+/-5    35+/-6    29+/-5    20+/-0*",
                         No. 1 should read

-- Pep    19+/-5    35+/-6    29+/-5    20+/-0*
                           No. 1                                30+/-0--.

Column 63, line 13, "Pep    38+/-0" should read --Pep    38+/-5--.

Column 64, line 27, "30+/0" should read --30+/-0--.

Column 64, line 48, "Mg$^{2+}$, "Plant" should read --Mg$^{2+}$", Plant--.

Column 66, line 28, "uM." should read --$\mu$M.--.

Column 66, line 58, "Phytotox-" should read --phytotox---.

Column 67, line 59, "uL water and 62.5 uL BMS stock" should read --$\mu$L water and 62.5 $\mu$L BMS stock--.

Column 67, line 66, "50 uL volume" should read --50 $\mu$L volume--.

Column 69, line 2, "10 ug of the peptide" should read --10 $\mu$g of the peptide--

UNITED STATES PATENT AND TRADEMARK OFFICE
CERTIFICATE OF CORRECTION

PATENT NO. : 5,519,115

DATED : May 21, 1996

INVENTOR(S) : Mapelli et al.

Page 4 of 5

It is certified that error appears in the above-indentified patent and that said Letters Patent is hereby corrected as shown below:

Column 70, line 42, "containing 4 ug of DNA" should read --containing 4 µg of DNA--.

Column 70, line 51, "larger DNA)" should read --larger DNA--.

Column 70, line 59, "100 uL" should read --100 µL--.

Column 71, line 35, "Pro23 " should read --Pro$^{23}$--.

Column 72, lines 1-2, "See T. Maniatis et al., Molecular Cloning, supra, pp. 98-106."
    should read --(See T. Maniatis et al., Molecular Cloning, supra, pp. 98-106.)--.

Column 72, line 18 "blade)." should read --blade.--.

Column 72, lines 22-23, "See T. Maniatis et al., Molecular Cloning, supra, pp. 464-467."
    should read --(See T. Maniatis et al., Molecular Cloning, supra, pp. 464-467.)--.

UNITED STATES PATENT AND TRADEMARK OFFICE
CERTIFICATE OF CORRECTION

PATENT NO. : 5,519,115
DATED : May 21, 1996
INVENTOR(S) : Mapelli et al.

It is certified that error appears in the above-indentified patent and that said Letters Patent is hereby corrected as shown below:

Column 72, line 30, "Biolags," should read --Biolabs,--.

Column 74, line 41, "uL" should read --$\mu$L--.

Column 76, line 38, "(T. Maniatis" should read --T. Maniatis--.

Signed and Sealed this

Fifteenth Day of April, 1997

Attest:

BRUCE LEHMAN

Attesting Officer

Commissioner of Patents and Trademarks